US010548572B2

(12) United States Patent
Susumu

(10) Patent No.: US 10,548,572 B2
(45) Date of Patent: Feb. 4, 2020

(54) ULTRASOUND PROCESSING DEVICE

(71) Applicant: KONICA MINOLTA, INC., Chiyoda-ku, Tokyo (JP)

(72) Inventor: Yasuaki Susumu, Osaka (JP)

(73) Assignee: KONICA MINOLTA, INC., Tokyo (JP)

( * ) Notice: Subject to any disclaimer, the term of this patent is extended or adjusted under 35 U.S.C. 154(b) by 1031 days.

(21) Appl. No.: 15/040,929

(22) Filed: Feb. 10, 2016

(65) Prior Publication Data

US 2016/0256135 A1 Sep. 8, 2016

(30) Foreign Application Priority Data

Mar. 3, 2015 (JP) .................................. 2015-041242

(51) Int. Cl.
*A61B 8/08* (2006.01)
*A61B 8/00* (2006.01)
*G01S 7/52* (2006.01)

(52) U.S. Cl.
CPC ............ *A61B 8/5207* (2013.01); *A61B 8/485* (2013.01); *A61B 8/5223* (2013.01); *A61B 8/54* (2013.01); *G01S 7/52095* (2013.01); *A61B 8/5253* (2013.01)

(58) Field of Classification Search
CPC ......... A61B 8/5207; A61B 8/485; A61B 8/54; A61B 8/5223; A61B 8/4405; A61B 8/467; A61B 8/5253; G01S 7/52047; G01S 7/52022; G01S 7/52042; G01S 7/52095; G01S 7/52085
See application file for complete search history.

(56) References Cited

U.S. PATENT DOCUMENTS

| | | | | | |
|---|---|---|---|---|---|
| 5,795,297 | A | * | 8/1998 | Daigle | G01S 15/899 600/447 |
| 5,810,731 | A | * | 9/1998 | Sarvazyan | A61B 8/08 600/438 |
| 5,980,458 | A | * | 11/1999 | Clark | G01S 7/52046 600/437 |
| 6,099,471 | A | * | 8/2000 | Torp | A61B 8/5253 600/443 |

(Continued)

FOREIGN PATENT DOCUMENTS

| | | |
|---|---|---|
| JP | 5087378 B2 | 12/2012 |
| JP | 5555286 B2 | 7/2014 |

OTHER PUBLICATIONS

Thomenius, "Evolution of Ultrasound Beamformers" 1996, IEEE Ultrasonics Symposium, pp. 1615-1622 (Year: 1996).*

(Continued)

*Primary Examiner* — Katherine L Fernandez
*Assistant Examiner* — Yi-Shan Yang
(74) *Attorney, Agent, or Firm* — Holtz, Holtz & Volek PC

(57) ABSTRACT

An ultrasound processing device including an interleaver that obtains a combined wavefront frame sequence by interleaving a plurality of wavefront frame sequences; and a calculator that calculates shear wave speed and elastic modulus in a subject, by performing calculations using change amounts of propagation positions of a shear wave indicated by the combined wavefront frame sequence. The interleaving by the interleaver comprises frame interleaving and/or element array direction interleaving.

8 Claims, 32 Drawing Sheets

(56) References Cited

U.S. PATENT DOCUMENTS

| | | | | |
|---|---|---|---|---|
| 6,464,638 | B1* | 10/2002 | Adams | A61B 8/5253 600/443 |
| 6,701,341 | B1* | 3/2004 | Wu | A61B 5/0456 128/915 |
| 8,123,692 | B2 | 2/2012 | Lin et al. | |
| 9,144,418 | B2 | 9/2015 | Lin et al. | |
| 2009/0143676 | A1* | 6/2009 | Matsumura | A61B 8/08 600/438 |
| 2009/0203997 | A1* | 8/2009 | Ustuner | A61B 8/08 600/443 |
| 2011/0054316 | A1* | 3/2011 | Kristoffersen | G01S 7/52077 600/443 |
| 2011/0063950 | A1* | 3/2011 | Greenleaf | A61B 8/485 367/87 |
| 2012/0116220 | A1* | 5/2012 | Burcher | A61B 5/0048 600/438 |
| 2012/0133663 | A1* | 5/2012 | Tanigawa | G01R 33/5608 345/581 |
| 2012/0134233 | A1* | 5/2012 | Lin | G01S 7/52022 367/7 |
| 2013/0123630 | A1* | 5/2013 | Freiburger | G01S 7/52036 600/438 |
| 2013/0131511 | A1* | 5/2013 | Peterson | A61B 5/0048 600/438 |
| 2013/0245442 | A1* | 9/2013 | Hazard | G01S 7/52036 600/438 |
| 2013/0289402 | A1* | 10/2013 | Tabaru | A61B 8/08 600/438 |
| 2016/0192906 | A1* | 7/2016 | Lee | A61B 8/485 600/438 |

OTHER PUBLICATIONS

Techavipoo et al., "Noise Reduction Using Spatial-Angular Compounding for Elastography" May 2004, IEEE Transactions on Ultrasonics, Ferroelectrics, and Frequency Control, vol. 51, No. 5, pp. 510-520 (Year: 2004).*

Bouchard et al., "Image Quality, Tissue Heating, and Frame Rate Trade-offs in Acoustic Radiation Force Impulse Imaging," Jan. 2009, IEEE Transactions on Ultrasonics, Ferroelectrics, and Frequency Control, vol. 56, No. 1, pp. 63-76 (Year: 2009).*

Prager et al., "Three-dimensional ultrasound imaging," 2010, Proceedings of the Institution of Mechanical Engineers, Part H: Journal of Engineering in Medicine, vol. 224, No. 2, pp. 193-223 (Year: 2010).*

Nightingale, "Acoustic Radiation Force Impulse (ARFI) Imaging: A Review", 2011, Current Medical Imaging, vol. 7, No. 4, pp. 328-339 (Year: 2011).*

Doherty et al., "Acoustic Radiation Force Elasticity Imaging in Diagnostic Ultrasound" Apr. 2013, IEEE Transactions on Ultrasonics, Ferroelectrics, and Frequency Control, vol. 60, No. 4, pp. 685-701 (Year: 2013).*

Poelma et al., "Enhancing the dynamic range of ultrasound imaging velocimetry using interleaved imaging" 2013, Meas. Sci. Technol. vol. 24, pp. 1-10 (Year: 2013).*

* cited by examiner

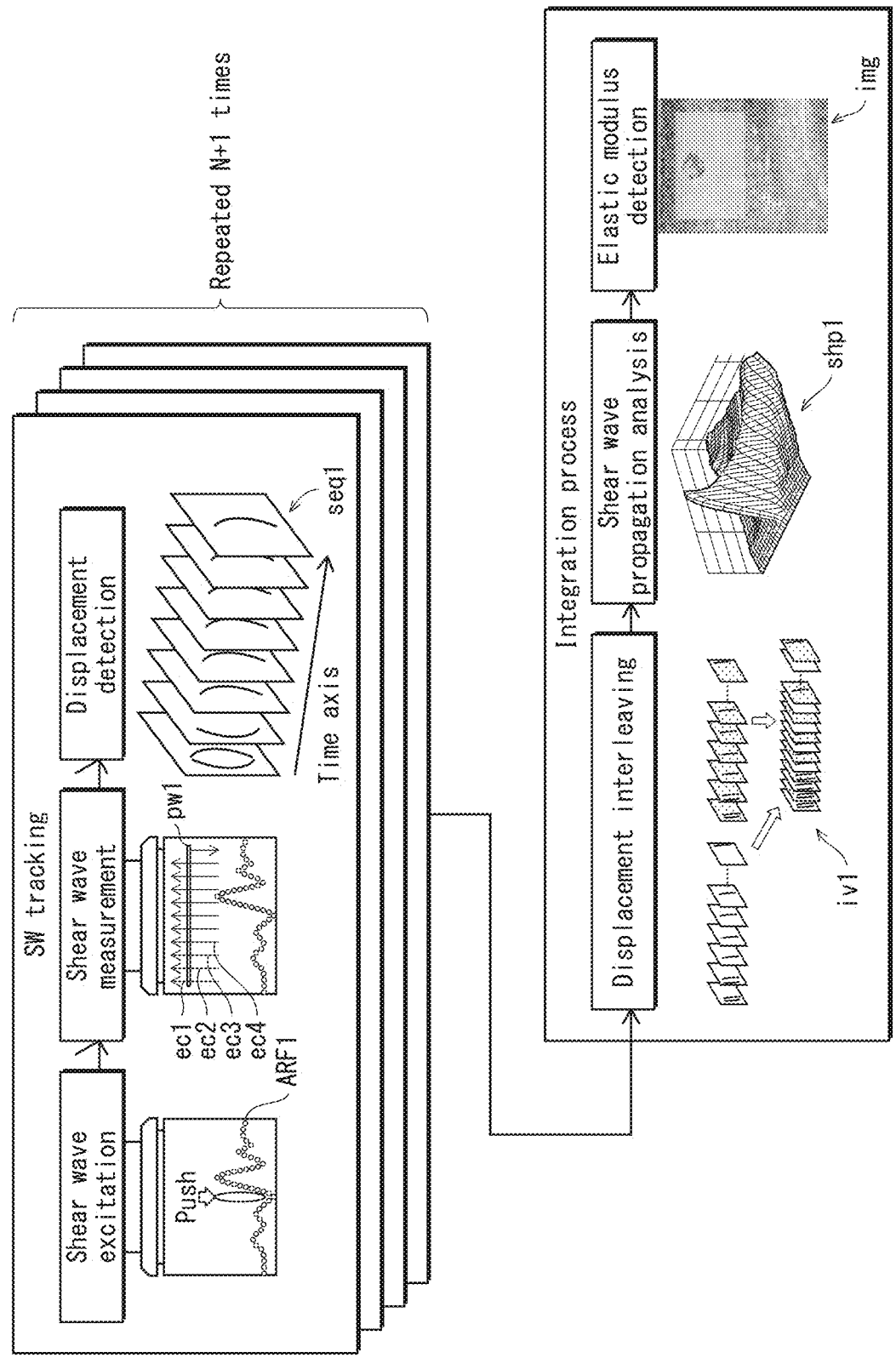

FIG. 14A  Elastic modulus image coordinate system

FIG. 20A
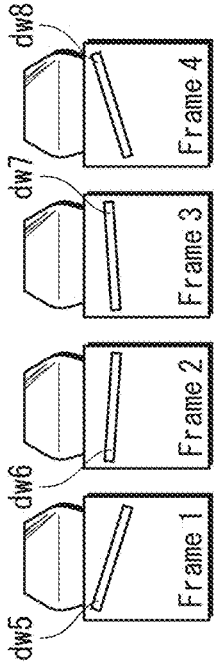
FIG. 20B
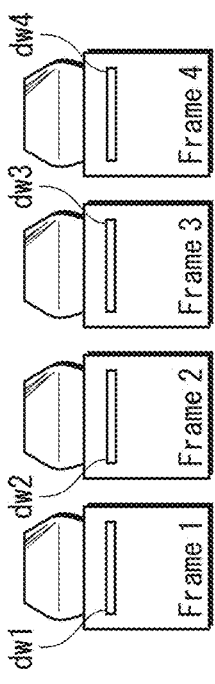
FIG. 20C
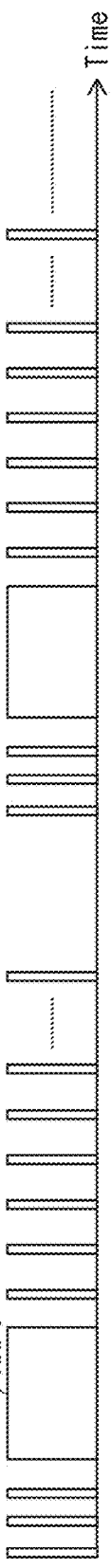
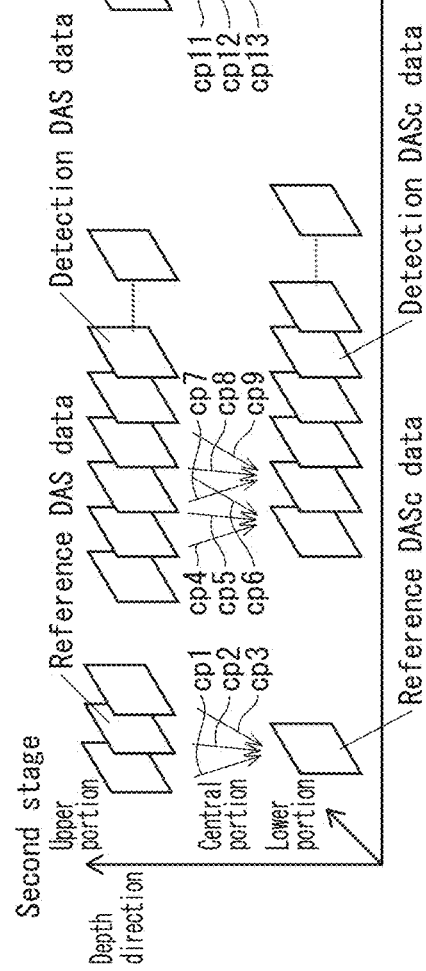

ULTRASOUND PROCESSING DEVICE

This application is based on an application No. 2015-041242 filed in Japan, the contents of which are hereby incorporated by reference.

BACKGROUND OF THE INVENTION (1) Field of the Invention

The present invention relates to ultrasound processing devices and particularly to improvement of elasticity evaluation using ultrasound.

(2) Description of the Related Art

Elasticity evaluation is a technique for acquiring and evaluating a spatial distribution of hard portions/soft portions of internal tissue in a subject, by transmitting ultrasound into the subject. In cancer screening, the importance of early detection of cancer tissue has long been advocated. However, it is very difficult to locate a small amount of cancerous tissue among healthy tissue occupying a large space within a living organism. Thus, various elasticity evaluation techniques using ultrasound processing devices have been established. The following describes shear wave speed (SWS) acquisition by an ultrasound processing device. Evaluation of elastic modulus is possible based on SWS.

A method of SWS acquisition comprises a "shear wave excitation" step, a "shear wave measurement" step, a "tissue displacement detection" step, and a "shear wave propagation analysis" step.

In "shear wave excitation", a region of interest (ROI) within the subject is defined and ultrasound is transmitted all at once from each of a plurality of acoustic elements constituting an ultrasound probe towards one location in the subject. Ultrasound transmitted all at once in this way is referred to focused ultrasound or an acoustic radiation force impulse (ARFI). According to this focused ultrasound, energy is concentrated in one location in a living organism and a large acoustic radiation force is generated. According to this acoustic radiation force, surrounding tissues receive a shearing force, are displaced, and a transverse wave is generated in a direction parallel to an element array direction of the ultrasound probe. This transverse wave is a "shear wave".

In "tissue displacement detection", ultrasound for detection purposes is transmitted from acoustic elements of the ultrasound probe. As ultrasound for detection purposes, a planar pulse may be used, for example. When a planar pulse is used to detect tissue displacement, the state of a wide range of space in a region of interest can be acquired at once. At a predefined sampling rate, the state of pertinent internal tissues is acquired a plurality of times. Subsequently, wavefront positions of a shear wave are derived from displacement between acquired tissue states. Thus, both a region in which the wavefront of the shear wave makes great progress and a region in which the wavefront of the shear wave makes slight progress can be acquired.

Magnitude of changes in wavefront position indicates magnitude of shear wave speed, and the magnitude of shear wave speed squared indicates hardness/softness of internal tissues that reflected a planar pulse. A region in which the shear wave makes a small amount of progress is determined to be healthy, and healthy tissue such as adipose tissue is determined to be present. A region in which the shear wave makes a comparatively large amount of progress is suspected to include cancerous tissue. The shear wave speed obtained by the above processing, when converted to an image of hardness/softness of tissue elasticity, allows visual representation of spatial distribution of hardness/softness of tissue elasticity.

An example of a method of obtaining tissue elasticity is disclosed in Japanese patent No. 5087378. This document discloses a frame interval adaptation device that interleaves ultrasound frames. According to this document, a set of beams 30 from one frame and a set of beams 32 from another frame are interleaved, and a beam from both frames is scanned during a frame interval 24 (FIG. 5, paragraph 0021). Using an average displacement history, so as to synchronize beam echo acquisition and cyclic displacement changes, acquiring displacement information is made easier by selecting ultrasound scanning frame intervals.

As another example, Japanese patent No. 5555286 discloses an ultrasound diagnostic device that calculates frame interval numbers according to displacement amounts that are inputted. This ultrasound diagnostic device calculates, based on movement amount (displacement) and force outputted from a displacement measurement unit 109 and a force measurement unit 110, distortion and elastic modulus of each point on a tomographic image, in order to calculate frame interval numbers according to distortion amounts.

SUMMARY OF THE INVENTION

Problems to be Solved by the Invention

However, it is hard to say that resolution is sufficiently high for conventional methods of SWS acquisition by ultrasound. When resolution of SWS acquisition is low, accuracy of SWS calculation is low.

A factor that limits resolution, for example, is difficulty in increasing sampling rate. Speed of a shear wave is higher while passing through hard tissue, and returns to its original speed after passing through the hard tissue. This "passing through" time is short, and therefore tissue state in the subject is acquired by transmitting ultrasound for detection purposes just prior to the "passing through" so that the ultrasound collides with tissue vibrating due to the shear wave, and receiving the reflected ultrasound. Sampling rate for SWS detection is determined according to the round-trip time from this ultrasound transmission until reflected ultrasound reception. When hardened tissue is positioned far from an acoustic element, the round-trip time from transmission of ultrasound for detection purposes until reception of reflected ultrasound is long, and increasing sampling rate is difficult. As a result, time resolution remains at a low level.

Further, another factor that limits resolution, for example, is difficulty in increasing spatial resolution. There are physical limits to narrowing element spacing. However, compared to when hardened tissue is near to an acoustic element, when hardened tissue is positioned far from an acoustic element, noise occurs more easily because reflected ultrasound arrives at one acoustic element from a wide spatial range, and accuracy of SWS calculation decreases.

In the disclosure of JP 5087378 (selection of ultrasound scanning frame intervals for synchronization of beam echo acquisition and distortion) and the disclosure of JP 5555286 (optimizing frame interval numbers according to distortion amount and elastic modulus), which represent background art in elasticity evaluation, technology to compensate for low resolution such as low time resolution and low spatial resolution is not disclosed, and further improvement is sought.

An objective of the present invention is to provide an ultrasound processing device that can improve resolution of a method of SWS acquisition and decrease a margin of error when calculating speed of a shear wave.

Means for Solving the Problems

The problems described above are solved by an ultrasound processing device comprising: an ultrasound signal processing circuit including: a push pulse controller that causes the acoustic element array to transmit focused ultrasound, in order to generate radiation force in a subject; a generator that obtains a wavefront frame sequence for each transmission of focused ultrasound, by generating wavefront frame data indicating wavefront positions of a shear wave at a plurality of points along a time axis, based on detection of propagation of the shear wave caused by radiation force generated by the focused ultrasound; an interleaver that obtains a combined wavefront frame sequence by interleaving a plurality of wavefront frame sequences obtained by the generator, and a calculator that calculates shear wave speed or elastic modulus in the subject, by using frame time intervals and change amounts of wavefront positions of a shear wave indicated by the combined wavefront frame sequence, wherein the interleaving comprises frame interleaving, in which a wavefront frame included in a wavefront frame sequence is inserted between two wavefront frames that are consecutive in a time direction among wavefront data included in another wavefront frame sequence, and/or element array direction interleaving, in which a data component from wavefront frame data included in a wavefront frame sequence is inserted between two data components that are arranged in an element array direction among data components included in another wavefront frame sequence.

BRIEF DESCRIPTION OF THE DRAWINGS

These and the other objects, advantages and features of the invention will become apparent from the following description thereof taken in conjunction with the accompanying drawings, which illustrate a specific embodiment of the invention. In the drawings:

FIG. 2 illustrates two or more shear wave tracking steps and an integration step;

FIG. 14A illustrates a position that is the subject of elastic modulus E(i,j)

FIG. 20A illustrates a detection pulse transmitted by a non-deflection compound method; FIG. 20B illustrates a deflection detection pulse transmitted by a deflection compound method; and FIG. 20C illustrates a timing chart of processing of the ultrasound processing device 101 pertaining to embodiment 2;

DESCRIPTION OF THE PREFERRED EMBODIMENTS (Embodiment 1)

The following describes an embodiment of an ultrasound processing device pertaining to the present invention, with reference to the drawings. The embodiment pertaining to the following description is one example used to clearly describe effects obtained from features and elements of the present invention. Accordingly, the present invention is not limited in any way by the following example, except for essential features described therein.

Figure 1:
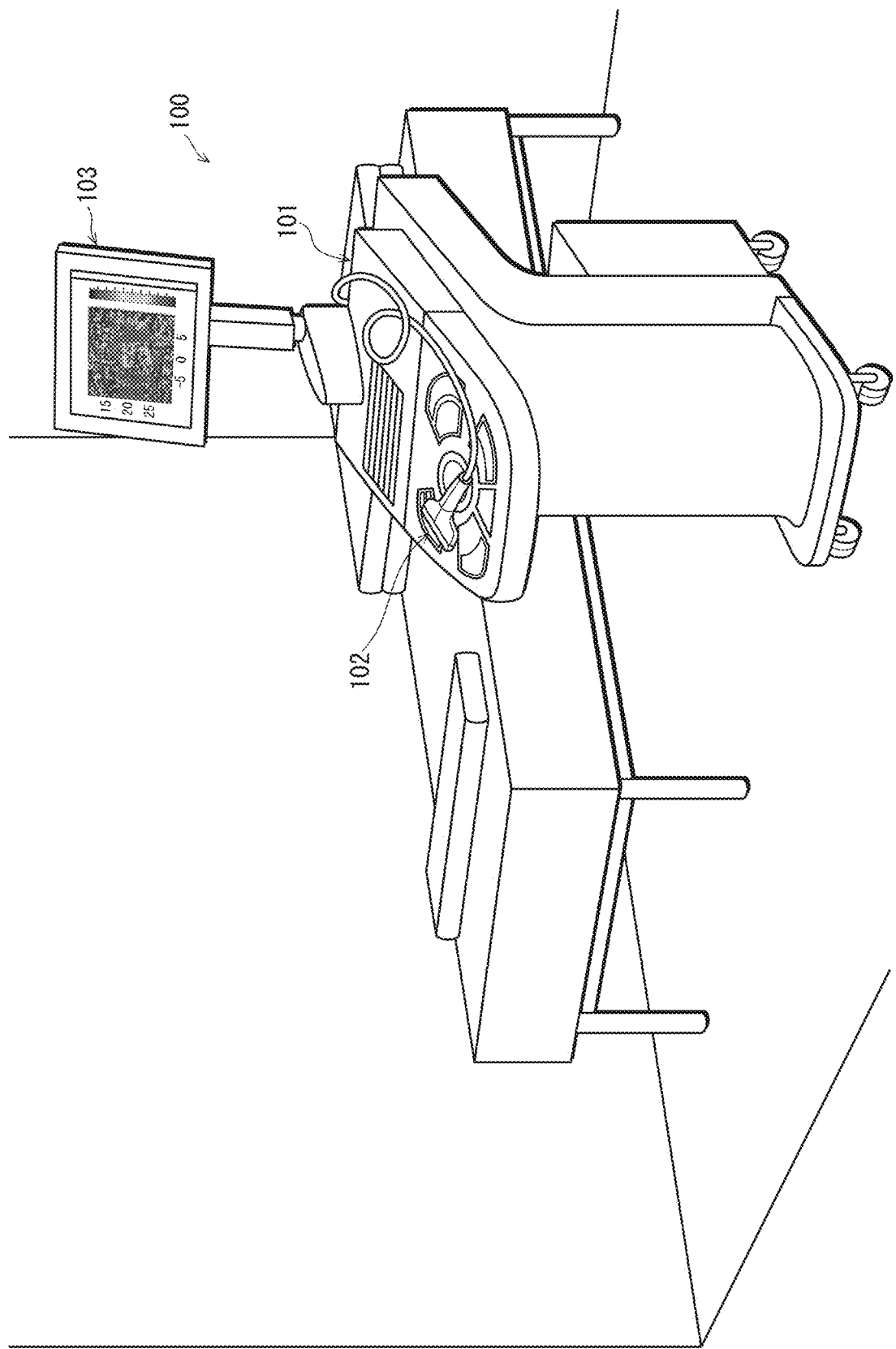
FIG. 1 illustrates an external configuration of an ultrasound diagnostic system including an ultrasound processing device.

An environment in which the ultrasound processing device pertaining to the present embodiment is used is described below. The ultrasound processing device is used in a diagnostic system in a medical practice. FIG. 1 illustrates an external configuration of an ultrasound diagnostic system including the ultrasound processing device. As illustrated in the drawing, an ultrasound diagnostic system 100 comprises an ultrasound processing device 101, an ultrasound probe 102, and a display 103. As illustrated in the drawing, the ultrasound probe 102 and the display 103 are distinct from the ultrasound processing device 101.

The ultrasound processing device 101 is a device (hub device) that has a core role in the ultrasound diagnostic system, receiving output signals from the ultrasound probe 102, performing diagnostic processing, and causing the display 103 to display a processing result.

The ultrasound probe 102 emits a transmission pulse by using an array of acoustic elements. A portion of emitted ultrasound for which acoustic impedance is different is reflected according to the difference in acoustic impedance.

The display 103 may be a liquid crystal display (LCD), and may display an SWS image, elastic modulus image, graph, numeric table, etc. An SWS image is a diagram, etc., that indicates propagation of a shear wave. An elastic modulus image indicates, for example, spatial distribution of elastic modulus in tissue within a subject, by position of colored pixels in a coordinate system in which a horizontal axis indicates an element array direction and a vertical axis indicates a depth direction.

This concludes description of the ultrasound diagnostic system 100. FIG. 2 illustrates an overview of procedure according to the ultrasound processing device 101. The overall procedure of the ultrasound processing device 101 is obtained by adding further improvements to the process of SWS acquisition described under Background Art. Differences from the SWS acquisition under Background Art are as follows.

First, the number of executions is different. Procedure according to the ultrasound processing device 101 comprises: a "shear wave excitation" step, a "shear wave measurement" step, and a "displacement detection" step, which are included in processing referred to as a shear wave tracking step that is executed N+1 times (N is an integer and equal to or greater than one, and therefore the shear wave tracking step is executed at least twice).

Second, the addition of a new step is a point of difference. Procedure according to the ultrasound processing device 101 comprises a "shear wave propagation analysis" step and an "elastic modulus calculation" step included in processing referred to as an integration process, and a "displacement interleaving" step is executed prior to the "shear wave propagation analysis" step.

In the "shear wave excitation" step, the ultrasound probe 102 is pressed against a subject, an operation to transmit reference detection pulse is performed, the reference detection pulse providing a reference for shear wave observation, and an operation to transmit an acoustic radiation force impulse (ARFI) is performed. Further, subsequent to ARFI transmission, an operation to transmit detection pulses is performed. "Push" in the drawing indicates transmission of focused ultrasound in a shear wave excitation step. "ARF1" indicates acoustic radiation force generated by the transmission of focused ultrasound.

The following describes a reference detection pulse and detection pulses. As a reference detection pulse/detection pulse, an ultrasound pulse or a planar pulse transmitted for each acoustic line may be used. Comparing an ultrasound pulse and a planar pulse, a planar pulse has an advantage that more data can be acquired at once. Accordingly, in the following description, a planar pulse is used as one example of a detection pulse, but other types of detection pulse may of course be substituted for the planar pulse. "PW1" in FIG. 2 indicates a detection pulse (planar pulse) outputted in a depth direction from acoustic elements in the shear wave measurement step. Upward arrows ec1, ec2, ec3, and ec4 indicate reflected ultrasound inputted to acoustic elements according to transmission of a detection pulse (planar pulse).

In the "displacement detection" step, wavefront frame data is generated from a reference detection pulse/detection pulse. Wavefront frame data is data indicating a wavefront of a shear wave at a point in time on a time axis, and is composed of a plurality of data components. Because the wavefront frame data is composed of a plurality of data components, the wavefront frame data has a predefined acoustic line density. Each data component is numerical data generated for an observation position in a region of interest (ROI), indicating a displacement amount of tissue at the observation position, and used primarily for calculation of displacement propagation data. For the convenience of description, waveform frame data is expressed in the form of an image. In FIG. 2, "seq1" indicates a sequence of wavefront frame data generated in a displacement detection step.

In the drawing, "iv1" indicates displacement interleaving by using two sequences of wavefront frame data.

The sign "shp1" indicates a three-dimensional illustration of a shear wave wavefront over time. "img" indicates an elastic modulus image that is one example of output data obtained by converting elastic modulus calculated by an elastic modulus calculation step. This concludes description of the SW tracking step and an integration step.

Figure 3A:
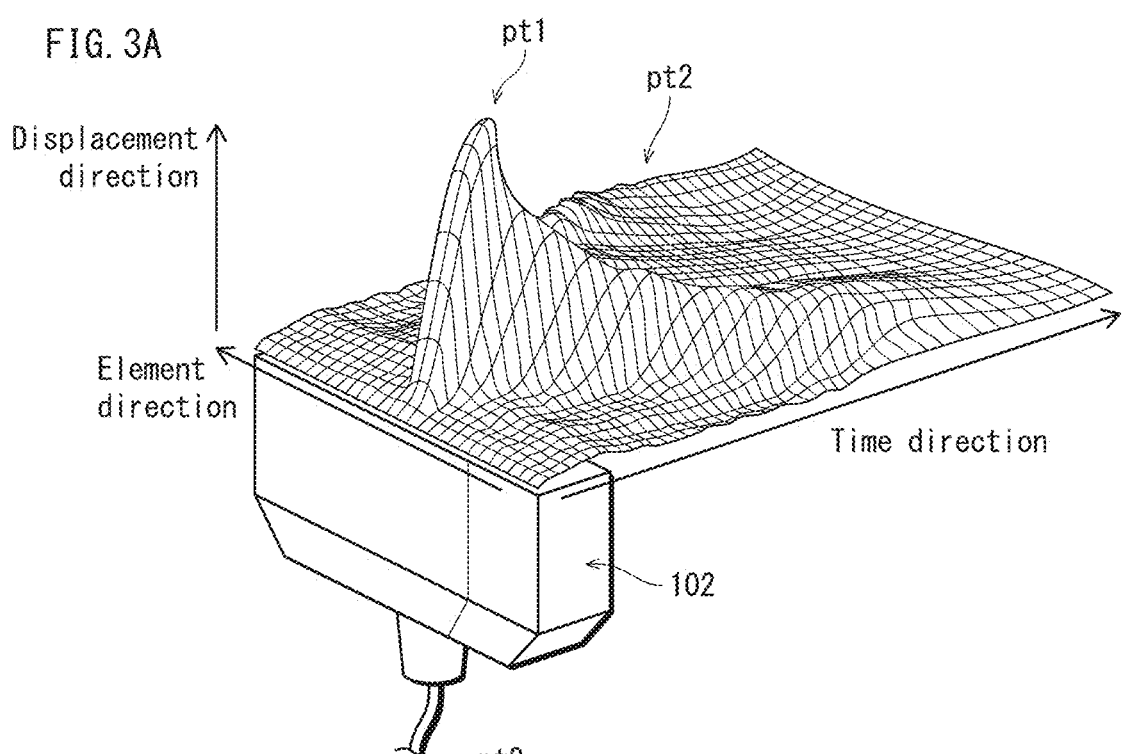
FIG. 3A illustrates a three-dimensional shape that is a shear wave propagation analysis result obtainable by propagation analysis.

FIG. 3A illustrates analysis results of shear wave propagation analysis. Analysis results of the shear wave propagation analysis are expressed in a three-dimensional coordinate system in which the X axis is a time direction, the Y axis is an element array direction (abbreviated in the drawings and hereafter as "element direction"), and the Z axis is a displacement amount. Specifically, the three-dimensional shape illustrated in FIG. 3A is drawn assuming a situation in which the probe 102 is below a subject consisting mainly of soft tissue, pressed against the subject, and the probe 102 transmits focused ultrasound. The soft tissue of the subject is shaken upwards by the radiation force from the focused ultrasound and the aftereffect continues for some time after transmission of the focused ultrasound. A peak pt1 in this three-dimensional shape is a portion of tissue that is greatly displaced by the radiation force of the focused ultrasound. A downward slope pt2 that flows smoothly from this peak is a portion in which a shear wave progresses in the element array direction.

Figure 3B:
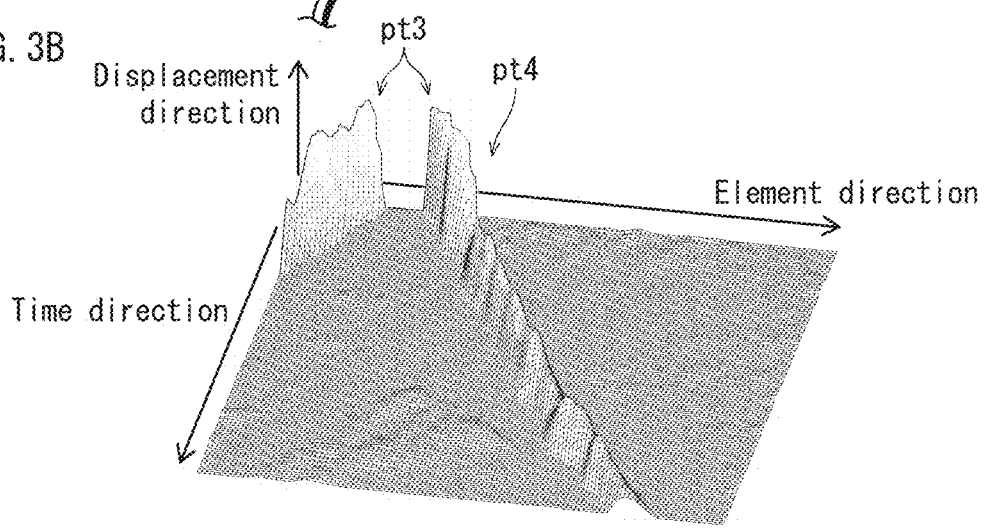
FIG. 3B and FIG. 3C illustrate other examples of three-dimensional shapes.
Figure 3C:
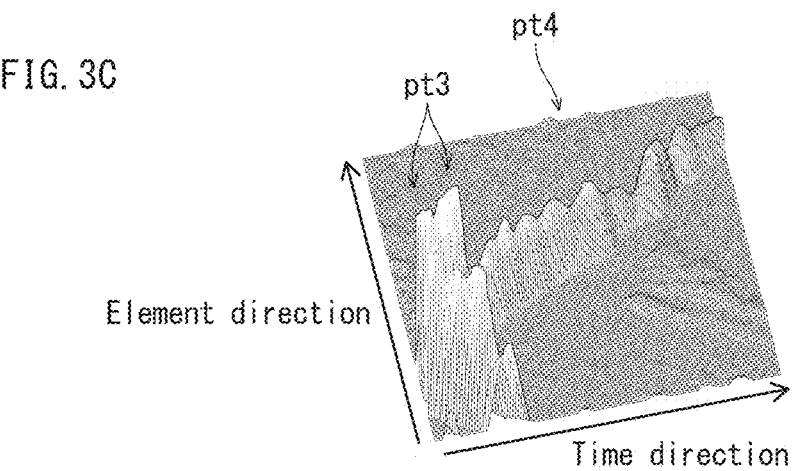

FIG. 3B and FIG. 3C illustrate other examples of three-dimensional shapes. Unlike FIG. 3A, in FIG. 3B and FIG. 3C there are two peak portions generated by radiation force from focused ultrasound (pt3, pt4). However, as time progresses, a shear wave wavefront progresses in the element array direction, as illustrated in FIG. 3A.

Figure 4A:
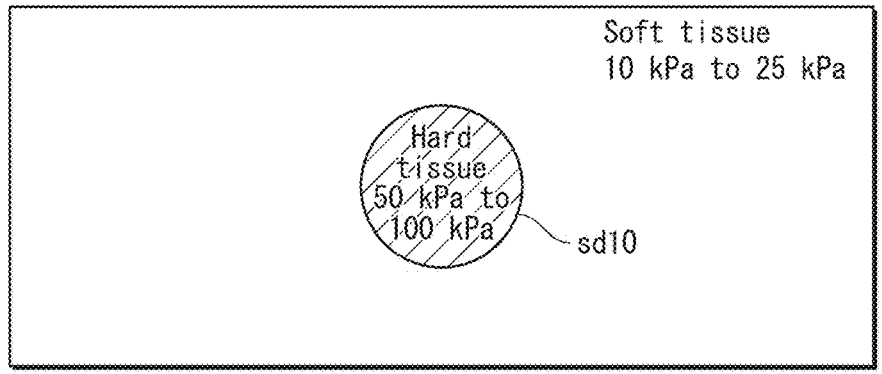
FIG. 4A illustrates a subject to be examined.

Because description of such three-dimensional shapes leads to complication, in the following description simplified displacement propagation data (indicating cross-sections at a plurality of depth positions) is used. FIG. 4A illustrates a subject to be examined. The subject in FIG. 4A has a hard tissue portion sd10 having an elastic modulus of 50 kPa to 100 kPa in the center of soft tissue having an elastic modulus of 10 kPa to 25 kPa.

Figure 4B:
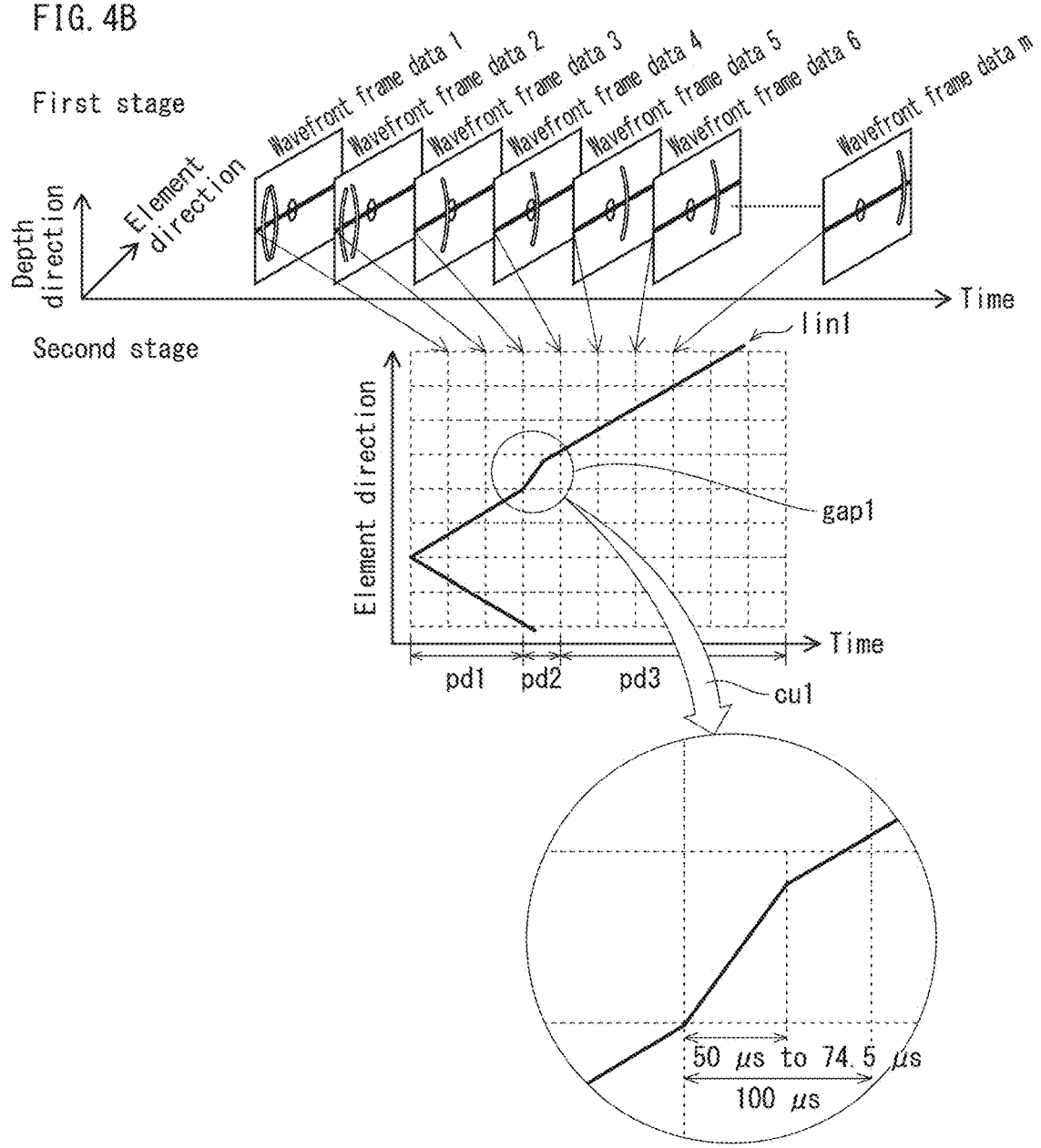
FIG. 4B illustrates a SWS sequence composed of wavefront frame data.

A first stage illustrated in FIG. 4B indicates a SWS sequence composed of wavefront frames. The "SWS sequence" is a sequence of wavefront frame data (also referred to as displacement data) obtained by a typical shear wave speed calculation process. The wavefront frame data indicates a shear wave wavefront that passes through the hard tissue in the element array direction. A second stage illustrated in FIG. 4B indicates displacement propagation data having a given depth position. In the second stage, "gap1" indicates a localized increase section in which speed of the shear wave increases while passing through the hard tissue. An arrow "cu1" indicates a close-up of the localized increase section. Here, the frame time interval of the wavefront frame data is 100 μs, while a time period of the localized increase section is in a numerical range of 50 μs to 74.5 μs. In the displacement propagation data of FIG. 4B, the horizontal axis is a time direction and the vertical axis is an element array direction. The bold line lin1 in FIG. 4B indicate a series of maximum points of the wavefront frame data, and gradient of the bold line lin1 indicates speed of the shear wave wavefront. The following describes three sections (pd1, pd2, pd3) appearing in the displacement propagation data of FIG. 4B. First, a section pd1 prior to the localized increase interval is described. When radiation force is generated by transmission of the focused ultrasound, two shear waves start and proceed towards both ends in the element array direction. One shear wave of the two shear waves proceeds to cross a front end of the acoustic element array. When the inside of the subject is filled with a uniform material (soft tissue), speed of progress is substantially constant. This period is a section immediately prior to the localized increase section in FIG. 4B.

A section pd2 is described below. When there is hard tissue in the path of a shear wave, normally the shear wave would be completely reflected at a surface of the hard tissue. However, elastic modulus of the hard tissue is two to ten times elastic modulus of the soft tissue and size of the hard tissue is small, and therefore only a portion of the shear wave passes through the hard tissue and proceeds along an outer surface of the hard tissue. Thus, because a portion of the shear wave proceeds through the hard tissue, a section in which speed of the shear wave changes is the localized increase section.

A section pd3 after the localized increase section is described below. When the transmitted wave emerges from the hard tissue, a portion of the shear wave that proceeded along a surface of the hard tissue and the transmitted wave rejoin to become one wave and the shear wave after rejoining returns to its original speed. This is the section after the localized increase section.

Equation 1, below, indicates a calculation of SWS when a localized increase in SWS is not considered, and Equation 2 indicates a calculation of elastic modulus when a localized increase in SWS is not considered. The numerator in Equation 1, the change amount of wavefront position in element direction, is a vertical distance in the grid of the second stage in FIG. 4B. The denominator in Equation 1, the displacement propagation time, is a horizontal distance in the grid of the second stage in FIG. 4B. Propagation time and change amount in Equation 1 and Equation 2 are not correctly calculated from the resolution of a grid such as in FIG. 4B, and therefore accuracy of SWS and elastic modulus is low.

[Math 1]

$$\text{shear wave speed} = \frac{\text{change amount of wavefront position in element direction}}{\text{displacement propagation time}} \quad \text{(Equation 1)}$$

$$\text{elastic modulus} = 3 \times (\text{shear wave speed})^2 \quad \text{(Equation 2)}$$

Because shear wave speed increases locally while passing through hard tissue, when spatial resolution in the element array direction or time resolution is low, increasing accuracy of calculation of shear wave speed is difficult, particularly during a period of passing through hard tissue. Because a change amount of wavefront position in a time period during which changes occur cannot be represented with high accuracy, the margin of error for sheer wave speed is high. Elastic modulus calculation is based on the square value of shear wave speed, and therefore the margin of error is conspicuous. Thus, the present embodiment aims to reduce this margin of error.

Ultrasound Processing Device 101

Figure 5A:
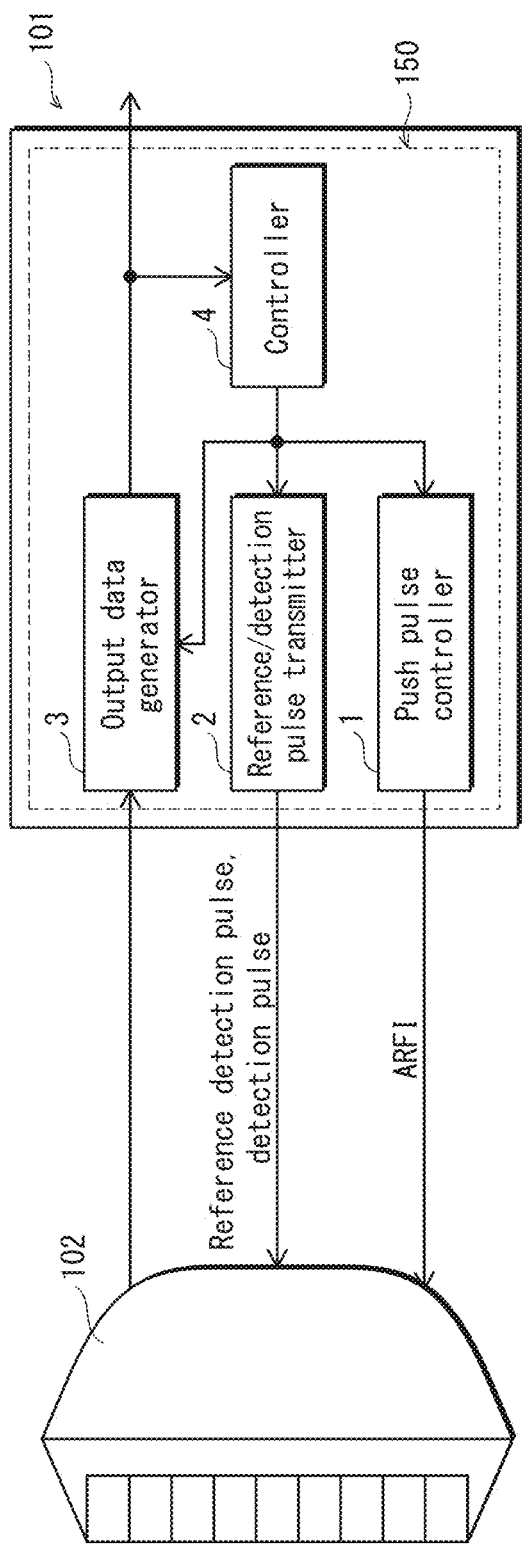
FIG. 5A illustrates an internal configuration of an ultrasound processing device 101.

FIG. 5A illustrates an internal configuration of the ultrasound processing device 101. The following describes a schematic configuration of the ultrasound processing device 101, with reference to FIG. 5A. As illustrated in FIG. 5A, the ultrasound processing device 101 comprises an ultrasound signal processing circuit 150, and the ultrasound signal processing circuit 150 comprises a push pulse controller 1, a reference/detection pulse transmitter 2, an output data generator 3, and a controller 4.

The push pulse controller 1 causes the ultrasound probe 102 to transmit focused ultrasound that is focused on a specific position in a region of interest (ROI) in the subject. Focused ultrasound is pulsed ultrasound having a large number of waves. As illustrated in FIG. 2, when a SW tracking step is executed multiple times, the push pulse controller 1 causes focused ultrasound to be transmitted to the same position each time. This is because radiation force under the same conditions is to be generated in the subject for interleaving execution.

The reference/detection pulse transmitter 2, transmits a reference detection pulse prior to transmission of focused ultrasound by the push pulse controller 1, and transmits a plurality of detection pulses after ARFI transmission. Transmission interval of detection pulses is determined by pulse repeat time (PRT). PRT can be set according to hardness/softness of tissue to be measured. A time interval from ARFI transmission to transmission of a first detection pulse can be set by a time offset. An interval from transmission of focused ultrasound to transmission of the first detection pulse according to time offset setting can be delayed by a time equal to half of the PRT.

The output data generator 3 generates output data based on execution of reception processing and receive signals in SWS acquisition. This reception processing includes (1) reception of reflected ultrasound generated by reflection of a reference detection pulse, and (2) reception of reflected ultrasound generated by reflection of detection pulses. When a planar pulse is used as ultrasound transmitted by the ultrasound probe 102, the reception described above is input into acoustic elements of the ultrasound probe 102 of reflected ultrasound corresponding to a plurality of acoustic line positions.

The controller 4 instructs the push pulse controller 1, the reference/detection pulse transmitter 2, and the output data generator 3 with required controls for the SW tracking step. Here, this means instructing the push pulse controller 1 to cause transmission of focused ultrasound, the reference/detection pulse transmitter 2 to transmit a reference detection pulse or detection pulse, and the output data generator 3 to receive reflected ultrasound generated by reflection from a shear wave.

Figure 5B:
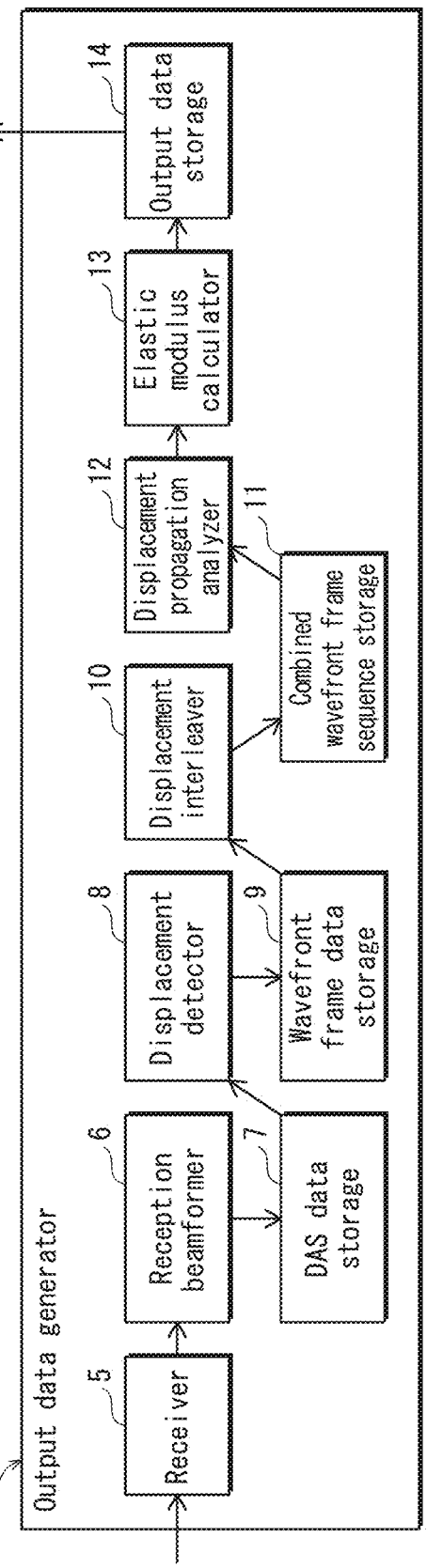
FIG. 5B illustrates an internal configuration of an output data generator 3.

FIG. 5B illustrates a configuration of the output data generator 3. As illustrated in the drawing, the output data generator 3 comprises a receiver 5, a reception beam former 6, a delay-and-sum (DAS) data storage 7, a displacement detector 8, a wavefront frame data storage 9, a displacement interleaver 10, a combined wavefront frame sequence storage 11, a displacement propagation analyzer 12, an elastic modulus calculator 13, and an output data storage 14.

The receiver 5, when receiving reflected ultrasound, demodulates signals inputted from the acoustic elements, and obtains element input signals that are high-frequency signals (radio frequency (RF) signals) via analogue/digital (A/D) conversion.

The reception beam former 6, when receiving a reflected reference detection pulse or a reflected detection pulse, performs multi-focus beamforming with respect to element input signals (RF signals) inputted from each of the acoustic elements. "Multi-focus beamforming" is setting acoustic line positions to a center of an element region of each acoustic element, and setting a plurality of observation points along extension lines of each acoustic line position. When p acoustic line positions exist, and q observation points exist on each extension line of an acoustic line position, p×q observation points are set in an ROI. In this case, the reception beam former 6 selects each of the p×q observation points as a reception focus, and executes delay-and-sum of element input signals from the acoustic elements. In delay-and-sum for one observation point, delay is decreased for element input signals at the observation point and delay is increased the further from the observation point element input signals are at surrounding acoustic elements. Delay-and-sum is performed for each element input signal outputted from each acoustic element according to a receive profile curve determined by these delays. Acoustic line signals are obtained according to this delay-and-sum processing. When receiving reflected ultrasound from a reference detection pulse/detection pulse, reference DAS data/detection DAS data is obtained by executing the delay-and-sum described above, for each observation point within the ROI. The reception beam former 6 of the present embodiment, as a characteristic process thereof, sets an offset in the element array direction for acoustic line positions when performing delay-and-sum. When performing delay-and-sum, acoustic line positions are set to the centers of the element regions. When setting offset in the element array direction, these acoustic line positions are changed to intervals between elements. When delay-and-sum is performed after setting the offset in the element array direction, reference DAS data/detection DAS data can be obtained in a different phase to normal delay-and-sum. Reference DAS data/detection DAS data is composed of a plurality of data components, and therefore has a predefined acoustic line density.

The DAS data storage 7 stores DAS data obtained by delay-and-sum according to the reception beam former 6. DAS data includes reference DAS data corresponding to reference detection pulses and detection DAS data corresponding to detection pulses. Reference DAS data/detection DAS data is data indicating tissue state at one point in time on a time axis, and is composed of data components corresponding to a plurality of observation position in an ROI. Each data component indicates amplitude and phase of an acoustic line waveform formed by beamforming to a focus point of a corresponding observation position.

The displacement detector 8 generates wavefront frame data corresponding to each detection DAS data, by calculating differences between data components of detection DAS data and reference DAS data. Difference between data components are obtained by (i) calculating differences between amplitude and phase of acoustic line waveforms indicated by each data component of reference DAS data, and amplitude and phase of acoustic line waveforms indicated by each data component of detection DAS data that corresponds in position, and (ii) assigning difference values obtained by this calculation to be data components at positions corresponding to wavefront frame data. This processing is repeated for all measurement position in an ROI. The displacement detector 8 then executes line interpolation. Line interpolation is interpolating lines of data components that exist discretely in wavefront frame data, to enhance a wavefront of the shear wave.

The wavefront frame data storage 9 stores an SWS sequence composed of a plurality of wavefront frame data generated by the displacement detector 8.

The displacement interleaver 10 interleaves wavefront frame data included in an SWS sequence ("SWS sequence N") obtained by an N-th SW tracking step and wavefront frame data included in an SWS sequence ("SWS sequence N+1") obtained by an (N+1)-th SW tracking step. The combined wavefront frame sequence storage 11, which provides an interleaved SWS sequence (combined wavefront frame sequence) to the displacement propagation analyzer 12, stores the wavefront frame data sequence (combined wavefront frame sequence) obtained by the interleaving of the displacement interleaver 10.

The displacement propagation analyzer 12 converts wavefront frame data to displacement propagation data. This conversion is achieved by the following processing. First, a line of data components at a given depth position is extracted from wavefront frame data. Extracted data components are plotted to a predefined coordinate system (in which the horizontal axis is time and the vertical axis is the element array direction). Thus, displacement propagation data is obtained that corresponds to one depth position. By performing this data component line extraction and plotting for a plurality of positions in the depth direction, displacement propagation data is obtained that covers a defined depth range in a subject.

The elastic modulus calculator 13 calculates SWS and elastic modulus at a plurality of positions in an ROI when displacement propagation data is generated by the displacement propagation analyzer 12. This method is described later. By converting the SWS and elastic modulus obtained for the plurality of positions in the ROI into numerical values and pixels, an SWS image, an elastic modulus image, a graph, a table of numerical values, etc., are obtained and stored in the output data storage 14.

The output data storage 14 stores an SWS image, an elastic modulus image, a graph, a table of numerical values, etc., generated by the elastic modulus calculator 13, and provides them for display by the display 103. Note that the output data storage 14 may be omitted, and an SWS image, an elastic modulus image, a graph, a table of numerical values, etc., generated by the elastic modulus calculator 13 may be directly provided to the display 103.

This concludes description of elements of the output data generator 3.

(Details of Interleaving)

Interleaving by the displacement interleaver 10 is described in detail below.

(Selection of Wavefront Frame Data)

The following describes selection of wavefront frame data for interleaving by the displacement interleaver 10. The displacement interleaver 10 selects wavefront frame data obtained in any of a plurality of SW tracking steps as targets for interleaving. In particular, the displacement interleaver 10 selects wavefront frame data obtained in two consecutive SW tracking steps as targets for interleaving (wavefront frame data obtained in an N-th SW tracking step and wavefront frame data obtained in an (N+1)-th SW tracking step). This is because when wavefront frame data obtained in an N-th SW tracking step and wavefront frame data obtained in an (N+1)-th SW tracking step are selected for interleaving, resolution can be further increased. Hereafter, unless otherwise specified, wavefront frame data obtained in an N-th SW tracking step and wavefront frame data obtained in an (N+1)-th SW tracking step are selected for interleaving.

Next, interleaving type according to the displacement interleaver 10 is described below. Interleaving of the present embodiment is time direction interleaving, element array direction interleaving, and time direction-element array direction interleaving.

Time direction interleaving is, (i) during processing of an SWS sequence N+1, executing transmission and reception of a detection pulse in which the first detection pulse is provided with a time direction offset and not provided with an element array direction offset, (ii) generating wavefront frame data for detection DAS data obtained after delay-and-sum processing, and (iii) inserting, into a time axis of generated wavefront frame data from the SWS sequence N+1, wavefront frame data from SWS sequence N, so that the wavefront frame data from the SWS sequence N+1 and the wavefront frame data from the SWS sequence N alternate.

Element array direction interleaving is, (i) during processing of an SWS sequence N+1, executing transmission of a detection pulse that is not set to have a time direction offset while executing delay-and-sum processing on RF signals outputted from a plurality of acoustic elements that are provided with an element array direction offset, (ii) generating wavefront frame data for detection DAS data obtained after the delay-and-sum processing, and (iii) arranging wavefront frame data so that generated wavefront frame data from the SWS sequence N+1 alternates with wavefront data from the SWS sequence N. Hereafter, one set of wavefront frame data that has double acoustic line density and is generated by executing element array direction interleaving by using one set of wavefront frame data included in one wavefront frame sequence and one set of wavefront frame data included in another wavefront frame sequence is referred to as "combined wavefront frame data".

Time direction-element array direction interleaving is, (i) during processing of an SWS sequence N+1, executing transmission of a first detection pulse that is provided with a time direction offset while executing delay-and-sum processing on element input signals outputted from a plurality of acoustic elements that are provided with an element array direction offset, (ii) generating wavefront frame data for detection DAS data obtained after the delay-and-sum processing, and (iii) arranging generated wavefront frame data from the SWS sequence N+1 and wavefront data from the SWS sequence N to alternate on a time axis and arranging data components of wavefront frame data from the SWS sequence N+1 and data components of wavefront frame data from the SWS sequence N to alternate.

Figure 6A:
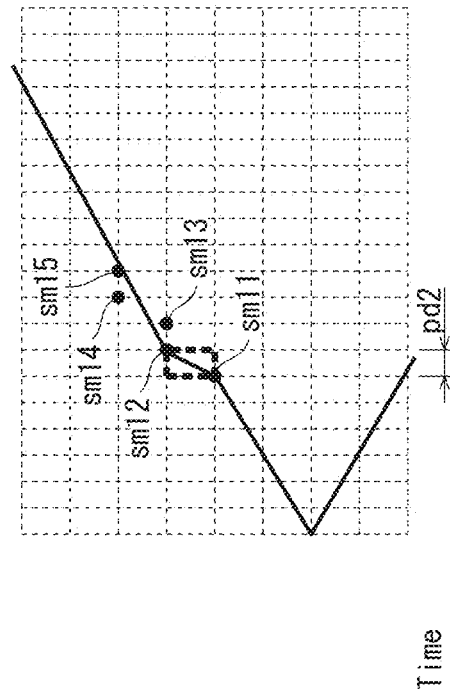
FIG. 6A illustrates no interleaving.
Figure 6B:
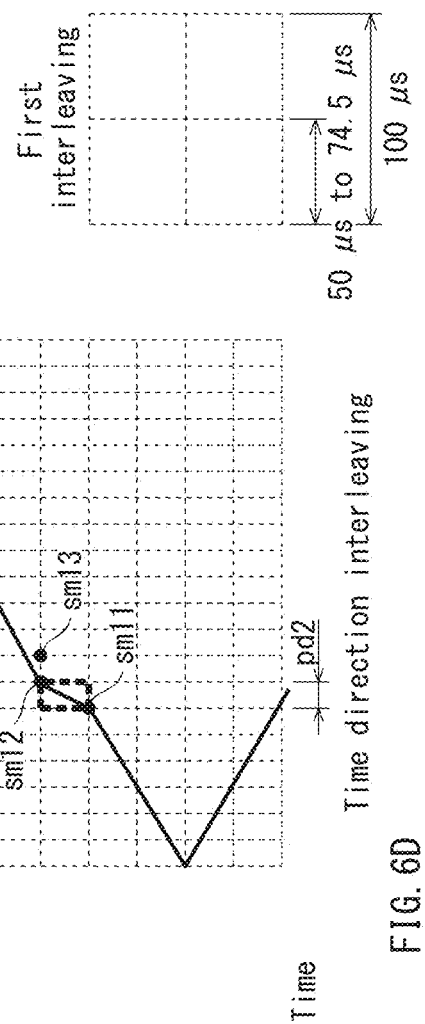
FIG. 6B illustrates interleaving in a time direction.
Figure 6E:
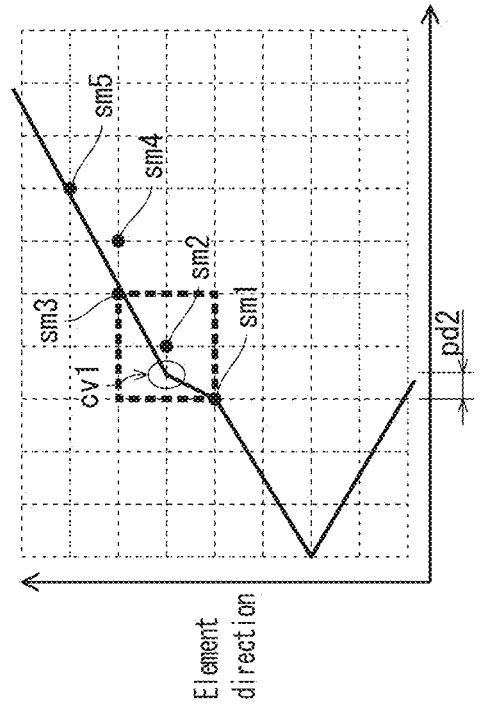
FIG. 6E illustrates frame intervals after a first interleaving.
Figure 6C:
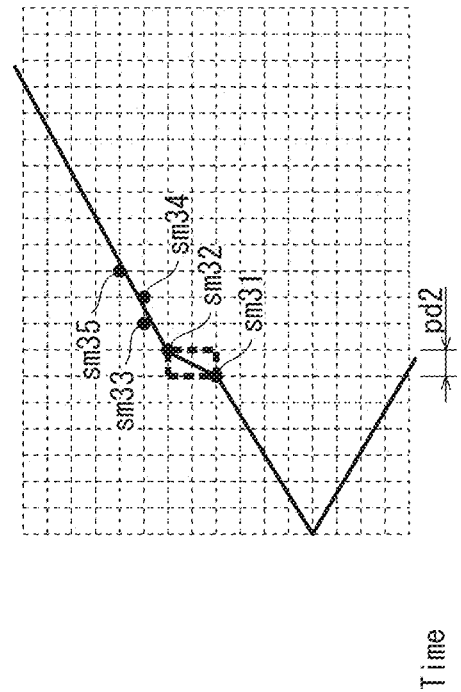
FIG. 6C illustrates interleaving in an element array direction.
Figure 6D:
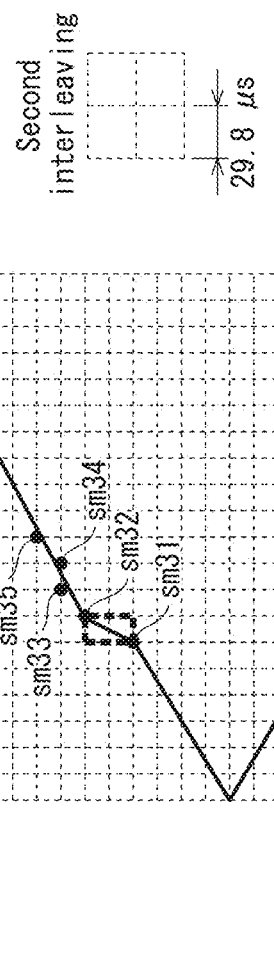
FIG. 6D illustrates interleaving in both the time direction and the element array direction.

FIG. 6A, FIG. 6B, FIG. 6C, and FIG. 6D illustrate sampling resolution of shear wave wavefront propagation positions in a case in which interleaving is not performed, and in cases in which time direction interleaving, element array direction interleaving, or element array-time direction interleaving is performed. FIG. 6A illustrates resolution for sampling shear wave wavefront propagation positions in a case in which interleaving is not performed. FIG. 6B illustrates resolution for sampling shear wave wavefront propagation positions in a case in which time direction interleaving is performed. FIG. 6C illustrates resolution for sampling shear wave wavefront propagation positions in a case in which element array direction interleaving is performed. FIG. 6D illustrates resolution for sampling shear wave wavefront propagation positions in a case in which element array-time direction interleaving is performed. In FIG. 6A, FIG. 6B, FIG. 6C, and FIG. 6D, the horizontal axis is the time direction and the vertical axis is the element array direction. Size of a grid in the time direction and the vertical axis direction indicates a unit of time and a unit amount, respectively. The bold dashed line frame in each of FIG. 6A, FIG. 6B, FIG. 6C, and FIG. 6D encloses the localized increase section of SWS. The smaller the range enclosed by the bold dashed line frame, the greater the time resolution/spatial resolution. In FIG. 6A, the localized increase section is represented by a two-by-two area of the grid. In FIG. 6B, the localized increase section is represented by a one-by-one area of the grid, showing an increase in accuracy. In FIG. 6C, the localized increase section is represented by a one-by-three area of the grid, showing an increase in accuracy. In FIG. 6D, the localized increase section is represented by a one-by-one area of the grid and size of each grid is reduced, and therefore speed increase in the localized increase section is represented in further detail.

In FIG. 6A, sm1, sm2, sm3, sm4, and sm5 indicate sampling points when acquiring tissue state in an ROI at resolution of a non-interleaving scheme. Of these sampling points, even the sampling points closest to the localized increase section (sm1, sm2) do not acquire two points in the localized increase section pd2, and therefore shear wave speed when passing through hard tissue cannot be accurately calculated. Because change amount and time interval of shear wave position in a change portion cv1 are not accurately represented, even if acoustic element intervals are divided by frame time intervals, shear wave speed is greatly different.

In FIG. 6B, sm11, sm12, sm13, sm14, and sm15 indicate sampling points acquired at resolution of a time direction interleaving scheme. Of these sampling points, the sampling points sm11 and sm12 correctly acquire a start point and end point of the localized increase section pd2, and therefore shear wave speed when passing through hard tissue can be accurately calculated. Accordingly, in the time direction interleaving of FIG. 6B, intervals in the element array direction are wider than a change portion, but width of the grid in the time direction is shorter. Accordingly, in time direction interleaving, accuracy of shear wave speed, obtained by calculation of wavefront position change amount/frame time interval, is higher than that of a non-interleaving scheme.

In FIG. 6C, sm21, sm22, sm23, sm24, and sm25 indicate sampling points acquired at resolution of a sampling rate of element array direction interleaving. Of these sampling points, sampling point sm21 uses the start point of the localized increase section, but sm22 is not correctly plotted at the end point of the localized increase section pd2. However, in element array-time direction interleaving, three unit amounts are measured as displacement amounts in the element array direction of the period included in the localized increase section, and therefore accuracy of displacement amounts of the wavefront is increased in comparison to the non-interleaving scheme of FIG. 6A. Accordingly, in element array direction interleaving, shear wave speed obtained by v=change amount of wavefront displacement in element array direction/frame time interval is increased in accuracy when compared to a non-interleaving scheme, because spatial resolution in the element array direction increases.

In FIG. 6D, sm31, sm32, sm33, sm34, and sm35 indicate sampling points plotted at a resolution of element array-time direction interleaving. These sampling points are correctly plotted at the start point and end point of the localized increase section pd2, and therefore shear wave speed when passing through hard tissue can be accurately calculated. In the element array-time direction interleaving of FIG. 6D, grid width and height is less than width and height of the localized increase section, and therefore shear wave speed accuracy obtained by calculating v=change amount of wavefront displacement in element array direction/frame time interval is high.

Figure 6F:
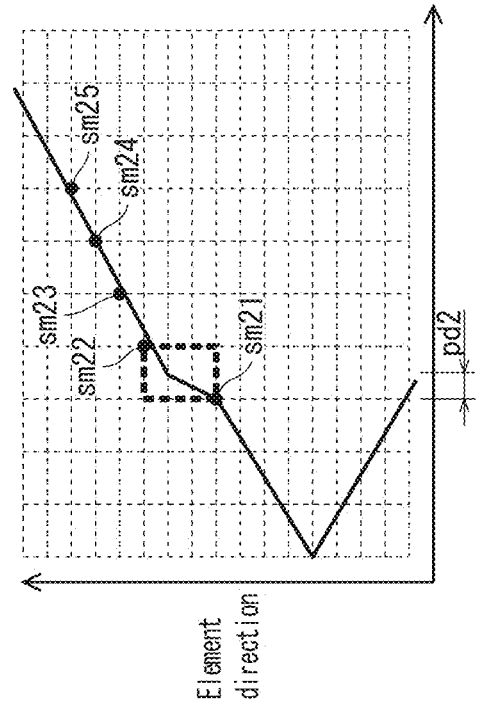
FIG. 6F illustrates frame intervals after a second interleaving.

FIG. 6E illustrates how frame time intervals are shortened by interleaving once. The largest frame time interval illustrated in FIG. 6E is 100 µs. In contrast, the smaller frame time interval illustrated in FIG. 6E is 50 µs to 75 µs. FIG. 6F illustrates frame time intervals obtained by interleaving twice. FIG. 6F illustrates that the frame time intervals obtained by interleaving twice are shortened to 29.8 µs.

When executing time direction interleaving, the technical problem caused by low time resolution is eliminated, and when executing element array direction interleaving, the technical problem caused by low spatial resolution is eliminated. When executing element array-time direction interleaving, the technical problems caused by both low time resolution and low spatial resolution are eliminated. Eliminating the technical problems caused by both low time resolution and low spatial resolution is not essential to the present disclosure. Eliminating the technical problem caused by either low time resolution or low spatial resolution is sufficient.

(Details of Time Direction Interleaving)

The following describes details of operation of the elements of the ultrasound processing device 101 when time direction interleaving is performed.

Figure 7:
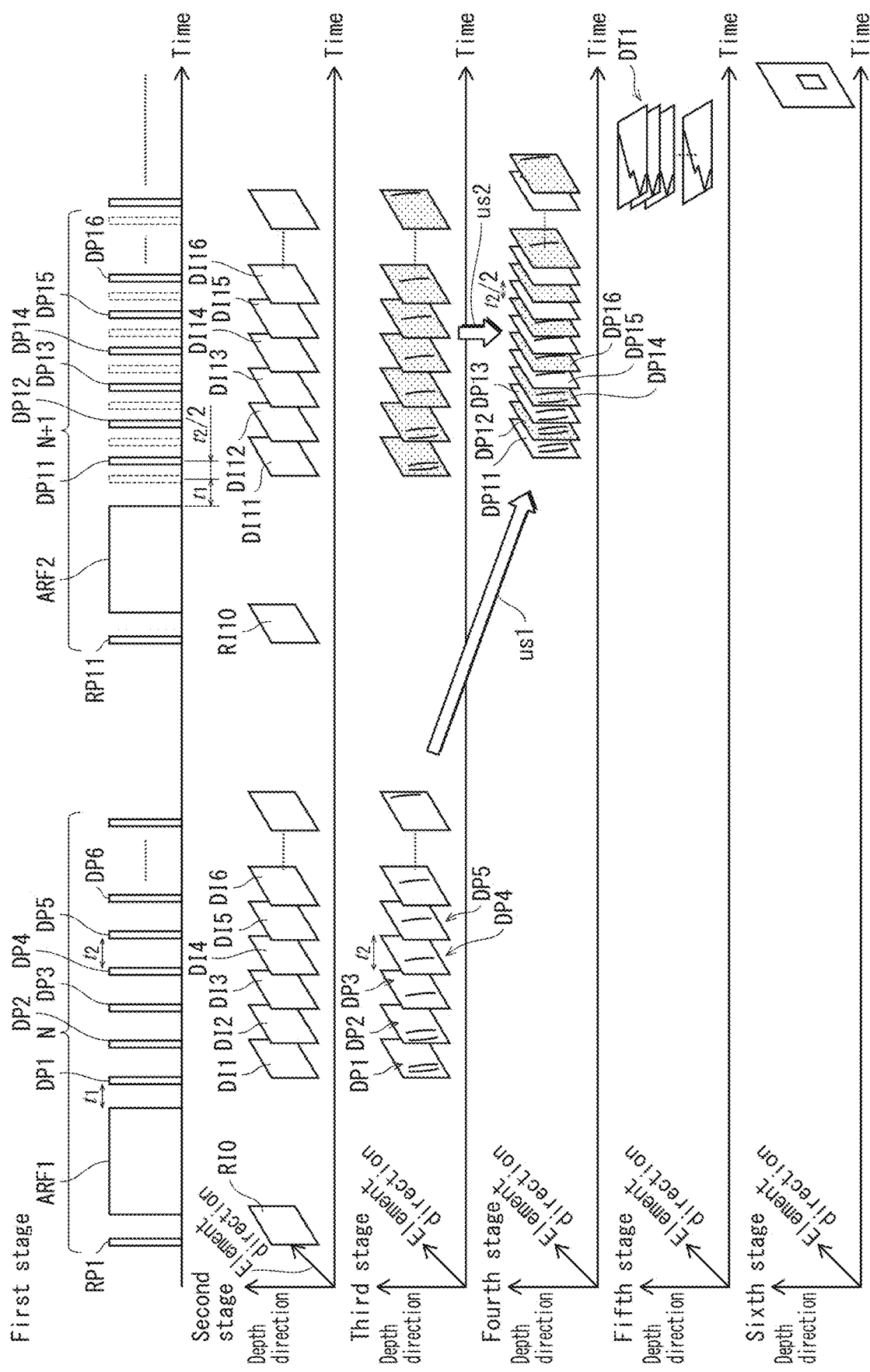
FIG. 7 is a timing chart illustrating processing from shear wave excitation to elastic modulus calculation.

FIG. 7 is a timing chart illustrating processing from shear wave excitation to elastic modulus calculation. First, an N-th SW tracking step is described.

The first stage in FIG. 7 illustrates an example of ultrasound transmitted by the push pulse controller 1 and the reference/detection wave transmitter 2 in an N-th SW tracking step. As illustrated in this first stage, ultrasound transmitted in the N-th SW tracking step comprises focused ultrasound (ARF1), a reference detection pulse (RP1) prior to the focused ultrasound, and subsequent detection pulses (DP1, DP2, DP3, DP4, DP5, . . . ).

In stage 2 of FIG. 7, a sequence of DAS data generated by the output data generator 3 in the N-th SW tracking step of stage 1 is illustrated. This DAS data sequence comprises reference DAS data (RIO) obtained by performing beamforming with respect to reflected ultrasound of the reference detection pulse, and detection DAS data (DI1, DI2, DI3, DI4, DI5, . . . ) obtained by performing beamforming with respect to reflected ultrasound of detection pulses. Because the reference DAS data and the detection DAS data are based on the reference detection pulse and the detection pulses, timing of creation of the reference DAS data and the detection DAS data is slightly later than respective timing of transmission of the reference detection pulse and timing of transmission of the detection pulses along the time axis.

The third stage in FIG. 7 illustrates an SWS sequence N comprising wavefront frame data DP1, DP2, DP3, DP4, DP5, . . . , obtained by the displacement detector 8 extracting a shear wave wavefront from detection DAS data, based on the reference DAS data of stage 2. This wavefront frame data is based on detection DAS data, and therefore timing of creation of the wavefront frame data is slightly later than respective timing of creation of detection DAS data.

This concludes description of the N-th SW tracking step. The following describes an (N+1)-th SW tracking step.

In the first stage, ultrasound transmitted by the push pulse controller 1 and the reference/detection pulse transmitter 2 in the (N+1)-th SW tracking step comprises focused ultrasound (ARF2), a reference detection pulse (RP11) prior to the focused ultrasound, and subsequent detection pulses (DP11, DP12, DP13, DP14, DP15, . . . ).

The second step illustrates a DAS data sequence of the (N+1)-th SW tracking step generated by the output data generator 3. This DAS data sequence comprises reference DAS data (RI10) obtained by performing beamforming with respect to reflected ultrasound of the reference detection pulse, and detection DAS data (DI11, DI12, DI13, DI14, DI15, . . . ) obtained by performing beamforming with respect to reflected ultrasound of detection pulses. Based on this data, an SWS sequence N+1 is obtained corresponding to the (N+1)-th SW tracking step.

Differences between the (N+1)-th SW tracking step and the N-th tracking step are as follows.

First, a frame time interval between the transmission of focused ultrasound and transmission of a first detection pulse illustrated in stage 1 is different. Transmission timing of a first detection pulse in the N-th SW tracking step is time $t_1$ from transmission of focused ultrasound, whereas transmission timing of a first detection pulse in the (N+1)-th SW tracking step has a time direction offset ($t_2/2$), and therefore transmission timing of the first detection pulse in the (N+1)-th SW tracking step is time $t_1'$ ($t_1+t_2/2$) from transmission of focused ultrasound. However, a time interval $t_2$ between the first detection pulse and a second detection pulse is the same in the N-th SW tracking and the (N+1)-th SW tracking step.

Second, processing after creation of wavefront frame data is different. The N-th SW tracking step comprises processing until SWS sequence in stage 3, whereas the (N+1)-th tracking step comprises further interleaving and creation of an elastic modulus image. In the (N+1)-th SW tracking step, the SWS sequence N is used in creation of wavefront frame data, as illustrated in stage 4 of FIG. 7, and the displacement interleaver 10 executes time direction interleaving with the SWS sequence N+1. According to this time direction interleaving, frame time intervals of the SWS sequence are reduced to $t_2/2$.

Stage 5 of FIG. 7 illustrates displacement propagation data DT1 obtained based on the wavefront frame data of stage 4. The wavefront frame data is based on a plurality of wavefront frame data in a SWS sequence, and therefore timing of creation of the displacement propagation data DT1 is slightly later than a time of creation of a last component of wavefront frame data in the SWS sequence. Stage 6 in FIG. 7 illustrates generation of output data. Output data generation is based on displacement propagation data DT1, and therefore output data generation is slightly later than displacement propagation data generation.

In the present embodiment, wavefront frame data based on differences between reference DAS data and detection DAS data is interleaved. This is to make propagation of a shear wave in the element array direction clear, in order to improve time resolution by interleaving. In other words, reference DAS data is generated based on reflected ultrasound of a reference detection pulse transmitted when radiation force is not present, and detection wavefront frame data is generated from differences between the reference DAS data and detection DAS data, and therefore the wavefront frame data obtained in the N-th SW tracking step and the wavefront frame data obtained in the (N+1)-th SW tracking step clearly indicate propagation of shear waves along the element array direction. Time direction interleaving alternates these sets of wavefront frame data, and therefore increases time resolution and movement of a shear wave can be more accurately calculated.

The following describes how shear wave movement is derived from the time direction interleaving described above.

Figure 8:
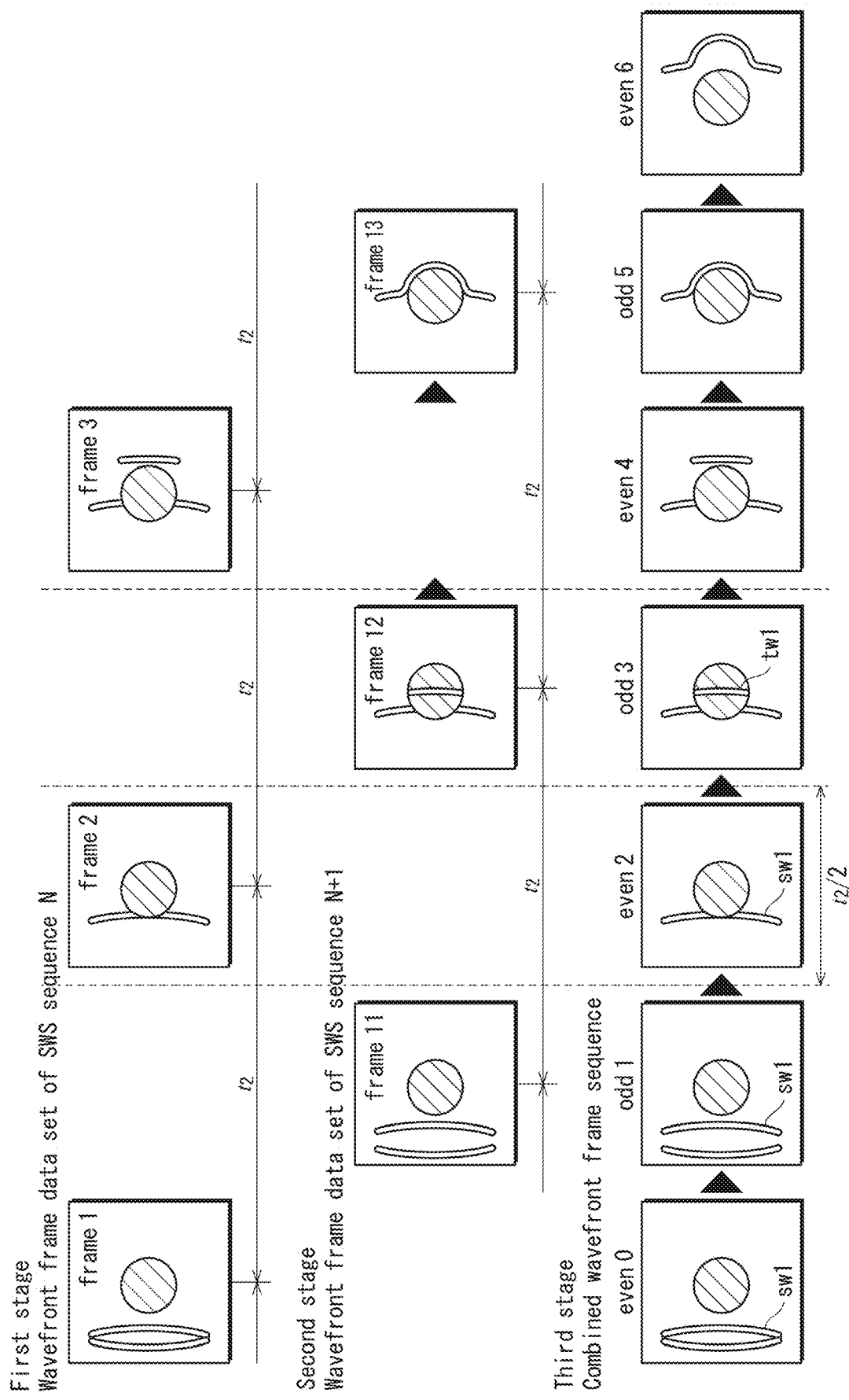
FIG. 8 illustrates how movement of a shear wave is transmitted.

FIG. 8 illustrates how movement of a shear wave is transmitted. Stage 1 of FIG. 8 illustrates a shear wave wavefront that can be drawn from wavefront frame data of SWS sequence N. The frames illustrated in stage 1 are frame 1, when the shear wave has yet to arrive at hard tissue, frame 2, when the shear wave arrives at the hard tissue, and the instant a transmitted wave is generated, and frame 3, when the transmitted wave has exited the hard tissue.

Stage 2 of FIG. 8 illustrates movement of a shear wave derived from wavefront frame data of SWS sequence N+1. The frames that can be drawn from the wavefront frame data of SWS sequence N+1 are frame 11, when the shear wave has yet to arrive at the hard tissue, frame 12, when the transmitted wave that has separated from the shear wave is passing through the hard tissue, and frame 13, when the transmitted wave has exited the hard tissue. Wavefront frame data of SWS sequence N+1 does not capture a start point or end point of a period in which the shear wave passes through the hard tissue, and therefore achieving a high accuracy of elastic modulus is difficult when such frames are used to calculate speed.

Stage 3 in FIG. 8 illustrates a shear wave wavefront derived from a combined wavefront frame sequence. In the combined wavefront frame sequence, frames from SWS sequence N are even frames and frames from SWS sequence N+1 are odd frames, and therefore frames from SWS sequence N and frames from SWS sequence N+1 alternate over time. The following describes movement of a shear wave indicated by the wavefront frame data of the even frames and the odd frames (even0, odd1, . . . , odd5, and even6). When hardness of tissue is substantially constant, propagation speed of a shear wave is substantially constant, and therefore shape of a shear wave SW1 propagates without substantially changing (even0, odd1). When the shear wave arrives at a surface of the hard tissue (even2), the transmitted wave tw1 progresses through the interior of the hard tissue (odd3). In FIG. 8, the hard tissue is round, and distances the wavefront travels through the hard tissue vary, and therefore the wavefront of the transmitted wave forms a convex shape in the direction of travel. As long as the shear wave and the transmitted wave proceed outside the hard tissue (even4), propagation speed of the shear wave is constant, and maintains a constant shape (odd5, even6)

From FIG. 8, the following can be understood. In SWS sequence N of stage 1 and SWS sequence N+1 of stage 2, the start and end points, or at least one of the start point and the end point of a change portion of shear wave speed are outside a plotted grid, and therefore when seeking speed of the shear wave at a time resolution and a spatial resolution of the grid, achieving a high accuracy for speed of the shear wave is difficult. However, in the combined wavefront frame sequence of stage 3, at least two of a time of arrival at the hard tissue, a time of passing through the hard tissue, and a time of exiting the hard tissue are defined on a time axis, and with this information speed of the shear wave can be calculated with high accuracy.

(PRT Setting)

Figure 9:
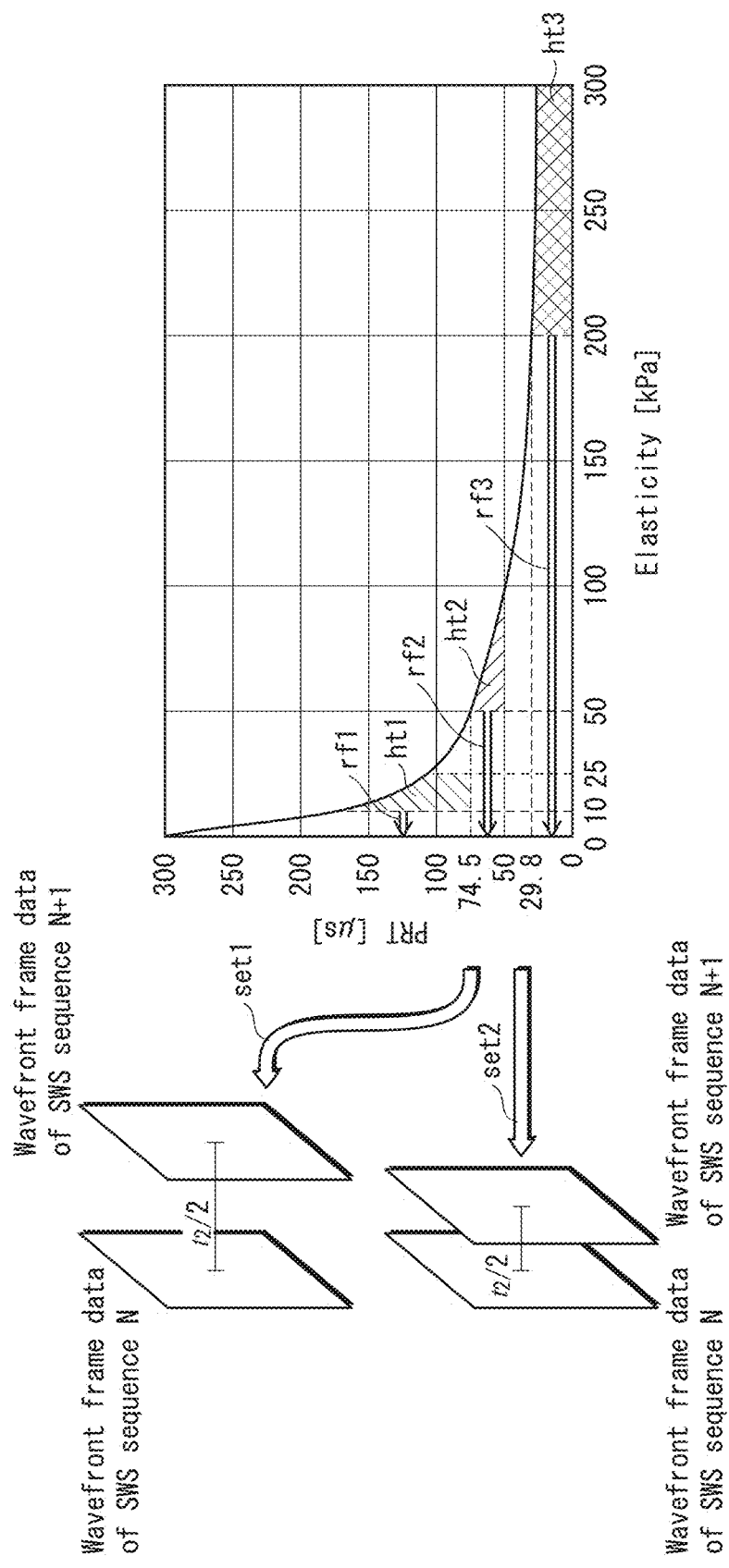
FIG. 9 illustrates an elastic modulus characteristic curve showing elastic modulus changes when the horizontal axis is elasticity and the vertical axis is pulse repeat time (PRT)

PRT, which defines the frame time interval of the combined wavefront frame sequence, is defined based on a numerical range of an elastic modulus characteristic curve. FIG. 9 illustrates an elastic modulus characteristic curve showing elastic modulus changes when the horizontal axis is elasticity and the vertical axis is PRT. In the graph in FIG. 9, PRT is very high in a range of low elasticity, and as elasticity increases, PRT decreases. Specifically, in a range of 10 kPa to 25 kPa marked by hatching ht1, PRT is 74.5 µs to 150 µs; in a range of 50 kPa to 100 kPa marked by hatching ht2, PRT is 50 µs to 74.5 µs; and in a range of 200 kPa to 300 kPa marked by hatching ht3, PRT is 0 µs to 29.8 µs. The sign rf1 indicates a reference of an elastic modulus characteristic curve for guiding PRT corresponding to an elastic modulus numerical range of 10 kPa to 25 kPa, and rf2 indicates a reference of an elastic modulus characteristic curve for guiding PRT corresponding to an elastic modulus numerical range of 50 kPa to 75 kPa. The sign rf3 indicates a reference of an elastic modulus characteristic curve for guiding PRT corresponding to an elastic modulus numerical range of 200 kPa to 300 kPa.

The sign set1 indicates a setting of frame time interval when elastic modulus is 10 kPa to 25 kPa. The sign set2 indicates a setting of frame time interval when elastic modulus is 50 kPa to 100 kPa. By selecting a frame time interval corresponding to a target elastic modulus from the elastic modulus characteristic curve, a time direction offset can be arrived at. This concludes description of time direction interleaving. The following describes details of element array direction interleaving.

In a numerical range, PRT of 50 µs or less is a range for which transmission and reception of ultrasound is impossible, and therefore, in the present embodiment, time direction interleaving shortens the "apparent" PRT. "Apparent" PRT means that frame time interval is decreased by alternating wavefront frame data obtained from two or more SW tracking steps.

When the controller 4 executes an SW tracking step, the controller 4 causes the numerical range of the elastic modulus characteristic curve of FIG. 9 to be displayed on the display 103, and receives selection of a numerical range of elastic modulus. When a numerical range is selected, the controller 4 instructs the displacement interleaver 10 that frame time interval of the combined wavefront frame sequence becomes a PRT corresponding to the elastic modulus of the selected numerical range. Selection of a numerical range of elastic modulus is merely one example, and PRT may be determined according to reception of a selection of a subject for an SW tracking step from a user.

(Details of Element Array Direction Interleaving)

Figure 10:
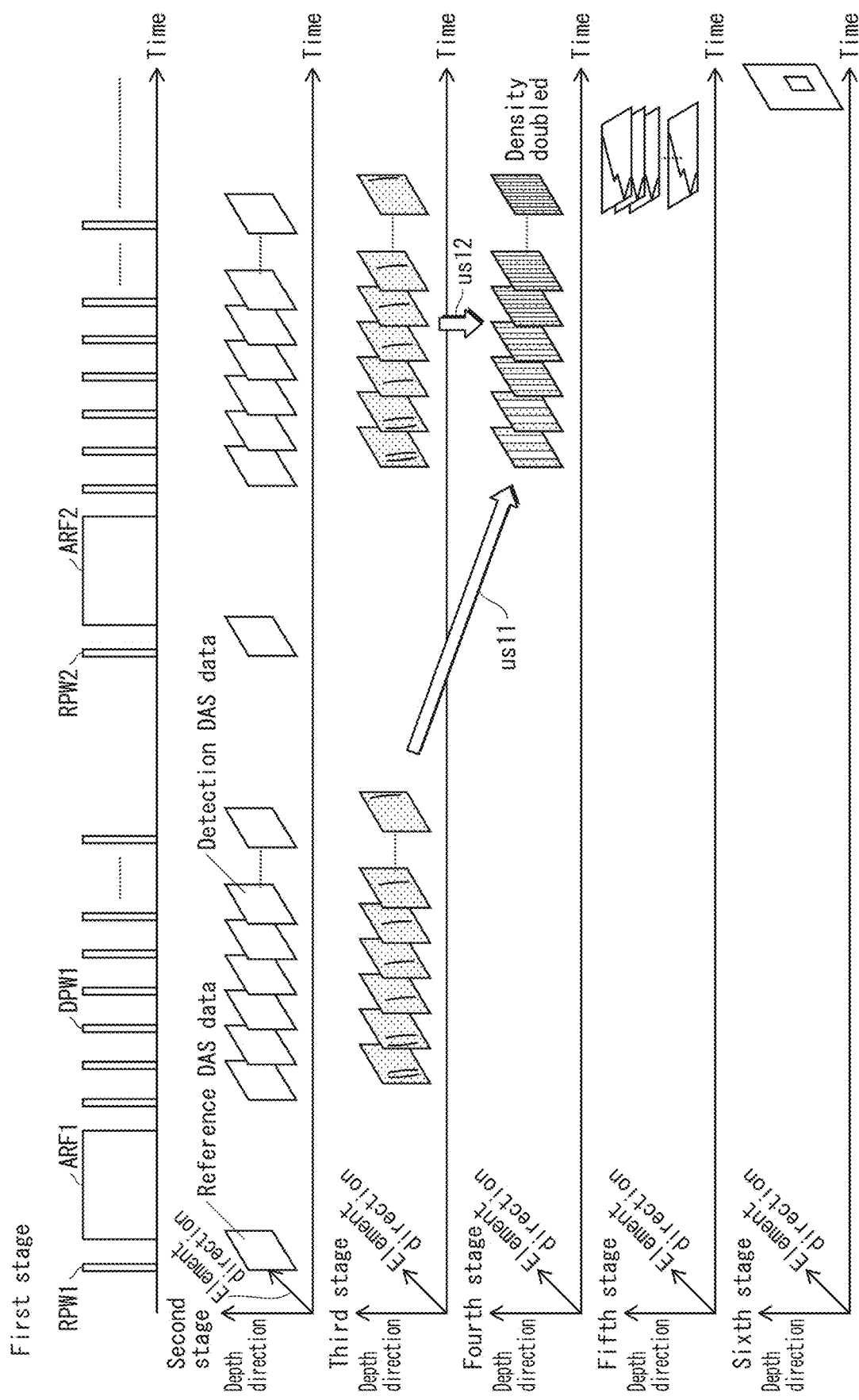
FIG. 10 is a timing chart when interleaving is performed in the element array direction.

FIG. 10 is a timing chart for element array direction interleaving. FIG. 10 is based on FIG. 7, but has the following differences.

First, there is a difference in time offset setting for transmission of the detection pulses. In FIG. 7, $t_2/2$ is specified as a time offset for transmission of the first detection pulse, whereas in FIG. 10, this time offset is not present. Because a time offset does not exist, time resolution does not change.

Second, in FIG. 10, in stage 4, element array direction interleaving is executed by using SWS sequence N with respect to SWS sequence N+1. In this element array direction interleaving, acoustic line density of wavefront frame data in SWS sequence N+1 is doubled. The signs us11 and us12 in FIG. 10 schematically indicate use of SWS sequence N and SWS sequence N+1 in element array direction interleaving. Further, in element array direction interleaving, an element array direction offset is set for delay-and-sum processing. This concludes description of the timing chart for element array direction interleaving.

The following describes delay-and-sum processing according to the reception beam former 6 when element array direction offset is set. FIG. 11A illustrates a process of obtaining an acoustic line signal at one focus point in a region of interest (ROI). The sign ec10 in FIG. 11A indicates reflected ultrasound inputted to acoustic elements from reflected ultrasound at a receive signal focus point. Waveforms wv1, wv2, wv3, and wv4 indicated RF signals outputted from acoustic elements. The sign pf1 indicates a receive delay profile curve with respect to element input signals that are input to the ultrasound processing device 101 from the acoustic elements. The sign pf1 indicates which positions of RF signals are integrated for generation of an acoustic line signal of a vertex position of the receive delay profile curve. The sign sg1 indicates the acoustic line signal generated by delay-and-sum of the receive delay profile. Delay-and-sum according to the receive delay profile is performed at a plurality of positions in the ROI, and therefore acoustic line signals can be obtained at a plurality of positions in the depth direction.

Figure 11B:
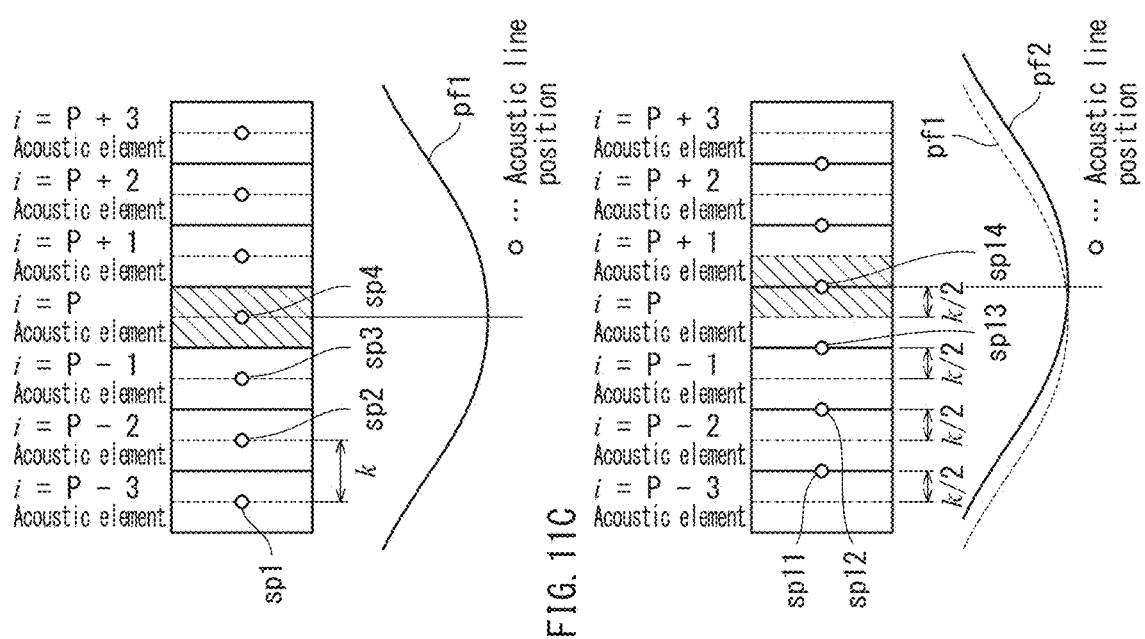
FIG. 11B illustrates acoustic line positions set at a time of delay-and-sum of an N-th shear wave tracking step.
Figure 11C:
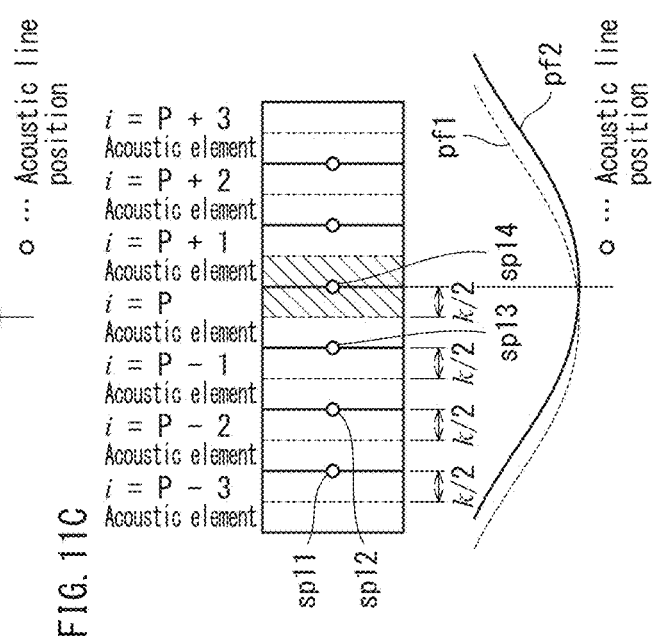
FIG. 11C illustrates acoustic line positions set at a time of delay-and-sum of an (N+1)-th shear wave tracking step.
Figure 11A:
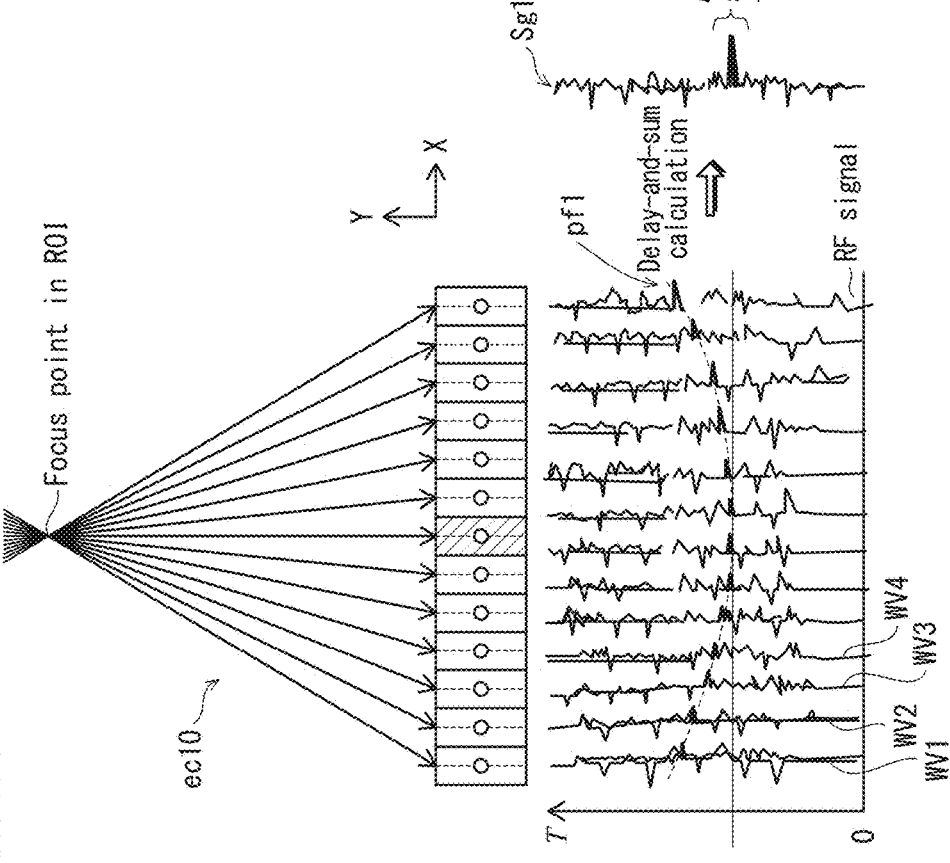
FIG. 11A illustrates a process of obtaining an acoustic line signal at one focus point in a region of interest (ROI)

FIG. 11B illustrates acoustic line positions set at a time of delay-and-sum of an N-th shear wave tracking step. The signs sp1, sp2, sp3, and sp4 indicate acoustic line positions. In FIG. 11B, the acoustic elements indicated by i=P−2, i=P−1, i=P, i=P+1, and i=P+2 are arranged in a line. FIG. 11C illustrates acoustic line positions set at a time of delay-and-sum of an (N+1)-th shear wave tracking step. The signs sp11, sp12, sp13, and sp14 indicate acoustic line positions, and in the (N+1)-th delay-and-sum, the acoustic line positions are set on an extension position between adjacent ones of the acoustic elements. The sign pf2 indicates a receive profile curve generated based on the acoustic line positions set in the (N+1)-th shear wave tracking step. In the (N+1)-th delay-and-sum process, a peak of the receive profile curve is shifted half of the size of an acoustic element in the element array. From the shifting of a maximum point of the curve in the element array direction, phase shift of the acoustic line signal occurs.

Figure 12:
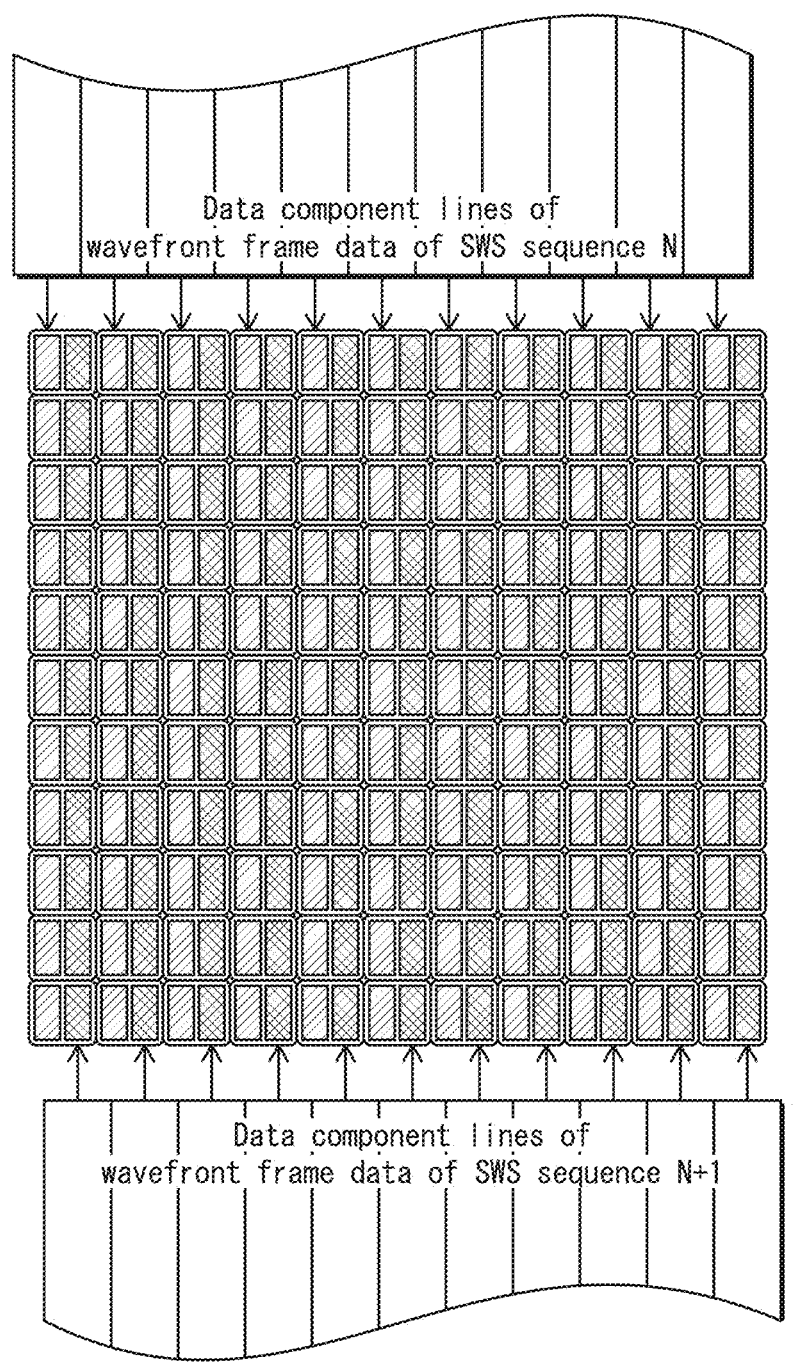
FIG. 12 is an enlargement of wavefront frame data obtained by doubling density.

FIG. 12 illustrates an enlargement of wavefront frame data generated from double-density acoustic lines. The center of FIG. 12 illustrates an arrangement of data components in wavefront frame data obtained by element array direction interleaving. In this arrangement of data components, faint hatching indicates an even line and dense hatching indicates an odd line. According to the process illustrated in FIG. 11A, FIG. 11B, and FIG. 11C, acoustic line positions are set to central positions of acoustic elements, from which a DAS frame is obtained, from which data component lines of wavefront frame data are obtained. These data component lines of wavefront frame data are the even lines of interleaved wavefront frame data.

Data component lines of wavefront frame data based on DAS frames obtained from acoustic line positions set to positions between acoustic elements are the odd lines of the interleaved wavefront frame data. Thus, data components of SWS sequence N and data components of SWS sequence N+1 are arranged in alternating even lines and odd lines, increasing spatial resolution by element array direction interleaving. Note that arranging data components of SWS sequence N and data components of SWS sequence N+1 in alternating even lines and odd lines is merely one example, and data components of SWS sequence N and data components of SWS sequence N+1 may be arranged in alternating odd lines and even lines.

(Interleaving Repetition)

Figure 13A:
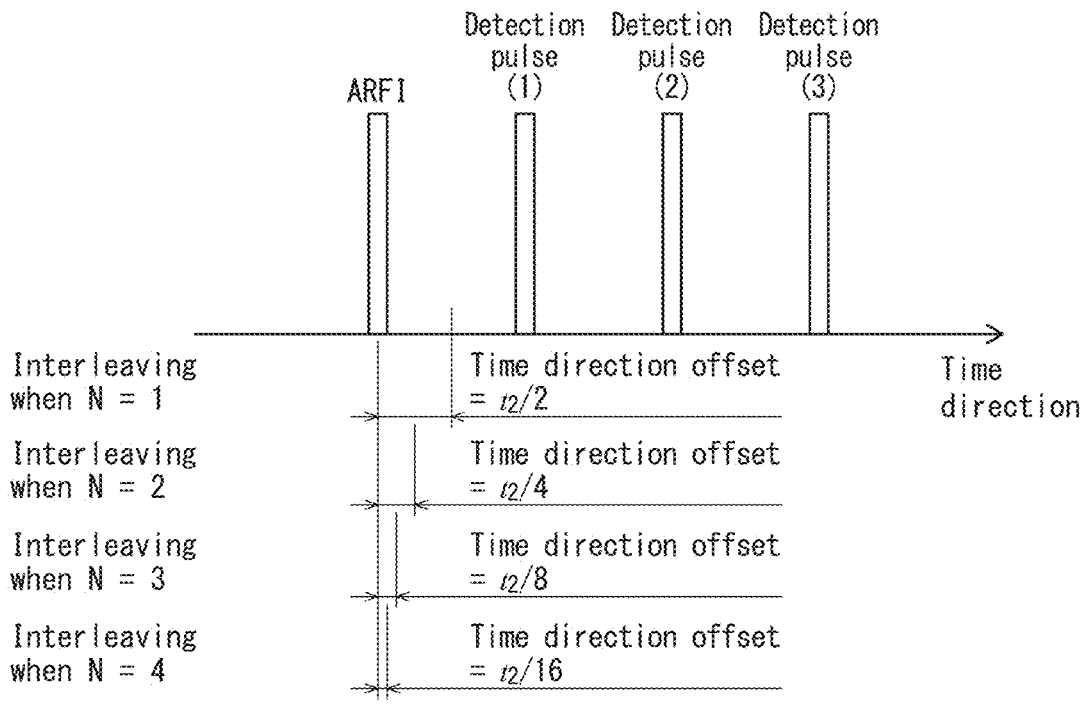
FIG. 13A illustrates setting of time offset when interleaving is repeated multiple times.

FIG. 13A illustrates setting of time offset when interleaving is repeated multiple times. Offset $t_2/2$ is a time offset set for a first interleaving, and is the same as illustrated in FIG. 7. Offset $t_2/4$ is a time offset for a second interleaving, $t_2/8$ is a time offset for a third interleaving, and $t_2/16$ is a time offset for a fourth interleaving. Thus, a u-th interleaving is set to a time direction offset $t_2/(2$ to the power u).

Figure 13B:
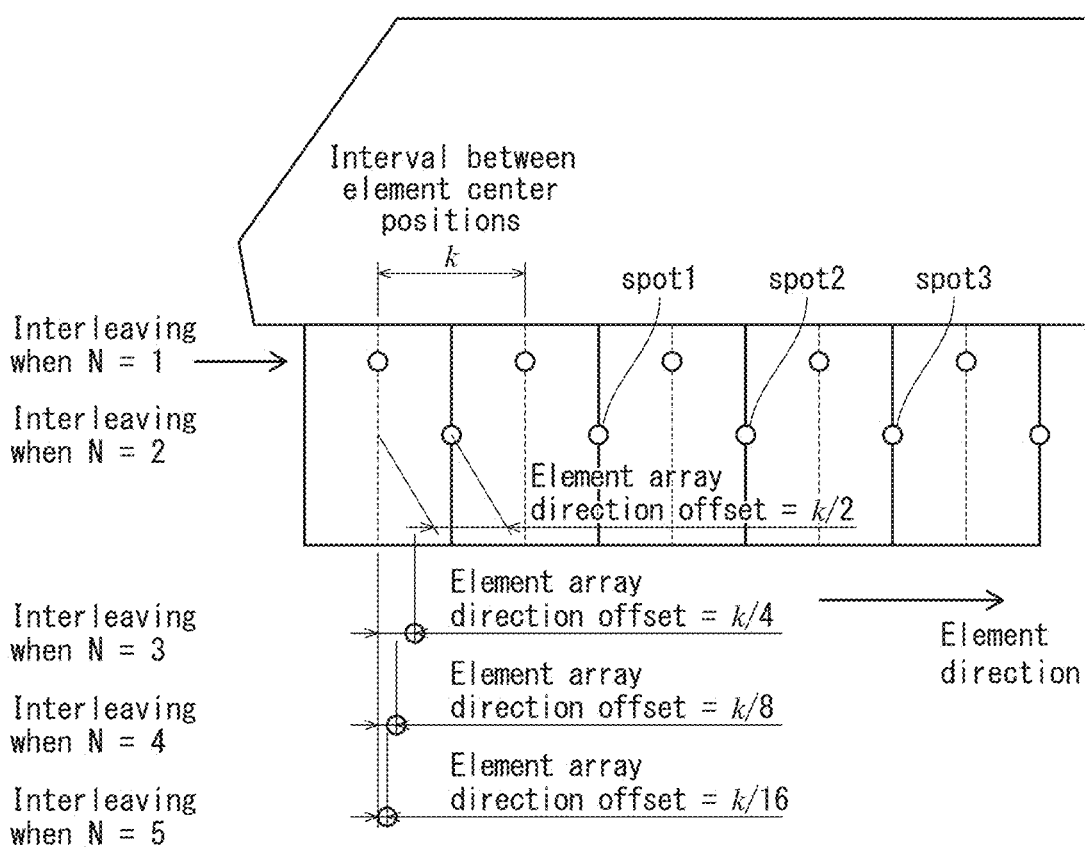
FIG. 13B illustrates element direction offset to be set when interleaving in the element array direction is repeated.

FIG. 13B illustrates element direction offset to be set when interleaving in the element array direction is repeated. Element direction offset indicates an amount of shift of acoustic line positions in the element direction. The signs spot1, spot2, and spot3 indicate central positions of elements, and are initial positions of acoustic line positions. The sign k indicates an interval between the central position of an element and the central position of an adjacent element. The sign k/2 indicates an element array offset for a first interleaving. The sign k/4 indicates an element array offset for a second interleaving, k/8 indicates an element array offset for a third interleaving, and k/16 indicates an element array offset for a fourth interleaving. Thus, a u-th interleaving is set to an elemental array offset k/(2 to the power u). By repeating interleaving, the time direction offset and element direction offset become smaller, and intervals in the time direction and element array direction become smaller. Time direction interleaving, element array direction interleaving, or time direction and element array direction interleaving may be executed, and resolution in the element array direction and depth direction may be altered freely.

This concludes description of time direction interleaving and element array direction interleaving.

(Calculation of Locally Increased Shear Wave Speed)

The following describes a detailed process for calculating locally increased shear wave speed due to passing through hard tissue.

[Math 2]

$$E(i, j) = 3v(i, j)^2 \quad \text{(Equation 3)}$$

$$v(i, j) = \frac{k}{(\tau T)} \quad \text{(Equation 4)}$$

$$\tau = l \cdot \max\{R_{fg}\} \quad \text{(Equation 5)}$$

$$R_{fg}(l) = \frac{C_{fg}}{\sqrt{C_{ff}} \sqrt{C_{gg}}} \quad \text{(Equation 6)}$$

$$C_{fg}(l) = \frac{1}{n-m} \sum_{t=1}^{n-m} \tilde{f}_i(t) \cdot \tilde{g}_{i+1}(t+l) \quad \text{(Equation 7)}$$

$$(l = 1, 2, 3, \ldots, m)$$

Equation 3 is for calculating elastic modulus E(i,j). Here, v(i,j) indicates speed of a shear wave that has been locally increased. By squaring v(i,j) and multiplying by three, the elastic modulus E(i,j) can be derived. Equation 4 is for calculating shear wave speed in a change portion. As indicated in Equation 4, shear wave speed v(i,j) can be derived by dividing an acoustic element interval k by a time interval τT in which shift occurs. The shift amount τ in τT is defined by a displacement amount l between element position i and element position i+1 indicating how far the shear wave wavefront shifts in the time direction. Equation 5 indicates calculation for deriving the shift amount τ from correlation coefficient of $f_i(t)$ and $g_{+i+1}(t)$. The function max {$R_{fg}$} derives a maximum from a plurality of correlation coefficients. The shift amount τ is calculated by multiplying max {$R_{fg}$} by the shift amount l. Equation 6 indicates calculation of correlation coefficient normalization. In equation 6, a correlation coefficient $C_{fg}$ of $f_i(t)$ and $g_{i+1}(t)$ is divided by the square root of the autocorrelation value of $f_i(t)$ (defined as $C_{ff}$) and the square root of the autocorrelation value of $g_{i+1}(t)$ (defined as $C_{gg}$). In equation 7, $f_i(t)$, and $g_{i+1}(t+l)$ indicate correlation values of $f_i(t)$, and $g_{i+1}(t+l)$ at given times. By calculating these correlation values for all points on a time axis, and performing a product sum operation, $C_{fg}$ is a value for all displacement propagation data at a given depth position.

Figures 14B, 14C, 14D:
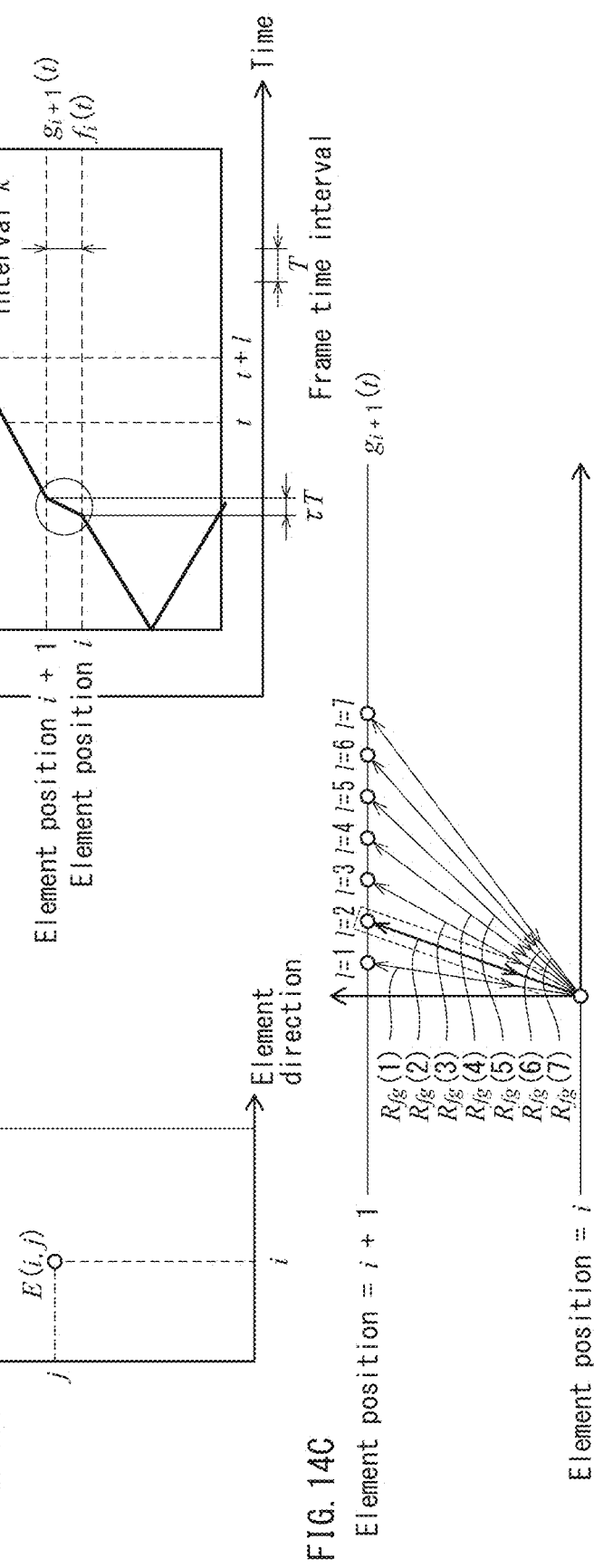
FIG. 14B illustrates displacement propagation data including a frame time interval with distortion.
FIG. 14C illustrates a derivation process for deriving a shift amount l in a time direction.
FIG. 14D illustrates a calculation process for calculating $C_{fg}$.

FIG. 14A illustrates a position that is the subject of elastic modulus E(i,j). FIG. 14B illustrates displacement propagation data including a frame time interval with distortion. Here, τT is a time interval of a change portion in which distortion occurs. Here, $f_i(t)$ indicates a change amount of a wavefront position in the time direction at element position (i), and $g_{i+1}(t)$ indicates a change amount of a wavefront position in the time direction at element position (i+1). In FIG. 14C, l=1, l=2, l=3, l=4, . . . indicate values in the time direction of the element position i+1. In FIG. 14C, $R_{fg}(1)$, $R_{fg}(2)$, $R_{fg}(3)$, $R_{fg}(4)$, . . . indicate normalized correlation coefficient of $f_i(t)$ and $g_{i+1}(t)$ when l is set to values of 1, 2, 3, 4, . . . . As can be understood from FIG. 14C, as the value of l increases, tilt and length of a straight line joining $f_i(t)$ and $g_{i+1}(t)$ increases. Value of $R_{fg}$ indicates change in length and tilt according to different values of l. In FIG. 14C, tilt when l is exactly 2 matches tilt of the change portion, and in calculation of l×max{$R_{fg}$}, this l=2 is derived, surrounded by the dashed line.

FIG. 14D illustrates a calculation process for calculating $C_{fg}$. The signs c11, c12, c13, c14, and c15 schematically indicate correlation of $f_i(t)$ and $g_{i+1}(t+l)$ when t=1, 2, 3, 4, and 5.

In the present embodiment, time intervals, which are a basis for shear wave speed calculation and a basis for correlation value calculation, are shortened by interleaving, and therefore accuracy of localized shear wave speed calculation is increased.

(Flowchart Implementation)

Processing of elements of the ultrasound processing device 101 can be generalized as processing steps of hardware resources according to various external events and internal parameters of the device. This generalization of processing steps is illustrated in the flowcharts of FIG. 15, FIG. 16, FIG. 17, and FIG. 18.

Figure 15:
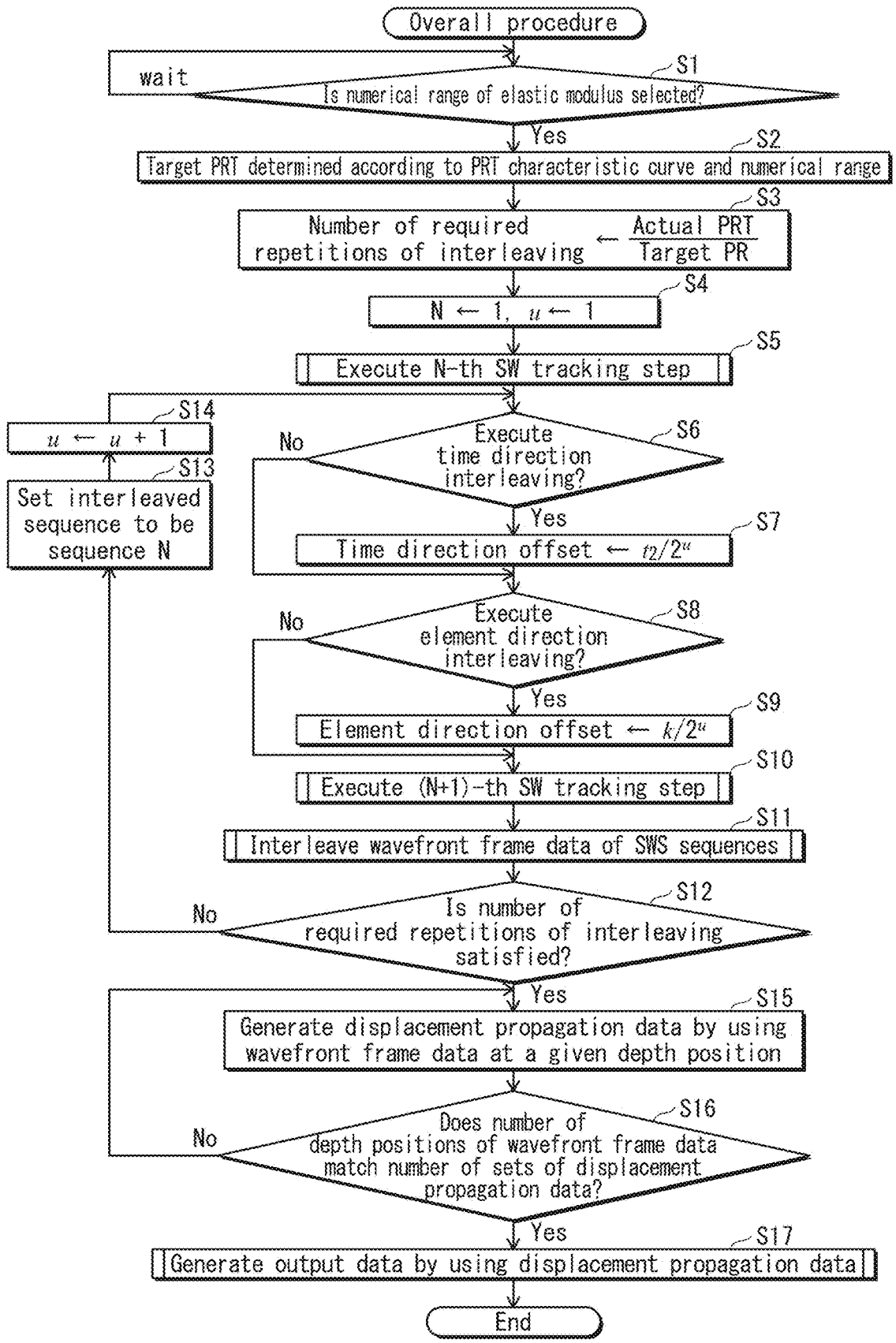
FIG. 15 is a flowchart illustrating an overall control procedure according to the ultrasound processing device 101.

At the top of the processing hierarchy comprising the flowcharts of FIG. 15, FIG. 16, FIG. 17, and FIG. 18 is the flowchart of FIG. 15. FIG. 15 is a flowchart illustrating an overall control procedure according to the ultrasound processing device 101. The following describes the flowchart of FIG. 15. In the flowchart of FIG. 15, first, a selection of a numerical range of elastic modulus is received from a user (step S1). When a numerical range is selected, a target PRT is determined according to PRT characteristic curve and the numerical range selected (step S2), and the number of required repetitions of interleaving is determined by calculation of actual PRT/target PRT (step S3). Subsequently, a variable N indicating a number of transmissions of focused ultrasound and a counter variable u indicating a number of times interleaving are both initialized to one (step S4), an N-th SW tracking step is executed (step S5), and subsequently initial setting is performed in steps S6, S7, S8, and S9. Here, the time direction offset and element array direction offset are set to zero. Thus, the time direction offset and the element array direction offset are set to significant values in steps S5 through S9.

Initial settings comprise steps of determining whether or not time direction interleaving is to be executed (step S6), and when time direction interleaving is to be executed, setting the time direction offset to a value of $t_2/(2$ to the power u) (step S7); determining whether or not element array direction interleaving is to be executed (step S8), and when element array direction interleaving is to be executed, setting the element array direction interleaving to a value of k/(2 to the power u) (step S9).

Subsequently, an SW tracking step is performed that relies on an (N+1)-th ARFI transmission (step S10), and interleaving of SWS sequence N and SWS sequence N+1 is executed (step S11). In step S12, whether or not interleaving has been executed the required number of times is determined. When the number of times interleaving does not satisfy the required number of times ("No" in step S12), a frame group of sequence N+1 is set to be a frame group of sequence N (step S13), variable u is incremented (step S14), and processing returns to step S6. When the required number of times interleaving has been executed ("Yes" in step S12), displacement propagation data is generated by using wavefront frame data at a given depth position in step S15. In step S16, whether or not the number of depth positions of wavefront frame data matches the number of displacement propagation data sets is determined. In the case of a match, processing proceeds to step S17, and an elastic modulus image is created by using the displacement propagation data.

Figure 16:
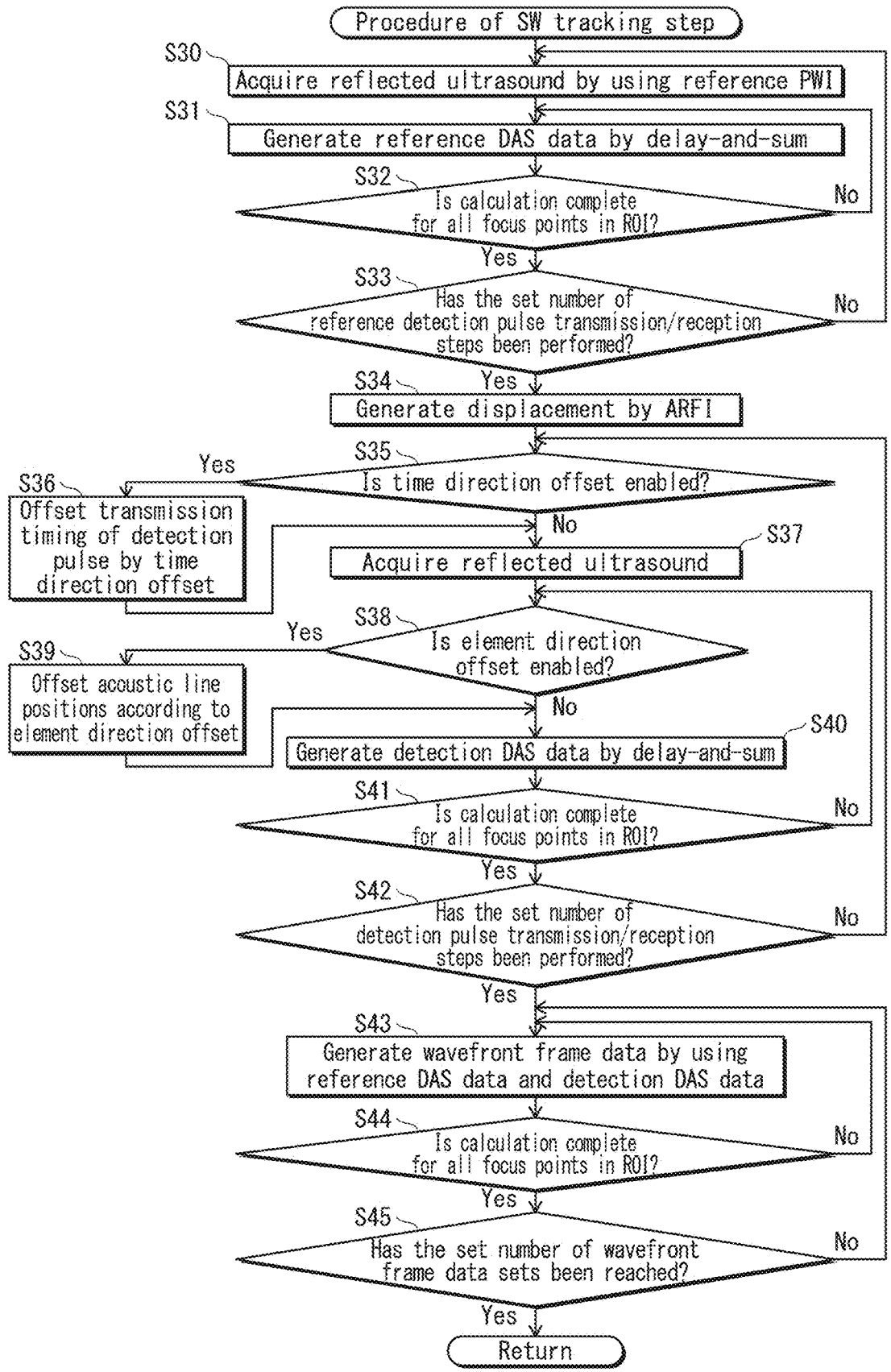
FIG. 16 is a flowchart illustrating a detailed procedure of a shear wave tracking step.

The shear wave (SW) tracking step of step S5 and step S10 can be expanded to a more detailed procedure as a subroutine. FIG. 16 is a flowchart illustrating a detailed procedure of an SW tracking step. The flowchart of FIG. 16 is called from execution of an N-th SW tracking step (step S5) and execution of an (N+1)-th SW tracking step (step S10).

First, a reference detection pulse is transmitted and reflected ultrasound received (step S30), delay-and-sum is performed and reference DAS data is generated (step S31). Step S32 is determination of whether processing has been performed for all focus points in the ROI, and when an unprocessed focus point remains, processing returns to step S31. When an unprocessed focus point is not present, whether or not a required number of transmission and reception steps has been performed is determined in step S33. When the required number of transmission and reception steps has not been performed, processing returns to step S30. When the required number of transmission and reception steps has been performed, ARFI transmission is executed in step S34.

In step S35, it is determined whether or not a time direction offset is enabled. When a time direction offset is enabled, transmission of a detection pulse is offset by a time interval set by the time direction offset in step S36. When a time direction offset is not enabled, step S36 is skipped and processing proceeds to step S37. In step S37, ultrasound signals are acquired.

In step S38, it is determined whether or not an element array direction offset is enabled. When an element array direction offset is enabled, acoustic line positions settings in beamforming are offset by an amount indicated by the element array direction offset in step S39. When an element array direction offset is not enabled, step S39 is skipped. Subsequently, delay-and-sum is performed according to acoustic line positions for which the element array direction offset is set or not set, and detection DAS data for one focus point is acquired (step S40).

The following describes step S36 and step S39 in more detail. "Enabling" a time direction offset or element array direction offset means that the time direction offset or element array direction offset is set to a value other than zero. Specifically, in the flowchart of FIG. 15, time direction offset and element array direction offset are set to zero, and then set to significant values across steps S5 to S9.

The processing of FIG. 16 is called in order to execute an N-th SW tracking step (step S5), which is before initialization of the time direction offset and element array direction offset (steps S6 to S9), and therefore step S35 and step S38 in the flowchart of FIG. 16 result in "No" in each case, transmission timing of a detection pulse and transmission timing of a reference detection pulse are not offset, and acquisition of ultrasound signals from a detection pulse and generation of detection DAS data proceeds (step S37 and step S40).

In contrast, the processing of FIG. 16 is called in order to execute an (N+1)-th SW tracking step (step S10), which is after initialization of the time direction offset and element array direction offset (steps S6 to S9), and therefore one of the time direction offset and the element array direction offset are enabled, and one of step S35 and step S38 in the flowchart of FIG. 16 results in a "Yes". Accordingly, in step S37 and step S40, the transmission timing of a detection pulse is offset, and ultrasound acquisition according to the detection pulse and generation of detection DAS data is performed.

In step S41, whether DAS data has been calculated for all focus points in the ROI is determined, and when DAS data remains to be calculated, step S41 results in a "No", and processing returns to step S38. When no DAS data remains to be calculated, processing proceeds to step S42.

In step S42, whether or not a predefined number of transmission and reception steps has been reached is determined. When the predefined number has not been reached, processing returns to step S35. When the predefined number has been reached, wavefront frame data is generated by using reference DAS data and detection DAS data in step S43. Subsequently, in step S44 it is determined whether or not reference DAS data and detection DAS data has been calculated for all focus points in the ROI. When the result is "No", the target of processing switches to the next focus point and processing returns to step S43. In step S45, it is determined whether or not the number of times wavefront frame data is generated has reached a predefined number. When the predefined number has not been reached, processing returns to step S43. When the predefined number has been reached, the processing of the present flowchart ends, and processing returns to the higher-level routine.

Figure 17:
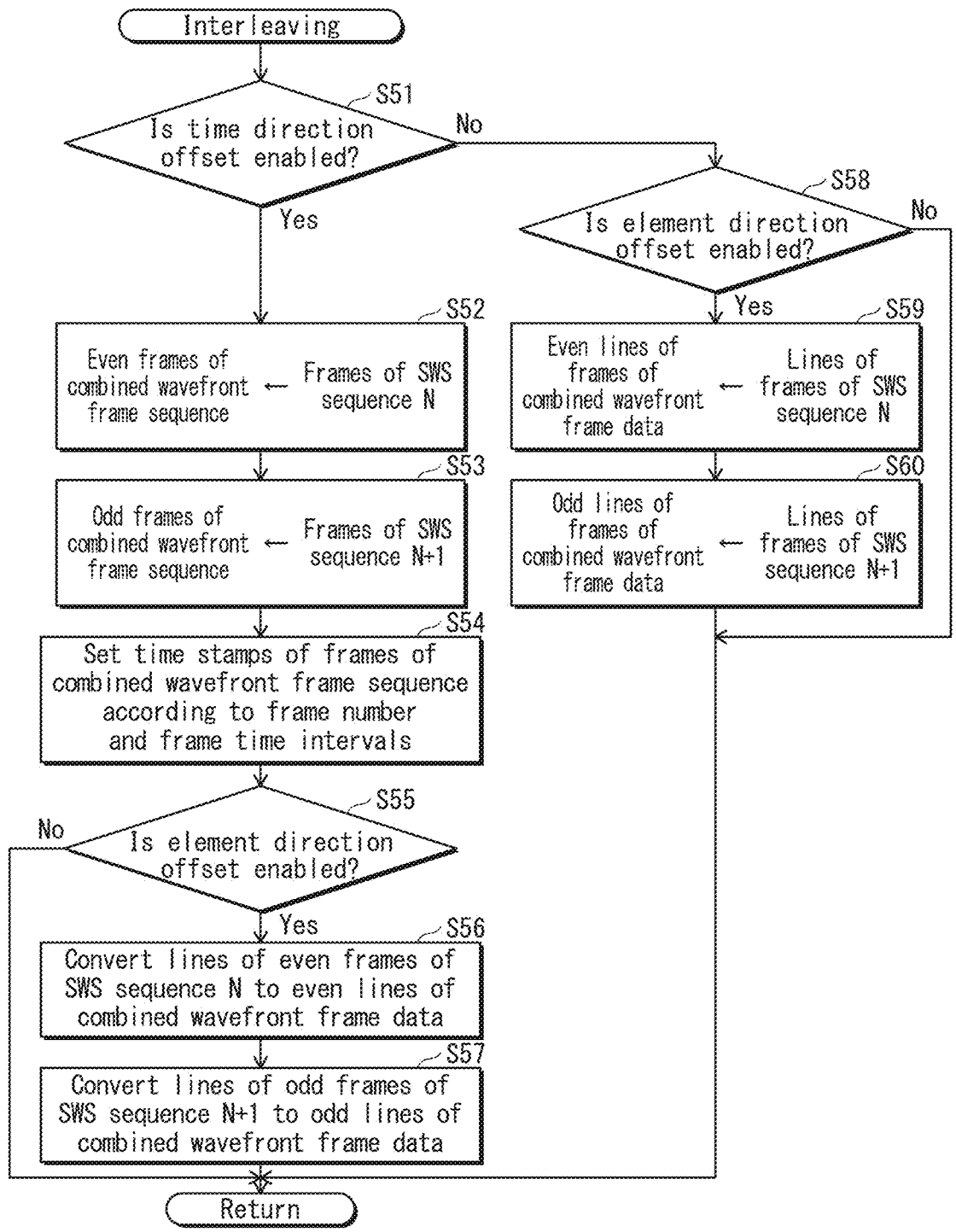
FIG. 17 is a flowchart illustrating details of interleaving.

The interleaving in step S11 of FIG. 15 is also a subroutine, and can be expanded to a more detailed procedure. FIG. 17 is a flowchart illustrating details of interleaving. In step S51, it is determined whether or not a time direction offset is enabled. When a time direction offset is enabled, time direction interleaving is executed in steps S52 to S54. In the time direction interleaving, each frame of SWS sequence N is arranged as even-numbered frames of a combined wavefront frame sequence (step S52), each frame of SWS sequence N+1 is arranged as odd-numbered frames of the combined wavefront frame sequence (step S53), and subsequently time stamps are added to each frame according to frame numbers of even-numbered frames and odd-numbered frames (step S54).

In step S55, it is determined whether or not an element array direction offset is enabled. When element array direction offset is not enabled, the present flowchart ends, and processing returns to a point immediately after the step that called this subroutine. When element array direction offset is enabled, line positions are changed according to step S56 and step S57. Specifically, data component lines in the element array direction of each frame in SWS sequence N are converted to even lines of each frame in combined wavefront frame data (step S56), and data component lines in wavefront frame data of SWS sequence N+1 are converted to odd lines of wavefront frame data in the combined wavefront frame data (step S57).

When time direction offset is not enabled ("No" in step S51), and element array direction offset is enabled ("Yes" in step S58), step S59 and step S60 are performed. Here, data component lines in wavefront frame data of the SWS sequence N are converted to even lines of wavefront frame data in combined wavefront frame data (step S59), and data component lines in wavefront frame data of SWS sequence N+1 are converted to odd lines of wavefront frame data in the combined wavefront frame data (step S60).

Figure 18:
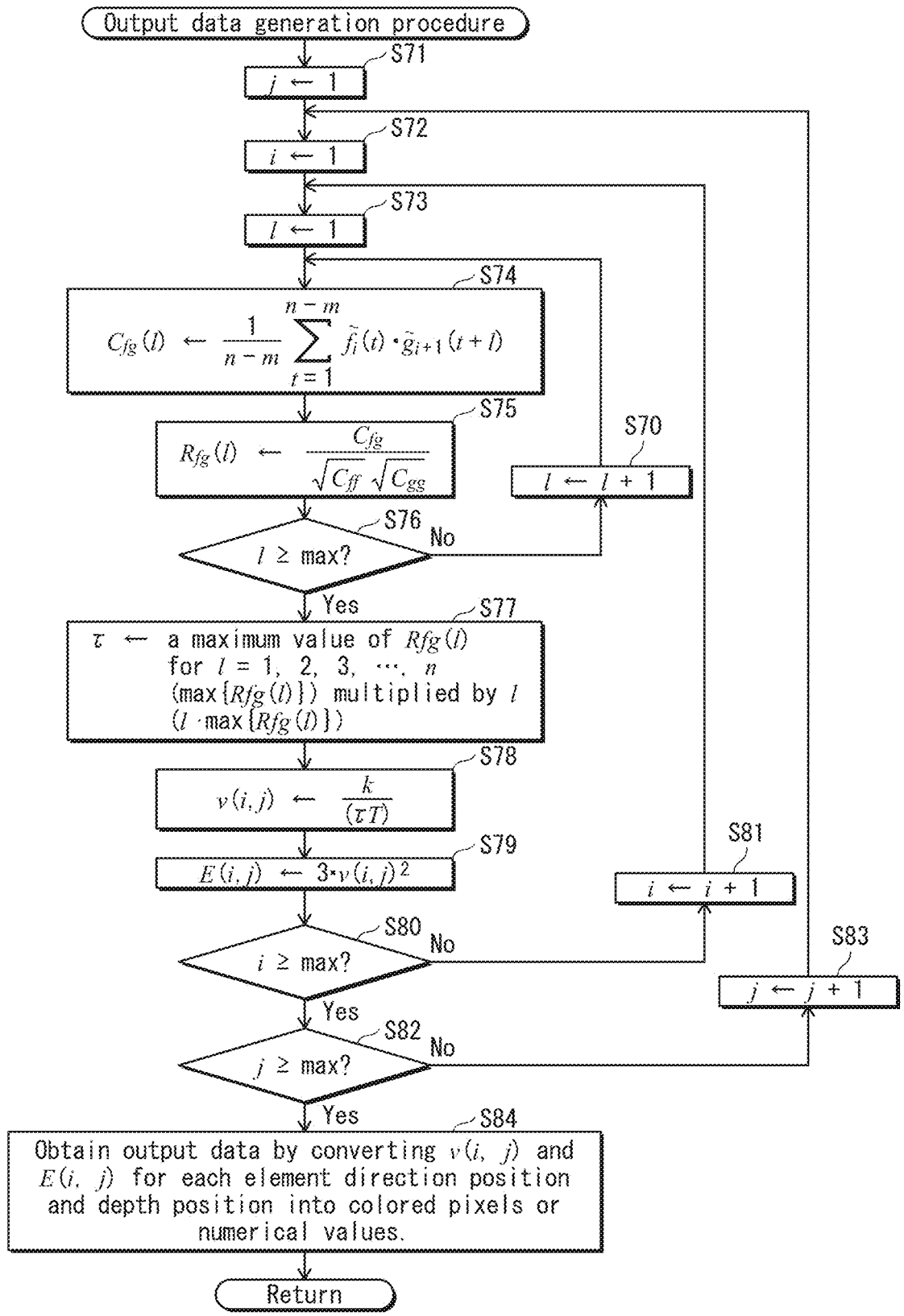
FIG. 18 is a flowchart illustrating an output data generation procedure.

FIG. 18 is a flowchart illustrating an output data generation procedure. This flowchart has a multi-loop structure composed from a loop for variable l, a loop for variable i, and a loop for variable j. The variable l defines a difference between arrival time of a wavefront at array position i and arrival time of the wavefront at array position i+l, and the loop for the variable l is for calculating $R_{fg}$ and $C_{fg}$ for various values that are valid for variable l. The loop for the variable i is for calculating elastic modulus for each element position for one depth position. The loop for the variable j is for repeating $E(i,j)$ for each depth position.

In step S71, the variable j that indicates positions in the depth direction is initialized to 1. In step S72, the variable i that indicates positions in the element array direction is initialized to 1. In step S73, the variable l is initialized to 1. In step S74, the sum operation of Equation 7 is performed for the variable l, which is set to a value according to initialization or a subsequent update, and a correlation value $C_{fg}$ of $f_i(t)$ and $g_{i+1}(t+l)$ is calculated. In step S75, a normalized correlation value $R_{fg}$ is obtained by normalizing $C_{fg}$ according to Equation 6. In step S76, when the variable l has not reached a maximum value, the variable l is incremented (step S70), and processing returns to step S74. Until the variable l reaches the maximum value, the steps of incrementing the variable l, calculating $C_{fg}$, and normalizing $C_{fg}$ are repeated. When the variable l reaches the maximum value, step S76 results in "Yes", and processing proceeds to step S77. In step S77, the shift amount τ in the time direction is calculated by multiplying the variable l by a maximum $R_{fg}$ value among $R_{fg}$ values for l=1, 2, 3, 4, 5, . . . , n. In step S78, a local value of shear wave speed is calculated by calculation of v←k/(τT), and in step S79, v squared is multiplied by 3 to obtain the elastic modulus E(i, j) at coordinates (i,j).

In step S80, it is determined whether or not the variable i has reached a maximum value, and when the maximum value has not been reached, the variable i is incremented (step S81) and processing returns to step S73. In step S82, when a maximum value for the variable j has not been reached, step S82 results in "No", the variable j is incremented in step S83, and processing returns to step S72. When the variable j reaches the maximum value, the loop ends. In step S84, after all the loops have ended, v(i,j) or E(i, j) for each element position and depth position are converted to colored pixels or numerical values in order to obtain output data.

According to the embodiment above, apparent time resolution and spatial resolution are increased by interleaving wavefront frame data of two or more SWS sequences obtained by transmission of focused ultrasound. Thus, elasticity evaluation is performed at high accuracy, based on elastic modulus calculated from speed of a shear wave calculated at the moment of local increase while passing through hard tissue.

(Embodiment 2)

Figure 19:
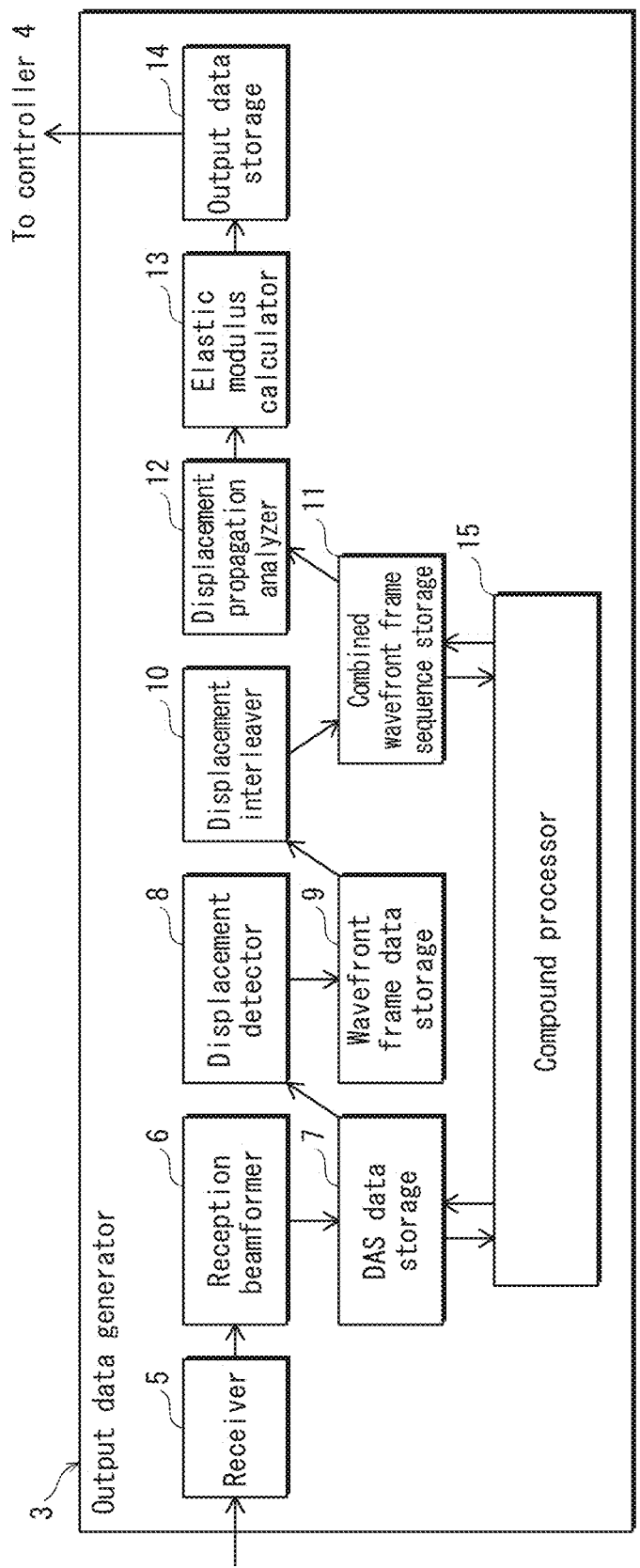
FIG. 19 illustrates a configuration of an output data generator 3 pertaining to embodiment 2.

In embodiment 1, reflected ultrasound is received, delay-and-sum is performed, and wavefront frame data obtained from differences between reference DAS data and detection DAS data is interleaved. The present embodiment relates to an improvement, according to which compound processing is implemented on wavefront frame data of an interleaved SWS sequence. For this improvement, a compound processor is added to the ultrasound processing device 101 of embodiment 2. FIG. 19 illustrates a configuration of the output data generator 3 pertaining to embodiment 2. In FIG. 19, a compound processor 15, which is a new element not present in embodiment 1, FIG. 5B, is added to the output data generator 3. The following describes the compound processor 15, which is newly added in embodiment 2.

The compound processor 15 performs compound processing on reference DAS data and detection DAS data obtained from delay-and-sum processing, and overwrites the reference DAS data and detection DAS data stored in the DAS data storage 7 by using reference DAS data and detection DAS data that has been compounded, thereby making the reference DAS data and detection DAS data that has been compounded the target for generation of wavefront frame data. The wavefront frame data is also compounded from a plurality of wavefront frame data, and wavefront frame data stored in the combined wavefront frame sequence storage 11 is overwritten by wavefront frame data that has been compounded, thereby making wavefront frame data that has been compounded the target for generation of displacement propagation data. In general, compound processing is performing an averaging operation on data components of two or more target image frames to obtain an image frame composed of average value data components, and overwriting the two or more targeted sets of wavefront frame data with wavefront frame data composed of data components that have been averaged. Here, compound processing of DAS data refers to both non-deflection compound and deflection compound processing. Compound processing of wavefront frame data refers only to non-deflection compound processing.

This concludes description of the element added in the present embodiment (the compound processor 15). The following describes changes to processing of existing elements (the push pulse controller 1) that accompany the additional element.

The push pulse controller 1 causes transmission of more reference detection pulses and detection pulses than the push pulse controller 1 of embodiment 1, for reference DAS data and detection DAS data to be targets for compound processing. Reference detection pulses are transmitted three to four more times and detection pulses are transmitted two to three more times than in embodiment 1. Further, when deflection compound processing is executed, deflection pulses are transmitted, and when non-deflection compound processing is executed, non-deflection compound pulses are transmitted.

This concludes description of changes to processing of existing elements that accompanies element addition. FIG. 20A illustrates a detection pulse transmitted by a normal (non-deflection) compound method; FIG. 20B illustrates a deflection detection pulse transmitted by a deflection compound method.

The non-deflection compound method includes transmitting a plurality of detection pulses at a fixed steering angle, and performing an averaging operation on data components of wavefront frame data corresponding to reflected ultrasound obtained by reflection of the plurality of detection pulses, in order to obtain desired wavefront frame data. In FIG. 20A, dw1, dw2, dw3, and dw4 are detection pulses set to the same angle with respect to the element array direction.

The deflection compound method includes transmitting a plurality of detection pulses at a plurality of steering angles, and performing an averaging operation on wavefront frame data corresponding to reflected ultrasound obtained by reflection of the plurality of detection pulses, in order to obtain desired wavefront frame data. In FIG. 20B, dw5, dw6, dw7, and dw8 are detection pulses set to different angles from each other with respect to the element array direction.

Temporal transition of processing of the ultrasound processing device pertaining to embodiment 2 is described below with reference to the timing chart of FIG. 20C and FIG. 21.

Figure 21:
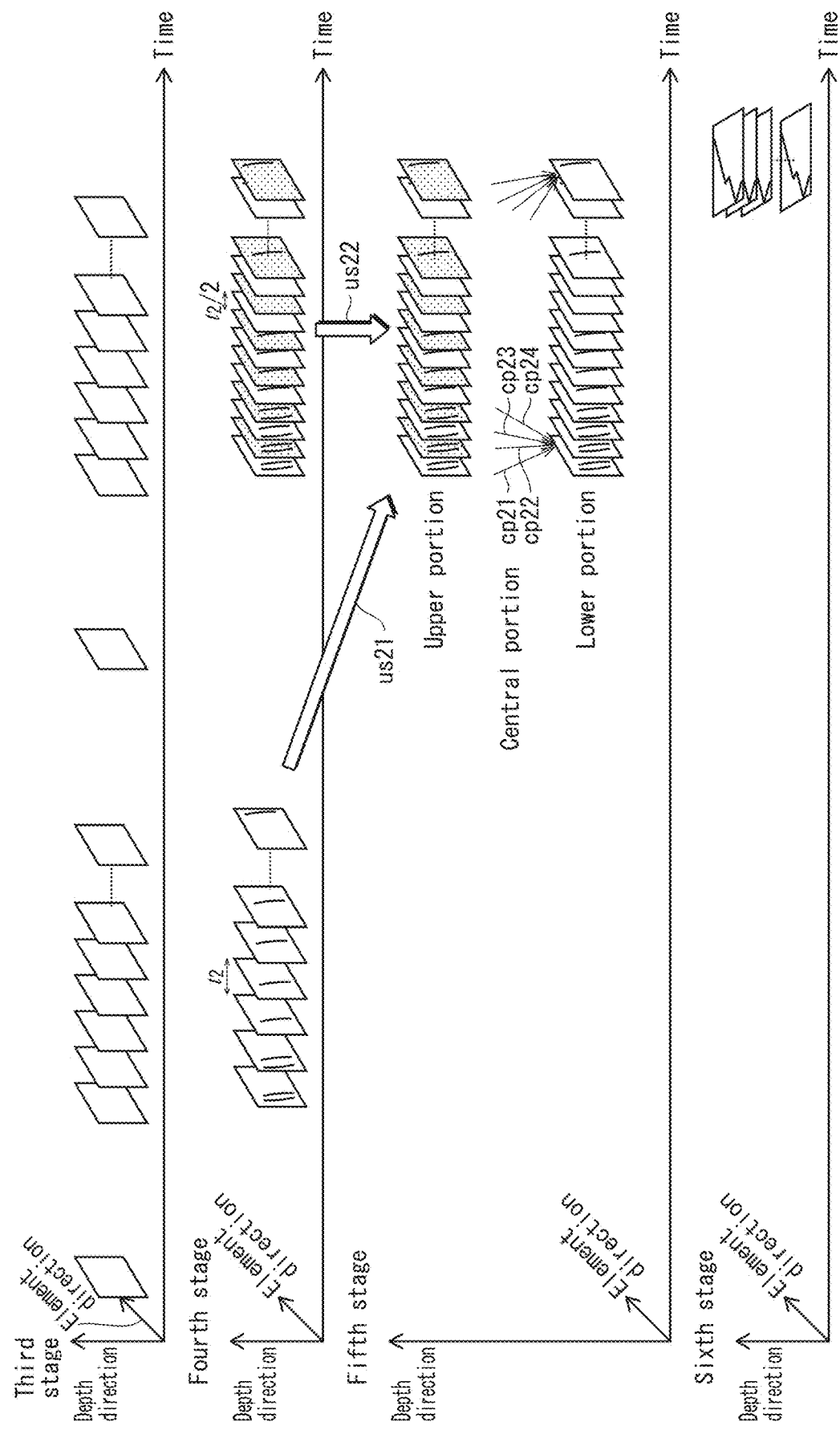
FIG. 21 illustrates a timing chart of processing of the ultrasound processing device 101 pertaining to embodiment 2.

The first and second stages of FIG. 20C and the third to sixth stages of FIG. 21 make up the timing chart pertaining to embodiment 2. When compared to embodiment 1, the following differences are apparent.

First, the number of reference detection pulses and detection pulses is different between embodiment 1 and embodiment 2. In the first stage of FIG. 7 of embodiment 1, one reference detection pulse is transmitted, but in the first stage of FIG. 20C, three reference detection pulses are transmitted, and further, the number of detection pulses is also increased by two. In addition, these reference detection pulses and detection pulses are either non-deflection pulses or deflection pulses.

Second, detection DAS data is different. The detection DAS data according to FIG. 7 of embodiment 1 is, in the second stage, reference DAS data and detection DAS data on a time axis obtained after delay-and-sum processing performed with respect to reflected ultrasound from reference detection pulses and detection pulses. In contrast, in FIG. 20C of embodiment 2, three consecutive sets of reference DAS data are compounded (reference DASc data), three consecutive sets of detection DAS data are compounded (detection DASc data), and the reference DASc data and the detection DASc data are arranged on a time axis. In the upper portion of the second stage, three sets of reference DAS data obtained by delay-and-sum processing of reflected ultrasound of reference detection pulses and a plurality of sets of DAS data obtained by delay-and-sum processing of reflected ultrasound of detection pulses are illustrated. The arrows cp1, cp2, cp3, cp4, cp5, and cp6 in the central portion of the second stage indicate compound processing of three consecutive sets of either reference DAS data or detection DAS data. The arrows cp11, cp12, cp13, cp14, cp15, and cp16 of the second stage indicate compound processing of three consecutive sets of either reference DAS data or detection DAS data in a subsequent SWS tracking step. The reference DASc data and detection DASc data are illustrated in the lower portion of the second stage, and are obtained by compound processing indicated by the arrows.

Third, displacement propagation data generation targets are different. In FIG. 7, embodiment 1, reference DAS data and detection DAS data is obtained, and interleaved wavefront frame data is the target of displacement propagation data generation. In contrast, in FIG. 21, embodiment 2, compounded wavefront frame data that is both interleaved and compounded is the target of displacement propagation data generation. In the upper portion of the fifth stage of FIG. 21, a combined wavefront frame sequence that has been interleaved is illustrated. The signs us21 and us22 in FIG. 21 schematically indicate use of SWS sequence N and SWS sequence N+1 in time direction interleaving. In the central portion of the fifth stage, compound processing of four consecutive sets of wavefront frame data in the combined wavefront frame sequence is indicated by arrows cp21, cp22, cp23, and cp24. In the lower portion of the fifth stage, a combined wavefront frame sequence composed from wavefront frame data for which compound processing has been performed is indicated as a target for compound processing.

FIG. 20C and FIG. 21 illustrate time direction interleaving, but instead of time direction interleaving or in addition to time direction interleaving, element array direction interleaving can be executed to increase resolution in the element array direction.

Figure 22:
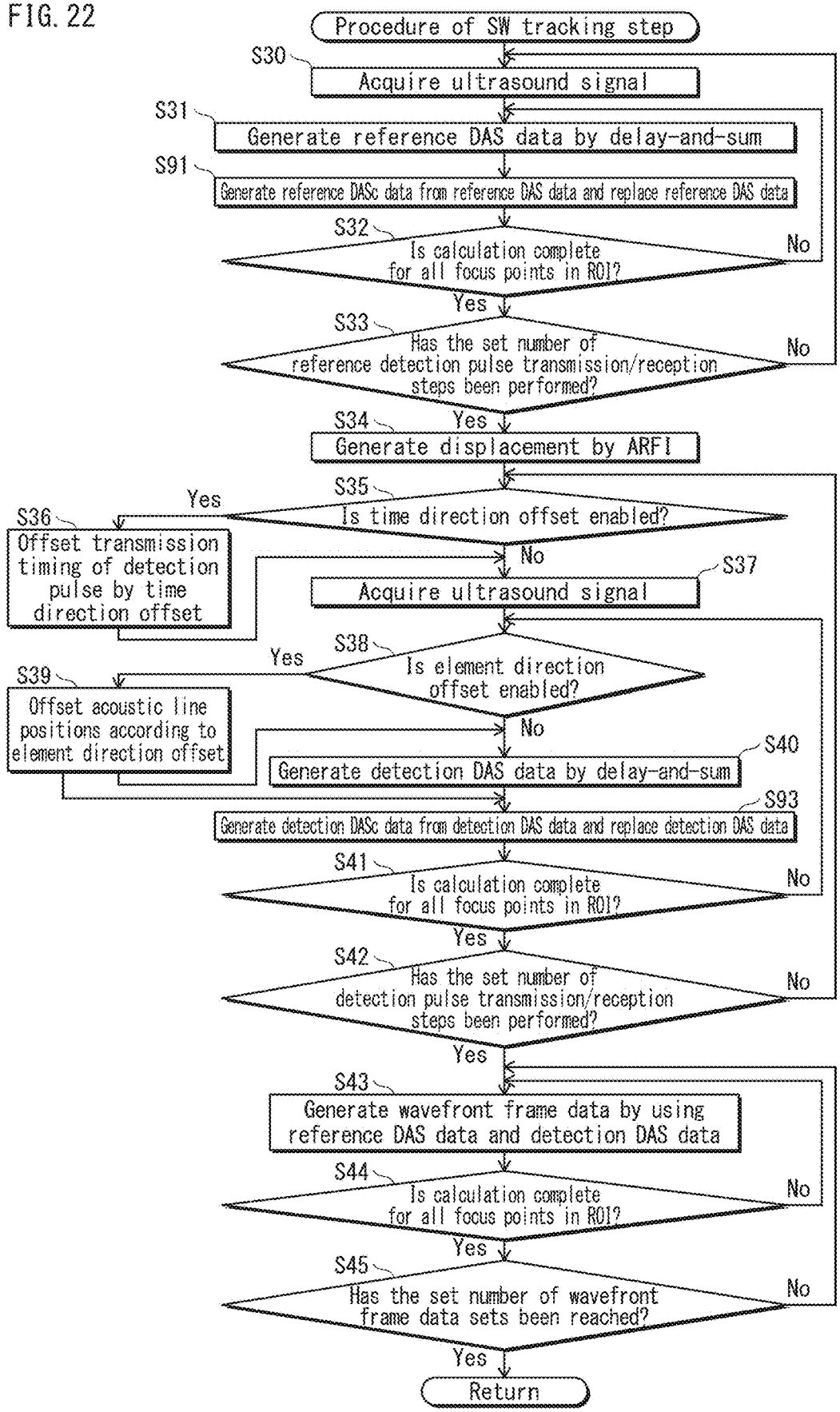
FIG. 22 is a flowchart illustrating a procedure of a shear wave tracking step into which compound processing is added.

The following describes changes to flowcharts. FIG. 22 is a flowchart illustrating an SW tracking step into which compound processing is added. Unlike FIG. 16, steps related to compound processing (step S91 and step S93) are incorporated to key points.

In step S91, inserted between step S31 and step S32, compound processing is performed on reference DAS data, reference DASc data that has been compounded is obtained, and the reference DAS data is overwritten by the reference DASc data.

In step S93, inserted between step S40 and step S41, compound processing is performed on detection DAS data, detection DASc data is obtained, and the detection DAS data is overwritten by the detection DASc data.

Figure 23:
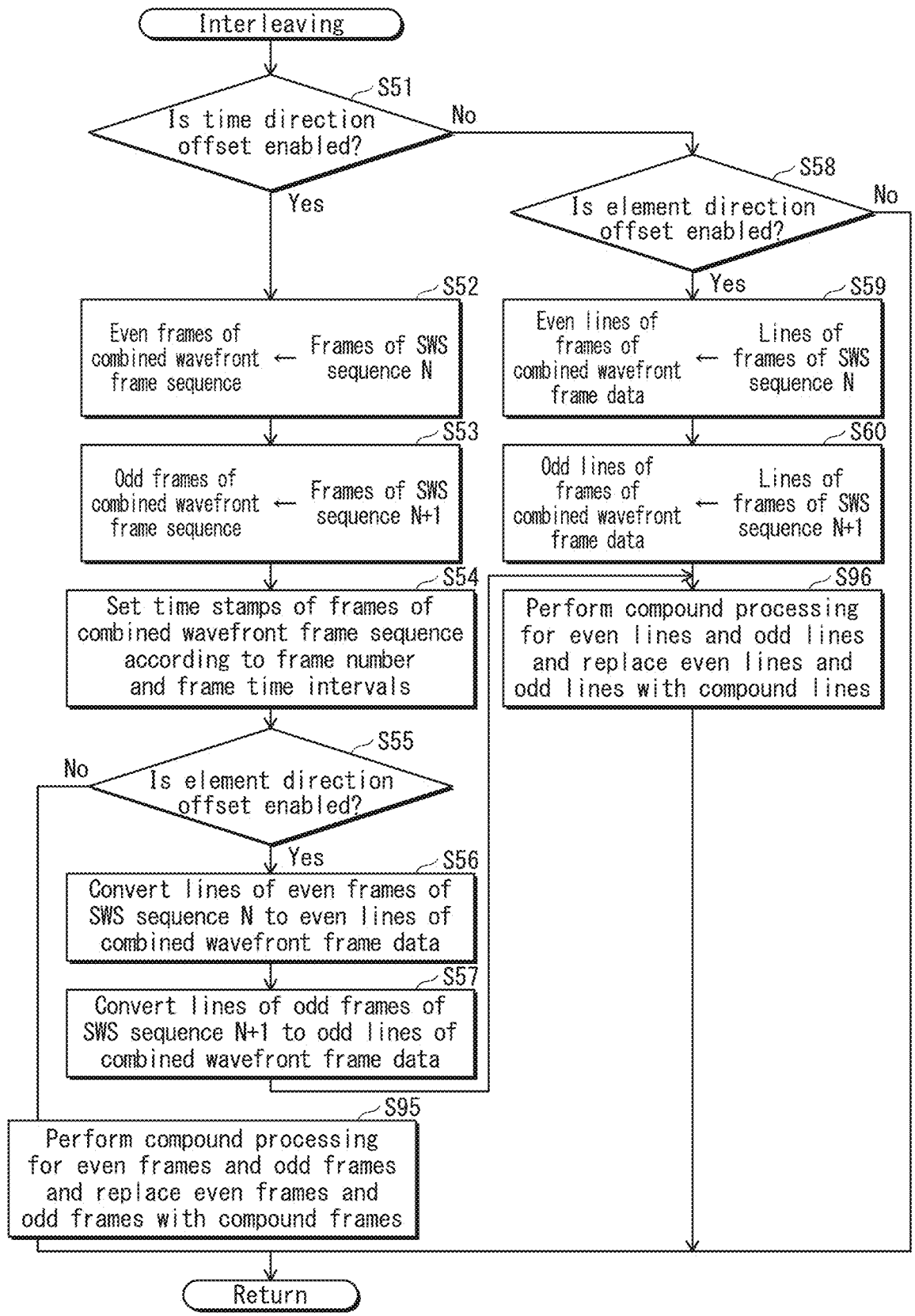
FIG. 23 is a flowchart illustrating a procedure of interleaving pertaining to embodiment 2.

FIG. 23 is a flowchart illustrating a procedure of interleaving pertaining to embodiment 2. FIG. 23 is based on FIG. 17, but step S95 and step S96 are additional steps not present in FIG. 17. Step S95 is executed when it is determined that element array direction offset is not enabled after time direction interleaving executed in steps S52 to S54. In step S95, compound processing is performed on even frames and odd frames of combined wavefront frame data, and even frames and odd frames of the combined wavefront frame data are overwritten by the even frames and odd frames that have been compounded.

Step S96 is executed when it is determined in step S55 that an element array direction offset is enabled and element array direction interleaving is executed in addition to time direction interleaving (step S56, step S57) or when it is determined in step S58 that an element array direction offset is enabled and element array direction interleaving is executed but time direction interleaving is not executed (step S59, step S60). In step S96, compound processing is performed on even lines and odd lines of combined wavefront frame data, and even lines and odd lines of the combined wavefront frame data are overwritten by the even lines and odd lines that have been compounded.

Through the above processing, the even frames and odd frames of combined wavefront frame data, or the even lines and odd lines of combined wavefront data are overwritten with the results of compound processing.

Interleaving targets that are an SWS sequence of an N-th SW tracking step and an SWS sequence of an (N+1)-th SW tracking step are at different times, and therefore the wavefront frame data does not correlate. When alternately arranged by interleaving the wavefront frame data, generation of high-frequency noise becomes remarkable. However, by performing compound processing prior to interleaving, high-frequency noise in a plurality of temporally consecutive sets of wavefront frame data is suppressed, increasing image quality.

According to the present embodiment, noise generated by the interleaving targets SWS sequence N and SWS sequence N+1 being on different time axes is reduced by compound processing. Thus, image quality deterioration is avoided and an increase in element array direction resolution and time direction resolution is achieved.

(Embodiment 3)

Figure 24:
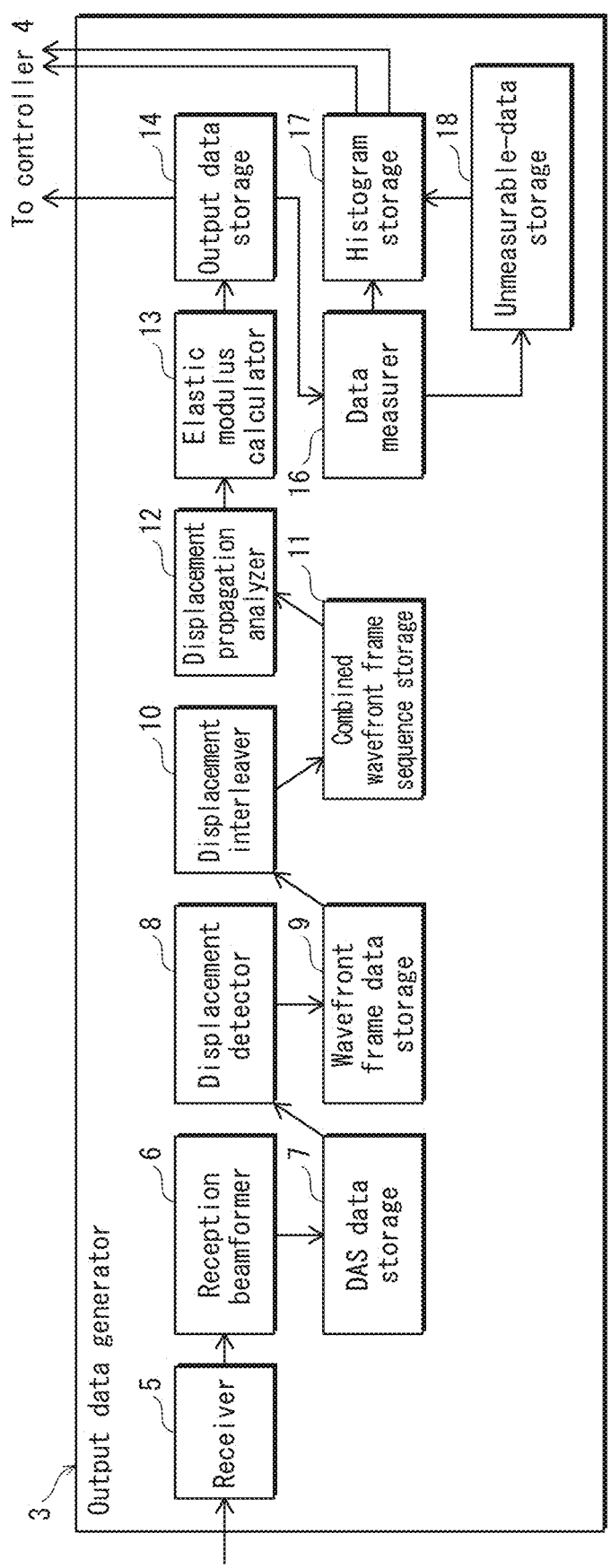
FIG. 24 illustrates a configuration of the output data generator 3 pertaining to embodiment 3.

In embodiment 1, although processing up to generating an elastic modulus image is completed, in the present embodiment a data counter is added to the ultrasound processing device 101 as an element for evaluating results measured by an SW tracking step. FIG. 24 illustrates a configuration of the output data generator 3 pertaining to embodiment 3. Compared to the output data generator 3 illustrated in FIG. 5B, embodiment 1, a data measurer 16, a histogram storage 17, and an unmeasurable-data storage 18 is added in FIG. 24.

The following describes the characteristic elements of the present embodiment (the data measurer 16, the histogram storage 17, and the unmeasurable-data storage 18).

The data measurer 16, when an elastic modulus image is generated, classifies, into a plurality of numerical ranges, elasticity obtained for each of a plurality of positions in the element array direction and the depth direction. Subsequently, according to this classification, the data measurer 16 creates a histogram that associates the numerical ranges of elasticity to the frequency of occurrence of data components. In any numerical range indicated in a histogram, unclassifiable measurement positions may appear in an ROI. Data components calculated for measurement positions that do not belong to any numerical range of elasticity are referred to as "unmeasurable data".

The histogram storage 17 stores a histogram generated by the data measurer 16, and supplies the histogram to the controller 4. Supplying the histogram to the controller 4 enables displaying of the histogram on the display 103.

The unmeasurable data storage 18 stores unmeasurable data found by the data measurer 16.

This concludes description of the characteristic elements of the present embodiment (the data measurer 16, the histogram storage 17, and the unmeasurable-data storage 18). The following describes changes to processing of existing elements (the controller 4, the displacement interleaver 10) that accompany the additional elements.

In the present embodiment, the controller 4, when the amount of unmeasurable data is high, repeats interleaving while changing an element array direction offset, obtains an elastic modulus image, and counts a number of unmeasurable data points in the elastic modulus image. When the number of unmeasurable data points is equal to or less than a threshold, the controller 4 stops the repetition of interleaving. While repeating interleaving, time direction offset, element array direction offset, or both time direction offset and element array direction offset is repeated.

The displacement interleaver 10, in processing of an SWS sequence N+1, inserts a data component of a wavefront image of SWS sequence N+1 between two consecutive data components of a region in which unmeasurable data points are frequent among wavefront images of wavefront frame data N generated from detection DAS obtained after delay-and-sum processing provided with element array direction offset with respect to RF signals outputted from a plurality of acoustic elements.

Figure 25:
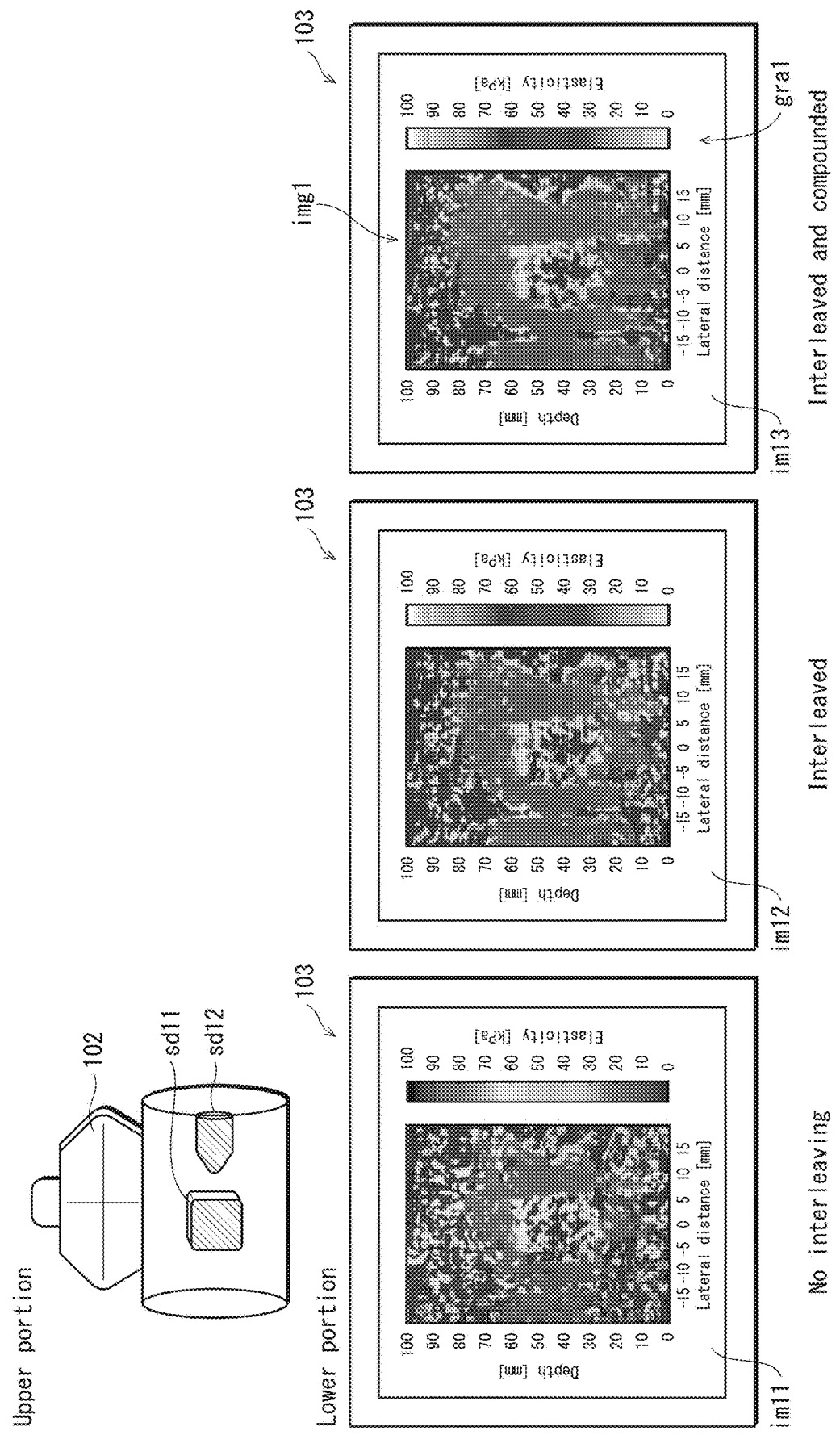
FIG. 25 illustrates a subject and three elastic modulus images obtained from the subject.

FIG. 25 illustrates a subject and three elastic modulus images obtained from the subject. The subject in an upper portion of FIG. 25 has two hard tissue portions sd1 and sd12 arranged in soft tissue.

The lower portion of FIG. 25 illustrates three elastic modulus images im11, im12, and im13. The three elastic modulus images have a common configuration, in which a left axis a depth direction from 0 mm to 100 mm and the bottom axis is an element array direction from −15 mm to +15 mm. The right side shows a color gradient gra1. The color gradient gra1 is an elastic modulus gauge indicating 10 kPa ranges incremented from 0 kPa to 100 kPa, so that a correspondence between elastic modulus and color pixels can be understood. The elastic modulus image on the left side of FIG. 25 is obtained without interleaving of wavefront frame data, the elastic modulus image central to FIG. 25 is obtained by executing both element array and time direction interleaving (hereafter, "interleaving method"), and the elastic modulus image on the right side of FIG. 25 is obtained by executing the compound processing of embodiment 2 and interleaving (hereafter, "interleaving and compounding method"). When compared to the elastic modulus image on the left side, the elastic modulus image that is central exhibits improved image quality in the periphery of the hard tissue sd11. Further, when comparing the elastic modulus image that is central to the elastic modulus image on the right side, it can be seen that shape of the hard tissue is clearer and image quality is improved in the elastic modulus image on the right side.

Figure 26:
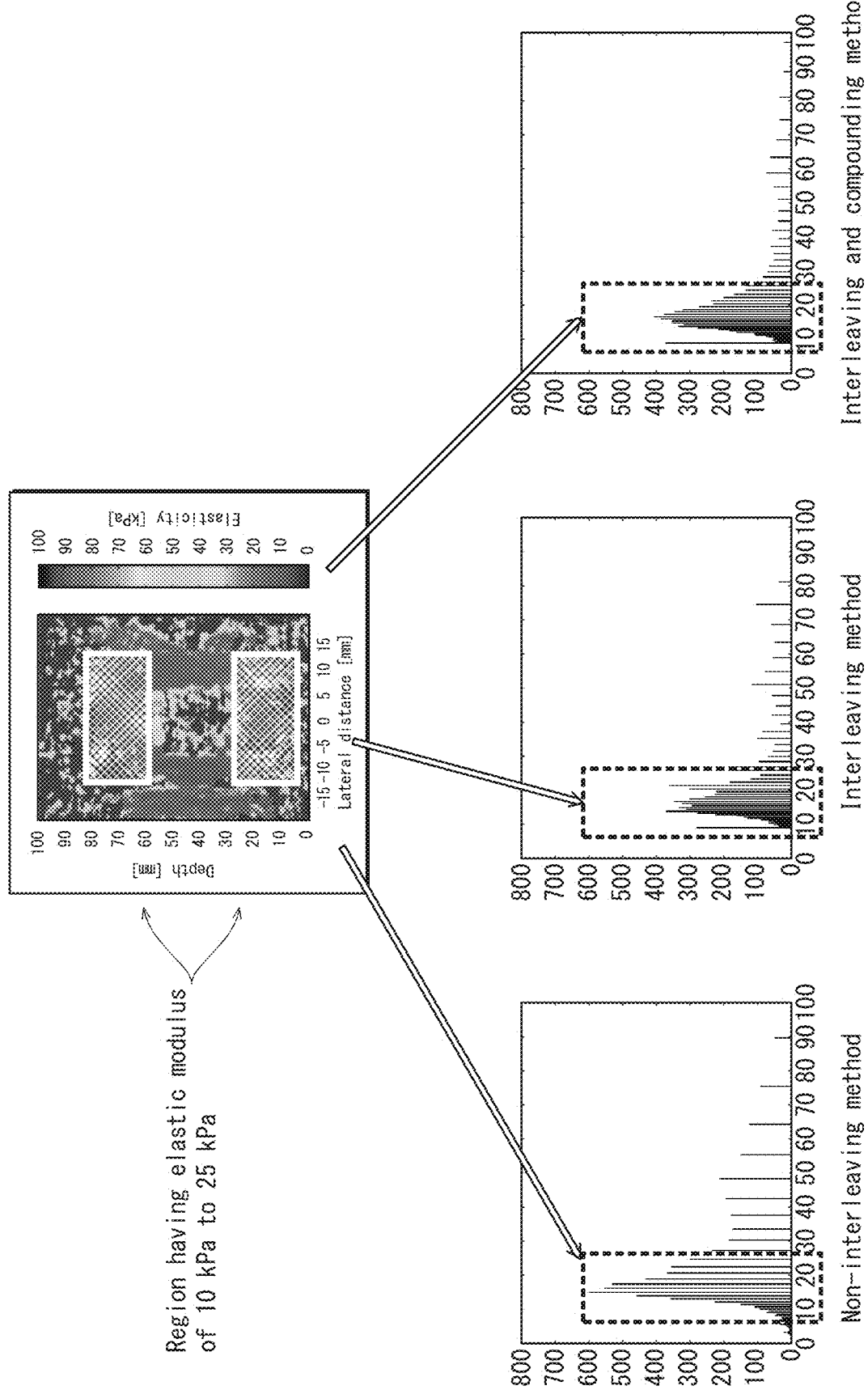
FIG. 26 illustrates histograms generated from a portion of elastic modulus images.

FIG. 26 illustrates histograms generated from a portion of elastic modulus images. The white-framed regions in the elastic modulus image indicate a target of histogram generation. It can be seen that a portion above and below the hard tissue is indicated as the target for histogram generation. The three histograms are a histogram generated from the elastic modulus image generated without interleaving, a histogram generated from the elastic modulus image generated by the interleaving method, and a histogram generated from the elastic modulus image generated by the interleaving and compounding method. The three histograms each have a common configuration, in which a horizontal axis indicates elastic modulus of 0 kPa to 100 kPa, and a vertical axis indicates frequency of occurrence of pixels in the associated elastic modulus image. The numerical range of 10 kPa to 25 kPa indicates elastic modulus of soft tissue. In the horizontal axis, the range enclosed by a dashed line frame indicates a range of elastic modulus from 10 kPa to 25 kPa. When comparing these three histograms, it can be seen that the interleaving method histogram has a higher frequency density and improved resolution over the histogram without interleaving. Further, when comparing the interleaving method and the interleaving and compounding method, the interleaving and compounding method histogram has a higher frequency density.

Figure 27:
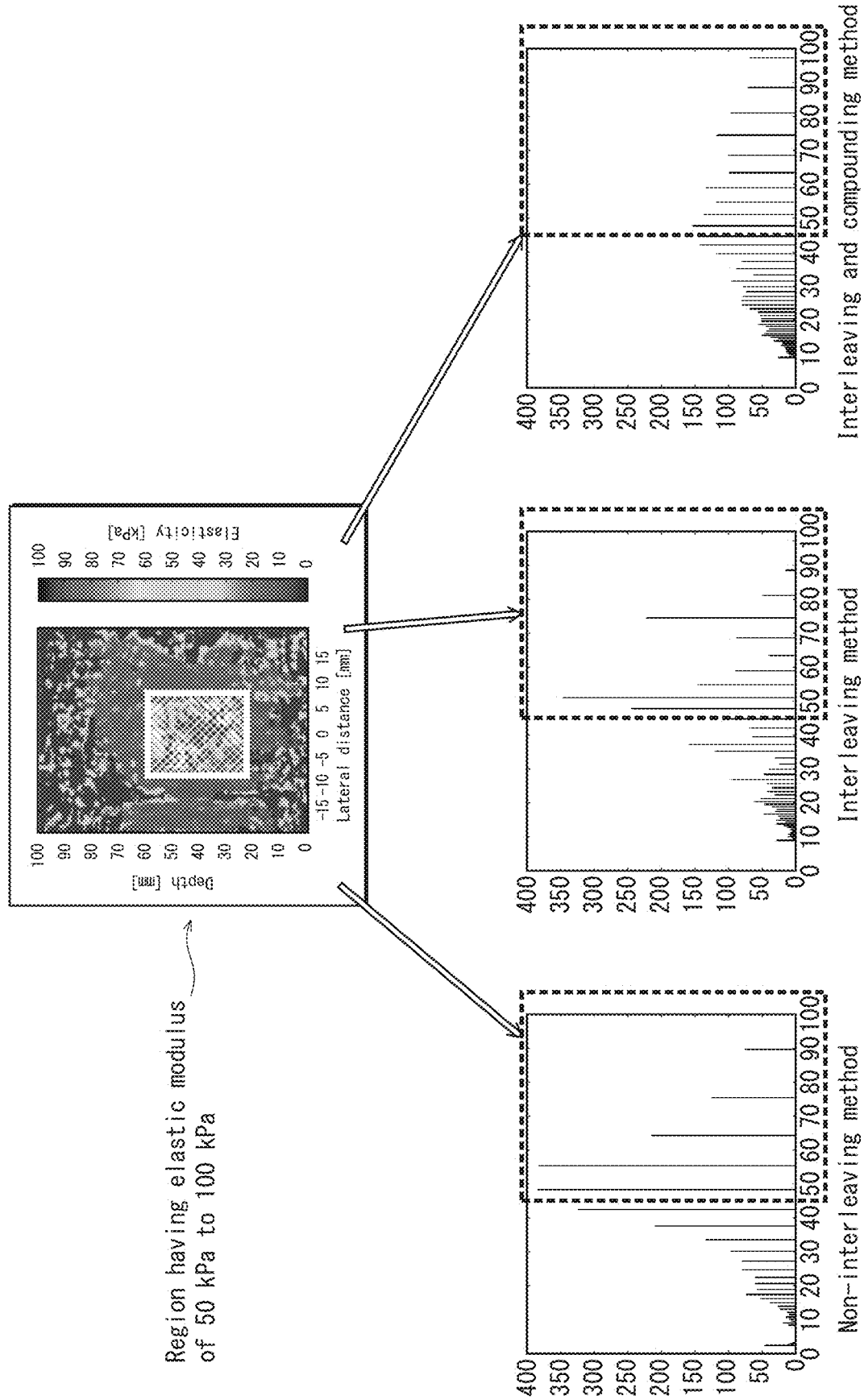
FIG. 27 illustrates histograms generated from a portion of elastic modulus images.

FIG. 27 illustrates histograms generated from a different portion of elastic modulus images. FIG. 27 is similar to FIG. 26, but the portion indicated by a white frame is different. In other words, in FIG. 27, hard tissue in the subject is the target for histogram generation. Three histograms generated from this white frame are illustrated in the lower portion of FIG. 27, as in FIG. 26.

However, because hard tissue is targeted, frequency distribution used to compose the histograms is different. The dashed lines in each histogram indicate a numerical range of elastic modulus of hard tissue, from 50 kPa to 100 kPa. When comparing the numerical range from 50 kPa to 100 kPa in these three histograms, it can be seen that the interleaving method histogram has a higher frequency density and improved resolution over the histogram without interleaving. Further, when comparing the interleaving method and the interleaving and compounding method, the interleaving and compounding method has a higher frequency density.

Figure 28:
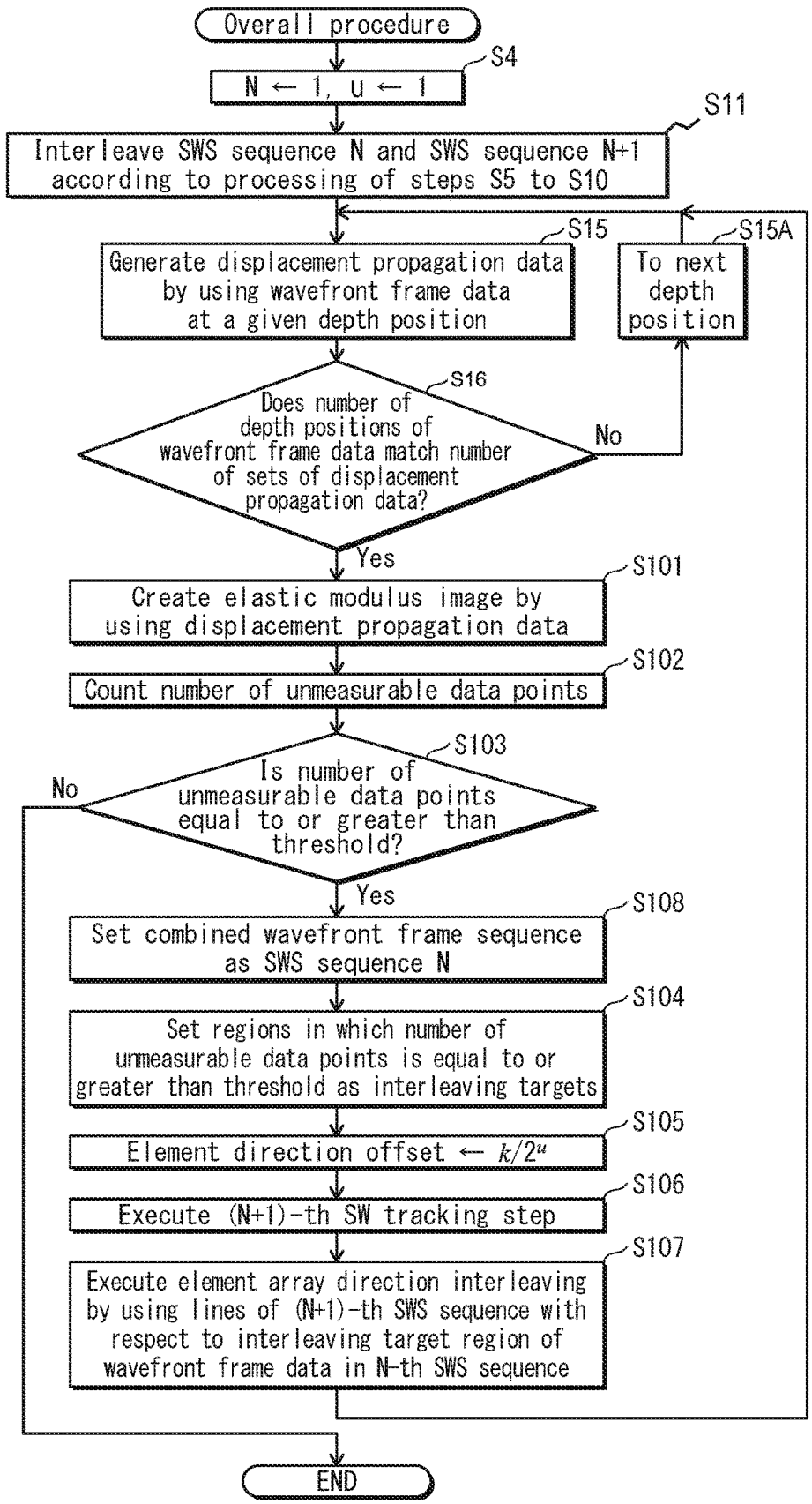
FIG. 28 is a flowchart illustrating an overall procedure pertaining to embodiment 3.

FIG. 28 is a flowchart illustrating an overall procedure according to the ultrasound processing device pertaining to embodiment 3. FIG. 28 is based on the flowchart of FIG. 15, embodiment 1, and differences are described below.

First, opportunities to create elastic modulus images are different. In FIG. 15, embodiment 1, after executing an N-th SW tracking step, an (N+1)-th SW tracking step is performed and interleaving is executed, and subsequently an elastic modulus image is created. Specifically, in FIG. 28, displacement propagation data in generated by using wavefront frame data at a given depth position in step S15. In step S16, whether or not the number of depth positions of wavefront frame data matches the number of displacement propagation data sets in determined. If the number of depth positions does not match the number of displacement propagation data sets, the processing proceeds to step S15A. In step S15A, a next depth position is set, and steps S15 and S16 are subsequently repeated. In the case of a match, processing proceeds to step S101, and an elastic modulus image is created by using the displacement propagation data. In contrast to the processing in FIG. 15, in FIG. 28, in addition to creating an elastic modulus image after obtaining a combined wavefront frame sequence by interleaving SWS sequence N and SWS sequence N+1 (step S101), the combined wavefront frame sequence is set to be the SWS sequence N (step S108), an (N+1)-th tracking step is executed (step S106), interleaving is executed (step S107), and processing returns to step S101 to create an elastic modulus image.

Second, unmeasurable data is treated differently. In FIG. 15, unmeasurable data is not counted, whereas in FIG. 28, after generation of an elastic modulus image in step S101, unmeasurable data is counted (step S102).

Third, targets of interleaving are different. In embodiment 1, time direction interleaving, element array direction interleaving, or element array and time direction interleaving is performed according a time direction offset and/or element array direction offset. In FIG. 28, a portion of wavefront frame data in which unmeasurable data points are equal to or greater than a predefined threshold is set as a target (step S104), element array direction offset is updated (step S105), an (N+1)-th SW tracking step is executed (step S106), and element array direction interleaving is executed using the interleaving target wavefront frame data and the (N+1)-th SWS sequence (step S107). Further, the SWS sequence subsequent to this interleaving is set as an N-th SWS sequence (step S108), and interleaving is executed again.

Fourth, conditions for ending interleaving are different. In FIG. 15, the number of times interleaving is required is calculated from PRT, and interleaving is executed this number of times. In contrast, in FIG. 28, an elastic modulus image is generated after one execution of an SW tracking step, and whether or not the number of unmeasurable data points in this elastic modulus image is below a predefined threshold is an end condition for repetition of interleaving ("No" in step S103).

According to the present embodiment, element array direction interleaving is executed for a region in which the number of unmeasurable data points is equal to or greater than a threshold, until the number of unmeasurable data points decreases below the threshold, and therefore acoustic line density can be increased in a region in which unmeasurable data points are highly concentrated.

(Embodiment 4)

In embodiment 3, the number of unmeasurable data points in an elastic modulus image is counted, and a region in which the number of unmeasurable data points is greater than or equal to a predefined threshold is set as a target for interleaving. In contrast, in the present embodiment, the ultrasound diagnostic device 101 has a designation operation function, and a region designated via the designation operation function is set as a target for element array direction interleaving.

The following describes changes to processing of existing elements (display 103), in order to implement the designation operation function.

The display 103 of the present embodiment has a touch panel function. Thus, when an elastic modulus image is displayed, a user can designate a region as a target for higher definition through interleaving, by touching the region with a finger.

A display controller is added to the controller 4 as an ancillary element. The display controller displays a graphical user interface (GUI), displaying an elastic modulus image according to an N-th SW tracking step, and can receive an input operation from a user. When a region of an elastic modulus image is designated via an operation with respect to the display 103, in order that element array direction interleaving be executed with respect to the region, the display controller causes execution of an N-th SW tracking step, and causes the displacement interleaver 10 to execute interleaving of an obtained SWS sequence and an SWS sequence obtained via the N-th SW tracking step.

Figure 29A:
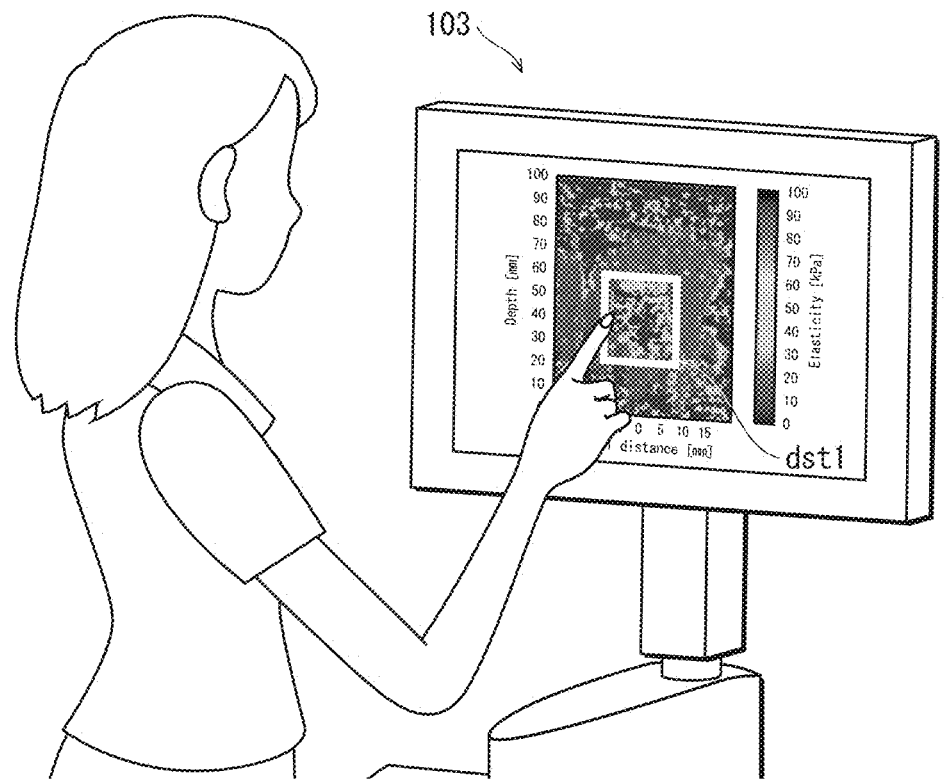
FIG. 29A illustrates a usage example when receiving a region specifying operation with respect to an elastic modulus image displayed on a display 103.

FIG. 29A illustrates a usage example when receiving a region specifying operation with respect to an elastic modulus image displayed on the display 103. The sign dst1 in FIG. 29A indicates a closed loop drawn on the screen of the display 103 by dragging a fingertip across the screen, and the interior of the closed loop is designated as an interleaving target region.

Figure 29B:
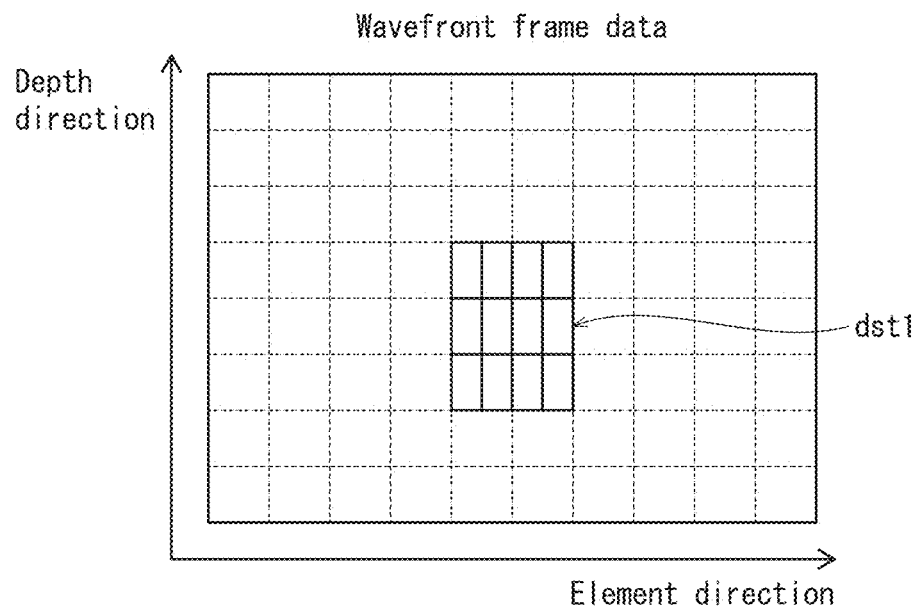
FIG. 29B illustrates a portion of an elastic modulus image specified by a region specifying operation.

FIG. 29B indicates a designated region in wavefront frame data. Among wavefront frame data, element array direction interleaving and/or element array and time direction interleaving is executed with respect to the designated region, thereby doubling acoustic line density of the designated region.

Figure 30:
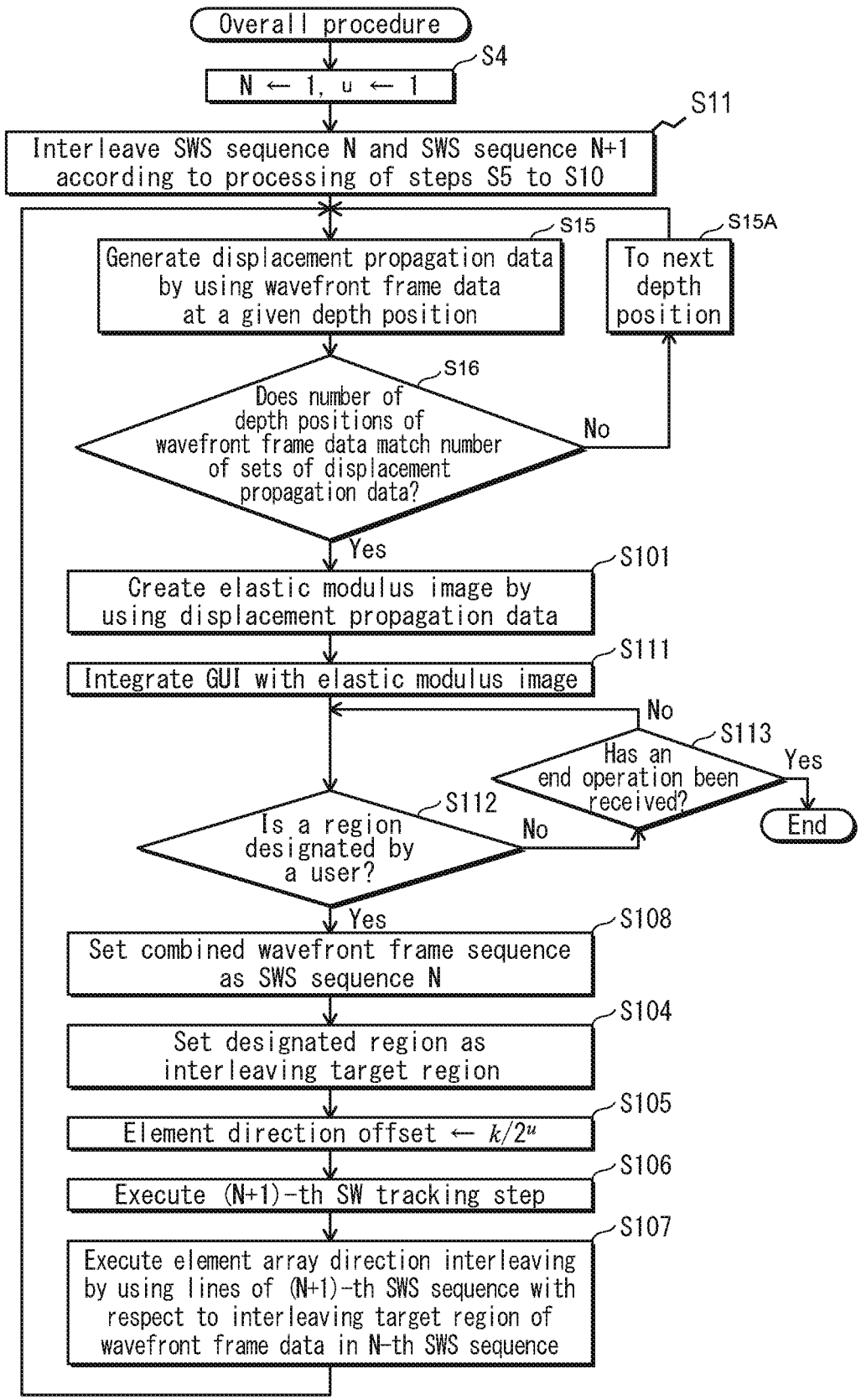
FIG. 30 is a flowchart illustrating an overall procedure pertaining to embodiment 5.

FIG. 30 is a flowchart illustrating an overall procedure pertaining to embodiment 4. FIG. 30 is based on the flowchart of FIG. 28, embodiment 3. Compared to this base, the following differences exist.

First, processing after elastic modulus image generation is different. In FIG. 28, embodiment 3, the number of unmeasurable data points is counted after elastic modulus image generated. In contrast, in FIG. 30, after elastic modulus image generation (step S101), a GUI is displayed (step S111), and a region designation operation is received from a user (step S112).

Second, targets of interleaving are different. In FIG. 28, embodiment 3, a region in which the number of unmeasurable data points is greater than or equal to a predefined threshold is the target of interleaving. In contrast, in FIG. 30, a region designated by a user operation via a GUI (designated in step S112) is set as the target of interleaving (step S104).

Third, conditions for ending interleaving are different. In FIG. 28, an SW tracking step is executed once, an elastic modulus image is created, and the number of unmeasurable data points in the elastic modulus image decreasing below a predefined threshold is the end condition for repetition of interleaving ("No" in step S103). In contrast, in FIG. 30, an end operation via the GUI is the end condition for repetition of interleaving (step S113).

The interleaving includes setting each data component line of wavefront frame data of SWS sequence N as even lines of a designated region of wavefront frame data in a combined wavefront frame sequence, and setting each data component line of wavefront frame data of SWS sequence N+1 as odd lines of the designated region of the wavefront frame data in the combined wavefront frame sequence.

According to the present embodiment, element array direction interleaving is executed with respect to a region designated by a user on an elastic modulus image generated after one execution of an SW tracking step, and therefore accuracy of elasticity evaluation is increased.

(Embodiment 5)

In embodiment 1, when element array direction interleaving is executed, an ARFI is transmitted two or more times, two or more SWS sequences are obtained, and the two or more SWS sequences are targets of the element array direction interleaving. In contrast, the present embodiment relates to an improvement, according to which two or more SWS sequences are obtained from one ARFI transmission, and the two or more SWS sequences are set as element array direction interleaving targets.

The following describes the processing of existing elements (the reception beam former 6, the displacement detector 8, and the displacement interleaver 10) for obtaining two or more SWS sequences from one ARFI transmission.

The reception beam former 6 of the present embodiment executes beamforming twice when a reference detection pulse is transmitted and reflected ultrasound thereof is received prior to the N-th ARFI transmission, the beamforming being executed with different acoustic line positions each time. Thus, reference DAS data of SWS sequence N is obtained and reference DAS data of SWS sequence N+1 is obtained.

In the same way, the reception beam former 6 executes beamforming twice when a detection pulse is transmitted and reflected ultrasound thereof is received subsequent to the N-th ARFI transmission, the beamforming being executed with different acoustic line positions each time. Thus, detection DAS data of SWS sequence N is obtained and detection DAS data of SWS sequence N+1 is obtained. Setting changes of acoustic line positions when executing the beamforming are achieved by changing element array direction offset between transmitting an initial reference detection pulse and transmitting a second reference detection pulse. Reference DAS data and detection DAS data of SWS sequence N, and reference DAS data and detection DAS data of SWS sequence N+1 is all written to the DAS data storage 7.

The displacement detector 8 extracts, from DAS data written to the DAS data storage 7, displacement portions of shear wave wavefronts from reference DAS data and detection DAS data of the SWS sequence N, in order to obtain wavefront frame data of the SWS sequence N and write the wavefront frame data to the wavefront frame data storage 9. Likewise, the displacement detector 8 extracts displacement portions of shear wave wavefronts from reference DAS data and detection DAS data of the SWS sequence N+1, in order to obtain wavefront frame data of the SWS sequence N+1 and write the wavefront frame data to the wavefront frame data storage 9.

The displacement interleaver 10 executes element array direction interleaving with respect to the wavefront frame data of the SWS sequence N and the wavefront frame data of the SWS sequence N+1 written to the wavefront frame data storage 9, thereby obtaining a combined wavefront frame sequence. This concludes changes to existing elements in embodiment 5.

Figure 31:
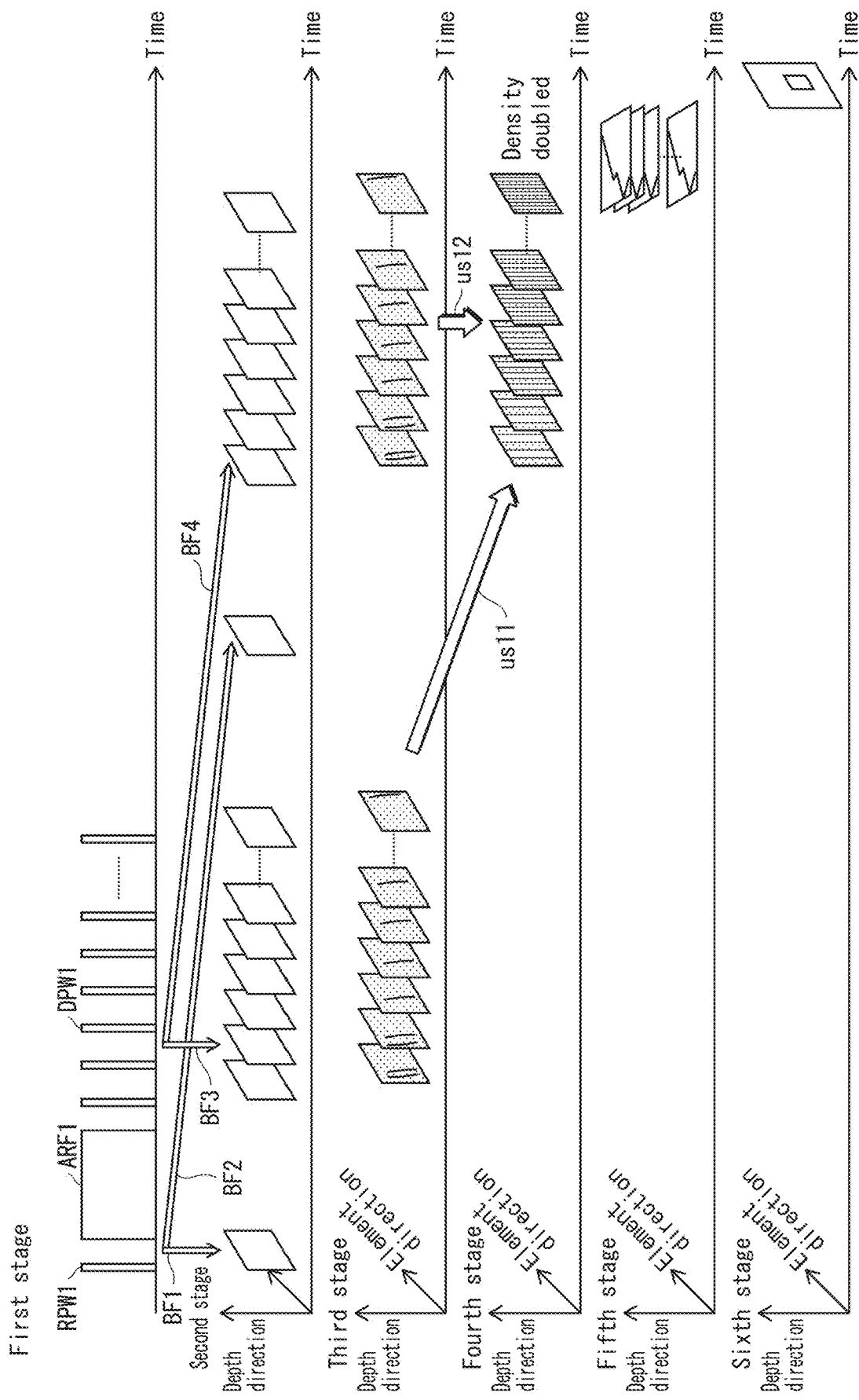
FIG. 31 is a timing chart illustrating element array direction interleaving in embodiment 5.

FIG. 31 is a timing chart illustrating element array direction interleaving in embodiment 5. FIG. 31 is based on FIG. 10, and differences from FIG. 10 are described below.

First, the number of ARFI transmissions is different. According to FIG. 10, an ARFI is transmitted twice, while according to FIG. 31, an ARFI is only transmitted once.

Second, proportions of reference detection pulses to reference DAS data are different. According to FIG. 10, one reference detection pulse corresponds to one set of reference DAS data. In contrast, according to FIG. 31, one reference detection pulse corresponds to two sets of reference DAS data. This one-to-two correspondence results from beamforming being performed twice, using different acoustic line settings, when receiving reflected ultrasound from transmission of a reference detection pulse, generating two sets of reference DAS data. The signs BF1 and BF2 in FIG. 31 indicate beamforming being performed twice using different acoustic line settings.

Third, proportions of detection pulses and sets of detection DAS data are different. According to FIG. 10, each detection pulse corresponds one-to-one with a set of detection DAS data. In contrast, according to FIG. 31, each detection pulse corresponds one-to-two with sets of detection DAS data. This one-to-two correspondence results from beamforming being performed twice, using different acoustic line settings, when receiving reflected ultrasound from transmission of a detection pulse, generating two sets of detection DAS data. The signs BF3 and BF4 in FIG. 31 indicate beamforming being performed twice using different acoustic line settings.

Wavefront frame data is generated based on reference DAS data and detection DAS data generated as described above, SWS sequence N and SWS sequence N+1 are obtained, and become targets for interleaving.

According to the present embodiment, a plurality of SWS sequences are generated for element array direction interleaving from a single ARFI transmission, and therefore the number of ARFI transmissions to obtain a combined wavefront frame sequence can be decreased, and therefore the burden imposed on the subject of receiving ARFI transmission can be reduced.

<Effects>

Interleaving according to an ultrasound processing device provided with the above-described means for solving the problems includes frame interleaving, in which a wavefront frame included in a wavefront frame sequence is inserted between two wavefront frames that are consecutive in a time direction among wavefront data included in another wavefront frame sequence, and/or element array direction interleaving, in which a data component from wavefront frame data included in a wavefront frame sequence is inserted between two data components that are arranged in an element array direction among data components included in another wavefront frame sequence. Thus, apparent resolution can be improved, and accuracy of SWS calculation can be improved.

<Notes>

The above describes the best embodiments known to the applicant at the time of application, but further improvements and modifications may be implemented as indicated under the technical topics below.

(Application to Non-Destructive Inspection Devices)

Embodiments of an ultrasound processing device are presented under the assumption that the ultrasound processing device is used in an ultrasound diagnostic system illustrated in FIG. 1, but this is merely an example. The ultrasound processing device may be used in a non-destructive inspection system for inspection of equipment and building interiors by ultrasound. Further, as long as processing of ultrasound signals is performed, the ultrasound processing device may be used in an internal inspection system of nuclear facilities and a seabed exploration system, for example.

(Reference DAS Data Generation Timing Variation)

Figure 32:
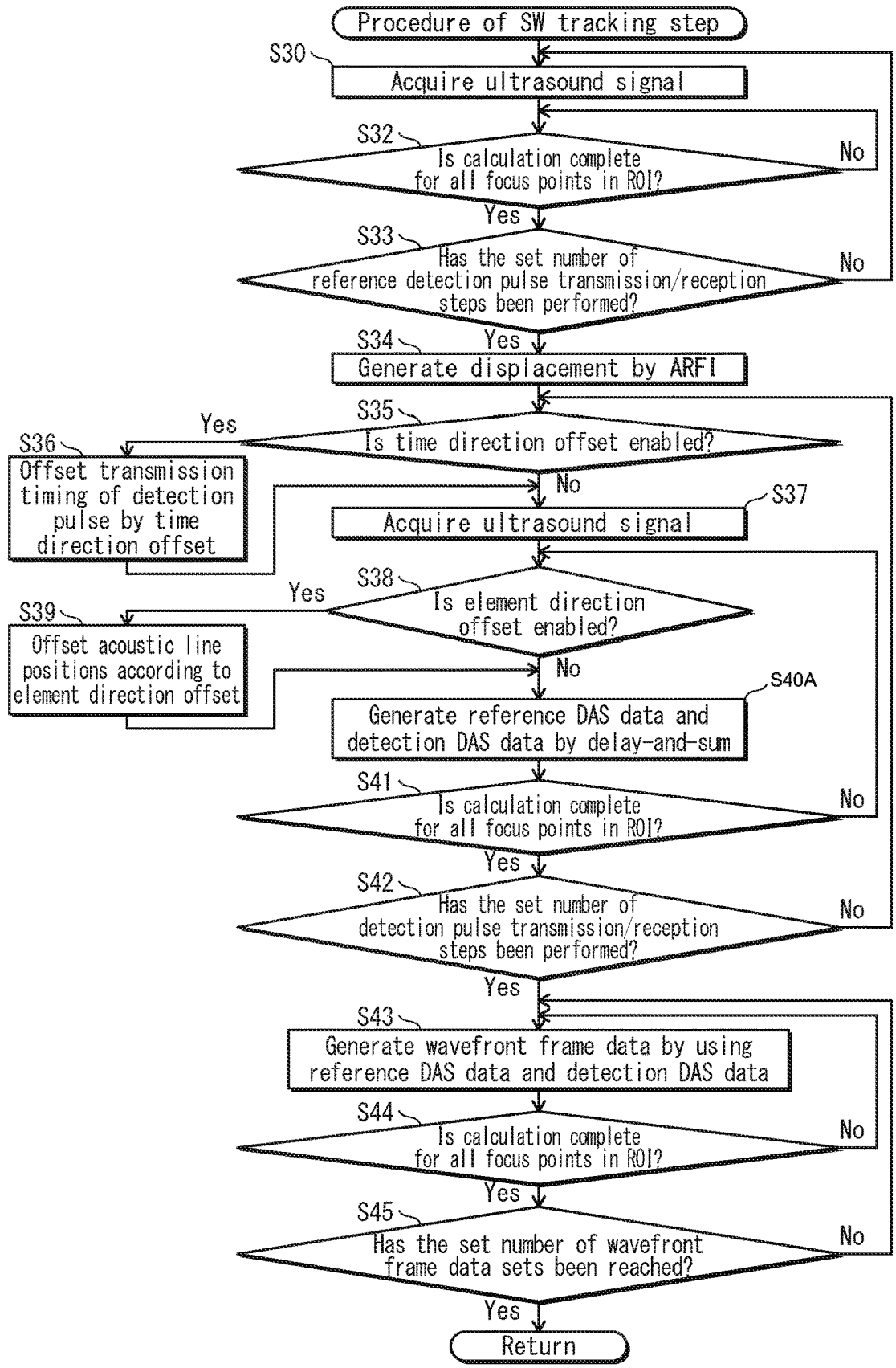
FIG. 32 is a flowchart modified so that delay-and-sum for reference delay-and-sum (DAS) data generation and delay-and-sum for detection DAS data generation are performed after transmission of a detection pulse.

According to FIG. 16, delay-and-sum for reference DAS data generation is performed after transmission of a reference detection pulse and delay-and-sum for detection DAS data generation is performed after transmission of a detection pulse, but delay-and-sum for reference DAS data generation and delay-and-sum for detection DAS data generation may be performed after transmission of a detection pulse. FIG. 32 is a flowchart modified so that delay-and-sum for reference DAS data generation and delay-and-sum for detection DAS data generation are performed (step S40A) after transmission of a detection pulse.

(Interleaving Targets)

According to embodiment 1, in order to understand shear wave attenuation, wavefront frame data is obtained based on reflected ultrasound from a reference detection pulse transmitted prior to transmission of focused ultrasound. However, interleaving may be executed on reference DAS data and detection DAS data.

(Subject Target)

The ultrasound processing device 101 of each embodiment is applicable to elasticity evaluation in a mammary gland region. As a property of living tissue, for example in a mammary gland region, it is reported that cancerous tissue is several dozen times harder than fatty tissue (JP 5555286, paragraph 0028), and therefore a hard portion suspected of being cancerous tissue can clearly be detected. However, a mammary gland region is merely one example, and the subject may be any subject in which this clear difference in hardness exists. For example, in manufacture of a food product, the ultrasound processing device may be applied to inspection of whether or not a contaminant is mixed into the food product.

(Ultrasound for Tissue State in ROI)

Planar pulses are used as ultrasound for acquiring tissue state in an ROI, but this is merely one example. As long as information in an ROI can be acquired all at once, a spherical wave may be used. In such a case, the probe may be a probe with a curved surface. Further, the ultrasound probe may be a transesophageal probe or intravascular probe.

(Applicable Range of Elasticity Evaluation)

SWS acquisition is described as a technique of elasticity evaluation according to the ultrasound processing device 101, but elasticity evaluation may be performed according to shear wave speed imaging (SWSI) or shear wave speed measurement (SWSM).

(Embodiment Combinations)

Embodiment 3 and embodiment 4 are based on the ultrasound processing device 101 of embodiment 1, but embodiment 3 and embodiment 4 may be based on the improved base of the ultrasound processing device 101 of embodiment 2 (adding elements for compound processing). Further, embodiment 4 may be based on the ultrasound processing device 101 of embodiment 3.

(Variations of Ultrasound Processing Device 101)

The ultrasound probe 102 and the display 103 may be parts of the ultrasound processing device 101. Further, the ultrasound probe 102 and/or the display 103 need not be present. It suffices that the ultrasound processing device 101 processes input from the ultrasound probe 102, and outputs a video signal indicating an elastic modulus image that the display 103 displays. Further, all or part of the processing elements of the ultrasound processing device of each embodiment may be included in the ultrasound probe 102.

(Variations of Ultrasound Probe 102)

The ultrasound probe 102 may be a probe in which ultrasound transducers are arranged in a one-dimensional direction, and may be a probe in which ultrasound transducers are arranged in two-dimensional array.

(Implementation as Computer System)

When all or part of the elements described above are part of a computer system comprising a microprocessor, read-only memory (ROM), random access memory (RAM), hard disk, etc., it is preferable that a computer program that achieves the same operations as the elements is stored on the RAM or hard disk. The microprocessor operates according to the computer program, thereby achieving the functions of the elements.

(Integration)

All or part of the elements described above may be part of a single system large scale integration (LSI). A system LSI is a super-multifunctional LSI manufactured by integrating a plurality of elements on one chip, specifically a computer system comprising a microprocessor, ROM, RAM, etc. The RAM stores a computer program that achieves the operations of the plurality of elements. The microprocessor operates according to the computer program, the system LSI thereby achieving the functions of the plurality of elements. Further, LSI is just an example, and a dedicated circuit or general-purpose processor may be implemented. A field programmable gate array (FPGA) may be used or a reconfigurable processor that allows reconfiguration of cell connections and settings in the LSI after manufacture may be used.

(Modularization)

All or part of the elements described above may be implemented as an integrated circuit (IC) card or single module that can be attached to or removed from a device. The IC card or module is a computer system comprising a microprocessor, ROM, RAM, etc. The IC card or module may include the super-multifunctional LSI described above. The microprocessor operates according to a computer program, the IC card or module thereby achieving the functions of the elements. The IC card or module may be tamper-resistant.

(Implementation as Program)

The present invention may be implemented by processing of a computer, as indicated above. Further, the present invention may be implemented by a computer program executed by processors of a central processing unit (CPU), etc., and may be a digital signal of the computer program.

Further, the present invention may be the computer program or the digital signal stored on a computer-readable storage medium. Examples of computer-readable storage mediums include a flexible disk, hard disk, compact disc read-only memory (CD-ROM), magneto-optical (MO) drive, digital versatile disc (DVD), digital versatile disc read-only memory (DVD-ROM), digital versatile disc random access memory (DVD-RAM), Blu-ray disc (registered trademark), semiconductor memory, etc. Further, the present invention may be implemented as the storage medium on which the digital signal is stored. The computer program or the digital signal may be transmitted via telecommunication lines, wireless or wired communication lines, a network such as the internet, data broadcasts, etc.

A computer system comprising a microprocessor and memory may have the computer program stored in the memory, and the microprocessor may operate according to the computer program.

Further, by storing the computer program or the digital signal on the storage medium and transporting the storage medium, or by transferring the computer program or the digital signal across the network, etc., the present invention may be implemented on another independent computer system.

(Embodiment Combinations)

The embodiments and modifications may be combined with each other.

Further, the numbers used above are all representative examples used to describe the present invention in detail, and the present invention is not limited to these representative examples.

Further, the divisions into the function blocks in the drawings are examples, and multiple function blocks may be implemented as one function block, one function block may be divided into multiple function blocks, and a portion of functions of a given function block may be moved to another function block. Further, the functions of a plurality of function blocks having similar functions may be processed in parallel or serially by a single hardware or software unit.

Further, the orders of processing steps are described as representative examples for description of the present invention, and the present invention is not limited to these examples. Further, a portion of the steps may be executed at the same time (in parallel) as another step.

Further, without departing from the spirit of the present invention, various modifications of the embodiments within a scope that would occur to a person having ordinary skill in the art are also included in the present invention.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound diagnostic system comprising:
an ultrasound probe that has an acoustic element array comprising a plurality of acoustic elements in an element array direction; and
an ultrasound processing device comprising an ultrasound signal processing circuit including:
 a push pulse controller that controls the acoustic element array to execute a plurality of transmissions of focused ultrasound to a same position in a subject, in order to generate radiation force in the subject;
 a transmitter that controls the acoustic element array to execute transmission of reference ultrasound prior to the plurality of transmissions of focused ultrasound and to execute a plurality of transmissions of detection ultrasound after each transmission of focused ultrasound and before a next transmission of focused ultrasound;
 a generator that obtains a wavefront frame sequence for each of the transmission of focused ultrasound, by generating wavefront frame data indicating wavefront positions of a shear wave at a plurality of points along a time axis, based on detection of propagation of the shear wave caused by the radiation force generated by the focused ultrasound, wherein the detection of propagation by the generator is performed by extracting values indicating displacement of subject tissue by comparing reflected ultrasound signals obtained from reflected ultrasound of the reference ultrasound received by the ultrasound probe and reflected ultrasound signals obtained from reflected ultrasound of the detection ultrasound received by the ultrasound probe, and wherein the generator comprises a beamformer that performs delay-and-sum of element input signals from respective acoustic elements of the acoustic element array, the element input signals corresponding to the reflected ultrasound signals of the reference ultrasound and the reflected ultrasound signals of the detection ultrasound;
 an interleaver that obtains a combined wavefront frame sequence by interleaving a plurality of wavefront frame sequences obtained by the generator corresponding to consecutive transmissions of focused ultrasound; and
 a calculator that calculates shear wave speed or elastic modulus in the subject, by using frame time intervals and change amounts of wavefront positions of the shear wave indicated by the combined wavefront frame sequence,
 wherein the interleaving comprises at least one of
  (i) frame interleaving, in which: the transmitter controls the acoustic element array to execute the plurality of transmissions of detection ultrasound such that a first detection pulse for the detection of propagation of the shear wave generated by one transmission of the plurality of transmissions of focused ultrasound is provided with a time direction offset as compared to a first detection pulse for detection of the propagation of the shear wave generated by another transmission of the plurality of transmissions of focused ultrasound transmitted consecutively with respect to said one transmission of focused ultrasound, wherein the time direction offset is less than a transmission interval of the plurality of transmissions of detection pulses transmitted after each of the plurality of transmissions of focused ultrasound, and the interleaver inserts a wavefront frame included in the wavefront frame sequence corresponding to the one transmission of focused ultrasound between two wavefront frames that are consecutive in a time direction among wavefront data included in another wavefront frame sequence corresponding to said another transmission of focused ultrasound, and
  (ii) element array direction interleaving, in which: the beamformer performs the delay-and-sum of the element input signals corresponding to the detection ultrasound for the detection of propagation of the shear wave generated by one of the plurality of transmissions of focused ultrasound by providing an offset in the element array direction for acoustic line positions of the acoustic elements, such that the acoustic line positions are changed to intervals between the plurality of acoustic elements, and performs the delay-and-sum of the element input signals corresponding to the detection ultrasound for the detection of propagation of the shear wave generated by said another focused ultrasound without providing the offset for the acoustic line positions such that the acoustic line positions are set to predefined positions in an element region of each of the acoustic elements, and the interleaver inserts a data component from the wavefront frame data included in a wavefront frame sequence corresponding to the one transmission of focused ultrasound and obtained by performing the delay-and-sum with the offset in the element array direction, between two data components that are arranged in the element array direction among data components included in another wavefront frame sequence corresponding to said another transmission of focused ultrasound and obtained by performing the delay-and-sum of the element input signals without the offset in the element array direction.

2. The ultrasound diagnostic system of claim 1, wherein:
the beamformer performs the delay-and-sum of element input signals by, upon setting the acoustic line positions of the acoustic elements in the acoustic element array, adjusting phase of signal waveforms inputted from each of the acoustic elements and combining the signal waveforms after adjusting phase, in order to form acoustic line waveforms of wavefront frames,
when element array direction interleaving is executed, the acoustic line positions determined for forming acoustic line waveforms in beamforming after a transmission of focused ultrasound are different from the acoustic line positions determined for forming acoustic line waveforms in beamforming after a subsequent transmission of focused ultrasound.

3. The ultrasound diagnostic system of claim 1, wherein:
the ultrasound signal processing circuit further includes a compounder that executes compound processing with respect to the combined wavefront frame sequence,
the compound processing including at least one of:
compound calculation with respect to a plurality of wavefront frame data in the time direction of a combined wavefront frame sequence obtained from frame interleaving, and replacing the plurality of wavefront data with compounded wavefront frame data obtained from the compound calculation, and
compound calculation with respect to data components in the element array direction of combined wavefront frame data obtained from element array direction interleaving, and replacing the data components with compounded data components obtained from the compound calculation.

4. The ultrasound diagnostic system of claim 1, wherein:
the frame time interval of the combined wavefront frame sequence is a value according to a pulse repetition time, and
the interleaver determines the pulse repetition time according to a setting made by a user within a numerical range that can be used for evaluating elastic modulus of the subject, and executes interleaving to make the frame time intervals of wavefront frame data in the combined wavefront frame sequence conform to the pulse repetition time.

5. The ultrasound diagnostic system of claim 1, wherein:
the ultrasound signal processing circuit further includes:
a controller that controls the push pulse controller, the generator, the interleaver, and the calculator to execute a sequence of an observation procedure from transmission of focused ultrasound, through wavefront frame data sequence generation and interleaving of wavefront frame data sequences, to calculation of elastic modulus, and
a display controller that generates an elastic modulus image according to a calculated elastic modulus from one iteration of the observation procedure and causes display of the elastic modulus image on a display to allow a user to perform an operation designating a region of the elastic modulus image, and
when a region of the elastic modulus image is designated, the interleaver executes element array direction interleaving by inserting a data component of wavefront frame data included in a wavefront frame data sequence obtained from an (N+1)-th observation procedure between two data components included in the region designated, among data components included in wavefront frame data included in a wavefront frame sequence obtained from an N-th observation procedure.

6. The ultrasound diagnostic system of claim 1, wherein:
the ultrasound signal processing circuit further includes:
a controller that controls the push pulse controller, the generator, the interleaver, and the calculator to execute a sequence of an observation procedure from transmission of focused ultrasound, through wavefront frame data sequence generation and interleaving of wavefront frame data sequences, to calculation of elastic modulus, and
a counter that counts the number of positions for which calculation of elastic modulus is impossible among a plurality of positions in the subject for which elastic modulus is to be calculated in one iteration of the observation procedure, and when the number of positions for which calculation of elastic modulus is impossible is greater than or equal to a predefined threshold, the interleaver executes element array direction interleaving by inserting a data component of wavefront frame data included in a wavefront frame data sequence obtained from an (N+1)-th observation procedure between two data components included in a region in which the positions for which calculation of elastic modulus is impossible are present, among data components included in wavefront frame data included in a wavefront frame sequence obtained from an N-th observation procedure.

7. The ultrasound diagnostic system of claim 1, wherein:
the ultrasound signal processing circuit further includes:
a controller that controls the push pulse controller, the generator, the interleaver, and the calculator to repeatedly execute a sequence of an observation procedure from transmission of focused ultrasound, through wavefront frame data sequence generation and interleaving of wavefront frame data sequences, to calculation of elastic modulus, and
a counter that counts the number of positions for which calculation of elastic modulus is impossible among a plurality of positions in the subject for which elastic modulus is to be calculated in one iteration of the observation procedure, and
execution of the observation procedure according to the controller is repeated until the number of positions for which calculation of elastic modulus is impossible drops below a predefined threshold.

8. An ultrasound diagnostic system comprising:
an ultrasound probe that has an acoustic element array comprising a plurality of acoustic elements in an element array direction; and
an ultrasound processing device comprising an ultrasound signal processing circuit including:
a push pulse controller that causes the acoustic element array to execute a plurality of transmissions of focused ultrasound to a same position in a subject, in order to generate radiation force in the subject;
a transmitter that controls the acoustic element array to execute transmission of reference ultrasound prior to the plurality of transmissions of focused ultrasound and to execute a plurality of transmissions of detection ultrasound after each of the plurality of transmissions of focused ultrasound and before a next transmission of focused ultrasound;
a generator that obtains a first wavefront frame data sequence and a second wavefront frame data sequence by detecting, at a plurality of time points, propagation of a shear wave caused by radiation force generated by a first transmission of the focused ultrasound and propagation of a shear wave caused by radiation force generated by a second transmission of the focused ultrasound transmitted consecutively with respect to the first transmission of the focused ultrasound;
an interleaver that obtains a combined wavefront frame sequence by interleaving the first wavefront frame data sequence and the second wavefront frame data sequence; and
a calculator that calculates shear wave speed and elastic modulus in the subject, by performing calculations using change amounts of propagation positions of a shear wave indicated by the combined wavefront frame sequence, wherein the generator comprises a beamformer that sets acoustic line positions for each of the plurality of acoustic elements of the acoustic element array, for forming acoustic line waveform corresponding to data components by phase shifting signal waveforms inputted from the plurality of acoustic elements and combining the phase-shifted signal waveforms, the generator generates wavefront frame data of the first wavefront frame sequence by setting acoustic positions to specific positions in element regions of the plurality of acoustic elements and forming acoustic line waveforms, the generator generates wavefront frame data of the second wavefront sequence by setting acoustic line positions with an offset in the element array direction as compared to the acoustic line positions set for generating the first wavefront frame sequence, such that the acoustic line positions for generating the wavefront frame data of the second wavefront frame sequence are set to positions different from the specific positions of the plurality of acoustic elements and between adjacent acoustic elements, and forming acoustic line waveforms, and the interleaver performs element array direction interleaving, in which a data component included in the wavefront frame data of the second frame sequence is inserted between two data components that are consecutive in the element array direction among data components included in the wavefront frame data of the first wavefront frame sequence.

* * * * *